(12) United States Patent
Hill et al.

(10) Patent No.: US 7,312,322 B1
(45) Date of Patent: Dec. 25, 2007

(54) GENETIC SEQUENCES ENCODING STEROID AND JUVENILE HORMONE RECEPTOR POLYPEPTIDES AND INSECTICIDAL MODALITIES THEREFOR

(75) Inventors: Ronald Johnston Hill, Forestville (AU); Garry Noel Hannan, Hunters Hill (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/346,470

(22) Filed: Jul. 1, 1999

Related U.S. Application Data

(63) Continuation-in-part of application No. PCT/AU99/00033, filed on Jan. 15, 1999.

(30) Foreign Application Priority Data

Jan. 15, 1998 (AU) .................................. 1356/98

(51) Int. Cl.
C07H 21/02 (2006.01)
C07H 21/04 (2006.01)
C12N 15/00 (2006.01)
C12N 5/00 (2006.01)
C12N 5/02 (2006.01)

(52) U.S. Cl. .................... 536/23.1; 536/23.5; 536/24.1; 435/320.1; 435/325

(58) Field of Classification Search ............... 435/69.1, 435/320.1, 6, 325, 23.1; 536/23.1
See application file for complete search history.

(56) References Cited

U.S. PATENT DOCUMENTS

| | | | |
|---|---|---|---|
| 4,859,609 A | 8/1989 | Dull et al. | |
| 5,352,451 A | 10/1994 | Miller et al. | 424/93.2 |
| 5,514,578 A | 5/1996 | Hogness | 435/240.2 |
| 5,641,652 A | 6/1997 | Oro et al. | |
| 5,688,691 A | 11/1997 | Oro et al. | 455/348 |
| 6,025,483 A | 2/2000 | Yanofsky | 536/23.6 |
| 6,110,698 A | 8/2000 | Heinrich | 435/29 |
| 6,245,531 B1 | 6/2001 | Hogness | 435/69.7 |
| 6,258,603 B1 | 7/2001 | Carlson | 435/468 |
| 6,265,173 B1 | 7/2001 | Evans | 435/7.1 |
| 6,281,330 B1 | 8/2001 | Evans | 530/324 |

FOREIGN PATENT DOCUMENTS

| | | |
|---|---|---|
| WO | 91/13167 | 9/1991 |
| WO | 93/03162 | 2/1993 |
| WO | 96/37609 | 11/1996 |
| WO | 97/38117 | 10/1997 |
| WO | 97/45731 | 12/1997 |
| WO | 97/45737 | 12/1997 |
| WO | 98/35550 | 8/1998 |
| WO | WO 99/36520 | 7/1999 |
| WO | WO 99/48915 | 9/1999 |
| WO | 00/15791 | 3/2000 |

OTHER PUBLICATIONS

Mouillet, Cloning of two putative ecdysteroid receptor isoforms from Tenebrio molitor and their developmental expression in the epidermis during metamorphosis. 1997. Eur. J. Biochem. vol. 248 pp. 850-863.*
Mikayama T. Molecular cloning and functional expression of a cDNA encoding glycosylation-inhibiting factor. Proc. Natl. Acad. Sci. USA vol. 90, pp. 10056-10060, 1993.*
Voet et al. Biochemistry. 1990. John Wiley & Sons, Inc.. pp. 126-128 and 228-234.*
Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Wang et al. 1999. Nuc. Acids. Res. 27:4609-4618.*
Kaufman et al. 1999. Blood. 94:3178-3184.*
Campbell et al., 1997. Theriology 47:63-72.*
Phillips AJ. 2001 J Pharm Pharmacology 53:1169-1174.*
Wells 1990. Biochemistry. 29:8509-8517.*
Ngo et al. 1994. The Protein Folding Problem and Tertiary Structure Prediction. pp. 492-495.*
Elbrecht et al. (1996) "8-0-Acetylharpagide Is a Nonsteroidal Ecdysteroid Agonist" Insect Biochem. Molec. Biol. 26:519-523.
Fujiwara et al. (1995) "Cloning of an Ecdysone Receptor Homolog from Manduca sexta and the Developmental Profile of Its mRNA in Wings" Insect Biochem. Molec. Biol. 25:845-856.
Hannan and Hill (1997) "Cloning and Characterization of LcEcR[1]: A Functional Ecdysone Receptor from the Sheep Blowfly Lucilia cuprina" Insect Biochem. Molec. Biol. 27:479-488.
Ishaaya et al. (1995) "Comparative Toxicity of Two Ecdysteroid Agonists, RH-2485 and RH-5992, on Susceptible and Pyrethroid-Resistant Strains of the Egyptian Cotton Leafworm, Spodoptera littoralis" Phytoparasitica 23:139-145.

(Continued)

Primary Examiner—Lorraine Spector
Assistant Examiner—Shulamith H. Shafer
(74) Attorney, Agent, or Firm—Greenlee Winner and Sullivan, PC

(57) ABSTRACT

The present invention provides isolated nucleic acid molecules encoding polypeptides comprising functional steroid hormone and juvenile hormone receptors, in particular isolated nucleic acid molecules which encode polypeptides comprising the Lucilia cuprina and Myzus persicae ecdysone receptors and juvenile hormone receptors. The present invention further provides functional recombinant steroid and juvenile hormone receptors and recombinant polypeptide subunits thereof and derivatives and analogues thereof. The present invention further provides screening systems and methods of identifying insecticidally-active agents which are capable of agonizing or antagonizing insect receptor function, or alternatively or in addition, which modify the affinity of said receptors for their cellular stimuli (eg. insect steroids or juvenile hormones) or analogues thereof, or alternatively or in addition, which act as insecticides by virtue of their ability to agonize or antagonize the activity of insect hormones.

15 Claims, 4 Drawing Sheets

OTHER PUBLICATIONS

Oberlander et al. (1995) "Non-Steroidal Ecdysteroid Agonists: Tools for the Study of Hormonal Action" *Archives of Insect Biochemistry and Physiology* 28:209-223.

GenPept, Accession No. AAB94565, (Submitted Aug. 1997), Guo et al., *Amblyomma americanum* ecdysteroid receptor (AamEcRA3) mRNA, complete cds.

GenPept, Accession No. AAB94566, (Submitted Aug. 1997), Guo et al., *Amblyomma Americanum* ecdsyteroid receptor (AamEcRA1) mRNA, complete cds.

GenPept, Accession No. AAC59721, (1995), Jones et al., Danio rerio retinoid X receptor delta (RXR-delta (RXR-delta) mRNA, complete cds.

GenPept, Accession No. AAC59722, (1995), Jones et al., Danio rerio retinoid X receptor epsilon (RXR-epsilon) mRNA, complete cds.

GenPept, Accession No. AAC95154, (Submitted Oct. 1998), Vaillancourt et al., Cloning vector pERV3, complete sequence.

GenPept, Accession No. AAD19828, (Submitted Feb. 1998), Saleh et al., *Locusta migratoria* ecdysone receptor mRNA, complete cds.

GenBank, Accession No. CAA36827, (1990), Henrich, V.C. Steroid hormone receptor-like protein (AA 1-507) [*Drosophila melanogaster*].

GenPept, Accession No. CAA72296, Mouillet J.F., Tenebrio molitor mRNA for ecdysone receptor.

Swiss-Prot, Accession No. 018531, (Submitted Dec. 1998), Hannan, G.N. and Hill, R.J., *Lucilia cuprina* Ecdysone Receptor.

Swiss-Prot, Accession No. P19793, (Submitted Feb. 1991), Manglesdorf et al., Retinoic acid receptor RXR-Alpha, *Homo sapiens*.

Swiss-Prot, Accession No. P28700, (Submitted Dec. 1992), Leid et al., Retinoic acid receptor RXR-Alpha, *Mus musculus*.

GenBank, Swiss-Prot, Accession No. P34021, (Submitted Feb. 1994), Koelle et al., Ecdysone receptor (Ecdysteroid receptor), *Drosophila melanogaster*.

Swiss-Prot, Accession No. P20153, (Submitted Feb. 1991), Oro et al., *Ultraspiracle* protein, *Drosophila melangaster*.

Cho, W-L. et al. (1995) "Mosquito Ecdysteroid Receptor: Analysis of the cDNA and Expression During Vitellogenesis"; *Insect Biochem. Molec. Biol.* 25(1):19-27.

Guo, X. et al. (1998) "Isolation of two functional retinoid X receptor subtypes from the Ixodid tick, *Amblyomma americanum* (L.)";*Molecular and Cellular Endocrinology* 139(1-2):45-60.

Jindra, M. et al. (1997) "Identification and mRNA developmental profiles of two *ultraspiracle* isoforms in the epidermis and wings of *Manduca sexta*"; *Insect Molecular Biology* 6(1):41-53.

Mouillet, J-F. et al. (1997) "Cloning of two putative ecdysteroid receptor isoforms from *Tenebrio molitor* and their developmental expression in the epidermis during metamorphosis"; *European Journal of Biochemistry* 248:856-863.

Oro, A.E. et al. (1990) "Relationship between the product of the *Drosophila ultraspiracle* locus and the vertebrate retinoid X receptor"; *Nature* 347(6290):298-301.

Halling, B.P. et al. (Jul. 1999), "Expression and Purification of the Hormone Binding Domain of the *Drosophila* Ecdysone and Ultraspiracle Receptors," Protein Expression Purification 17:373-386.

Hannan, G.N. and Hill, R.J. (Jun. 2001), "*Lcusp*, an *ultraspiracle* gene from the sheep blowfly, *Lucilia cuprina*:cDNA cloning, developmental expression of RNA and confirmation of function," Insect Biochem. Mol. Biol. 31:771-781.

Kapitskaya, M. et al. (1996), "The mosquito *ultraspiracle* homologue, a partner of ecdysteroid receptor heterodimer: cloning and characterization of isoforms expressed during vitellogenesis," Mol. Cell. Endocrinol. 121:119-132.

Li, C. et al. (Mar. 1997), "Coexpression of nuclear receptor partners increases their solubility and biological activities," Proc. Natl. Acad. Sci. USA 94:2278-2283.

Palli, S.R. et al. (Feb. 1999), "Biochemical and biological mode of action of ecdysone agonists on the spruce budworm," Pestic. Sci. 55:633-675.

Perera, S.C. et al. (pub. on-line May1999), "An Analysis of Ecdysone Receptor Domains Required for Heterodimerization With *Ultraspirale*," Arch. Insect Biochem. Physiol. 41:61-70.

Tzertzinis, G. et al. (1994), "BmCF1, a Bombyx mori RXR-type Receptor Related to the *Drosophila* ultraspiracle," J. Mol. Biol. 238:479-486.

Yao, T-P. et al. (Oct. 1992), "*Drosophila ultraspiracle* Modulates Ecdysone Receptor Function via Heterodimer Formation," Cell 71:63-72.

Perara et al. (1998) "The *Ultraspiracle* Gene of the Spruce Budworm, *Choristoneura fumiferana*: Cloning of cDNA and Developmental Expression of mRNA," Dev. Genetics 22:169-179.

* cited by examiner

SEQUENCE LISTING

<160> NUMBER OF SEQ ID NOS: 20

<210> SEQ ID NO 1
<211> LENGTH: 2274
<212> TYPE: DNA
<213> ORGANISM: Lucilia cuprina
<220> FEATURE:
<221> NAME/KEY: CDS
<222> LOCATION: (1)..(2271)

<400> SEQUENCE: 1

```
atg atg aaa cga cgt tgg tct aat aat ggc ggt ttt gcc gct tta aaa        48
Met Met Lys Arg Arg Trp Ser Asn Asn Gly Gly Phe Ala Ala Leu Lys
 1               5                  10                  15 atg tta gaa gaa tcc tcc tca gaa gta acc tcc tcc tca aat ggt ctg        96
Met Leu Glu Glu Ser Ser Ser Glu Val Thr Ser Ser Ser Asn Gly Leu
             20                  25                  30 gtc ttg tca tcg gat ata aat atg tca cct tcc tcg ttg gat tca ccc       144
Val Leu Ser Ser Asp Ile Asn Met Ser Pro Ser Ser Leu Asp Ser Pro
         35                  40                  45
```

```
gtt tat ggc gat cag gaa atg tgg ctg tgt aac gat tca gct tca tat      192
Val Tyr Gly Asp Gln Glu Met Trp Leu Cys Asn Asp Ser Ala Ser Tyr
 50                  55                  60 aat aac agt cat cag cat agt gtt ata act tcg ctg cag ggc tgc acc      240
Asn Asn Ser His Gln His Ser Val Ile Thr Ser Leu Gln Gly Cys Thr
 65                  70                  75                  80 tca tca ttg ccg gcc caa aca acc att ata cct ctg tca gct tta ccc      288
Ser Ser Leu Pro Ala Gln Thr Thr Ile Ile Pro Leu Ser Ala Leu Pro
                 85                  90                  95 aat tcc aat aat gcc tcc ctg aat aat caa aat caa aat tat caa aat      336
Asn Ser Asn Asn Ala Ser Leu Asn Asn Gln Asn Gln Asn Tyr Gln Asn
            100                 105                 110 ggt aat tcc atg aat aca aat tta tcg gtt aac aca aat aac agt gtt      384
Gly Asn Ser Met Asn Thr Asn Leu Ser Val Asn Thr Asn Asn Ser Val
        115                 120                 125 gga gga ggt gga ggt ggt ggt ggt gta ccc ggt atg act tca ctc aat      432
Gly Gly Gly Gly Gly Gly Gly Gly Val Pro Gly Met Thr Ser Leu Asn
130                 135                 140 ggt ctg ggt ggt ggt ggt ggc agt caa gtg aat aat cac aat cac agc      480
Gly Leu Gly Gly Gly Gly Gly Ser Gln Val Asn Asn His Asn His Ser
145                 150                 155                 160 cac aat cat tta cac cac aac agc aac agt aat cac agt aat agc agt      528
His Asn His Leu His His Asn Ser Asn Ser Asn His Ser Asn Ser Ser
                165                 170                 175 tcc cac cac aca aat ggc cac atg ggt att ggc ggt ggt ggt ggc          576
Ser His His Thr Asn Gly His Met Gly Ile Gly Gly Gly Gly Gly Gly
            180                 185                 190 tta tcg gtc aat att aat ggt ccc aat atc gtt agc aat gcc caa cag      624
Leu Ser Val Asn Ile Asn Gly Pro Asn Ile Val Ser Asn Ala Gln Gln
        195                 200                 205 tta aac tcg tta cag gcc tca caa aat ggc caa gtt att cat gcc aat      672
Leu Asn Ser Leu Gln Ala Ser Gln Asn Gly Gln Val Ile His Ala Asn
210                 215                 220 att ggc att cac agt atc atc agt aat gga tta aat cat cat cac cat      720
Ile Gly Ile His Ser Ile Ile Ser Asn Gly Leu Asn His His His His
225                 230                 235                 240 cat cat atg aat aac agt agt atg atg cat cat aca ccc aga tct gaa      768
His His Met Asn Asn Ser Ser Met Met His His Thr Pro Arg Ser Glu
                245                 250                 255 tca gct aat tcc ata tca tca ggt cgt gat gat ctt tca ccc tcg agc      816
Ser Ala Asn Ser Ile Ser Ser Gly Arg Asp Asp Leu Ser Pro Ser Ser
            260                 265                 270 agt ctt aat ggc ttc tca aca agc gat gct agt gat gtt aag aaa atc      864
Ser Leu Asn Gly Phe Ser Thr Ser Asp Ala Ser Asp Val Lys Lys Ile
        275                 280                 285 aaa aaa ggt cct gcg ccc cgt tta caa gag gaa ctg tgt ctg gtg tgt      912
Lys Lys Gly Pro Ala Pro Arg Leu Gln Glu Glu Leu Cys Leu Val Cys
290                 295                 300 ggt gat cgg gcg tcc ggt tat cat tat aac gca ctc acc tgt gaa ggc      960
Gly Asp Arg Ala Ser Gly Tyr His Tyr Asn Ala Leu Thr Cys Glu Gly
305                 310                 315                 320 tgt aag ggg ttc ttt cga cgg agt gtt acc aaa aat gcg gtg tat tgt     1008
Cys Lys Gly Phe Phe Arg Arg Ser Val Thr Lys Asn Ala Val Tyr Cys
                325                 330                 335 tgt aaa ttt ggt cat gcc tgc gaa atg gac atg tat atg cga cgt aaa     1056
Cys Lys Phe Gly His Ala Cys Glu Met Asp Met Tyr Met Arg Arg Lys
            340                 345                 350 tgt cag gaa tgt agg ctg aaa aaa tgt ttg gct gtg ggc atg cgg ccg     1104
Cys Gln Glu Cys Arg Leu Lys Lys Cys Leu Ala Val Gly Met Arg Pro
```

```
                         355                 360                 365
gaa tgt gtg gtg ccc gaa aac cag tgt gca atg aaa cga cgc gaa aag      1152
Glu Cys Val Val Pro Glu Asn Gln Cys Ala Met Lys Arg Arg Glu Lys
370                 375                 380 aaa gca caa aaa gag aag gat aaa ata cag acc agt gtg tgt gca acg      1200
Lys Ala Gln Lys Glu Lys Asp Lys Ile Gln Thr Ser Val Cys Ala Thr
385                 390                 395                 400 gaa att aaa aag gaa ata ctc gat tta atg aca tgt gaa ccg cca tca      1248
Glu Ile Lys Lys Glu Ile Leu Asp Leu Met Thr Cys Glu Pro Pro Ser
                405                 410                 415 cat cca acg tgt ccg ctg tta cct gaa gac att ttg gct aaa tgt caa      1296
His Pro Thr Cys Pro Leu Leu Pro Glu Asp Ile Leu Ala Lys Cys Gln
            420                 425                 430 gct cgt aat ata cct cct tta tcg tac aat caa ttg gca gtt ata tat      1344
Ala Arg Asn Ile Pro Pro Leu Ser Tyr Asn Gln Leu Ala Val Ile Tyr
        435                 440                 445 aaa tta ata tgg tat caa gat ggc tac gaa cag cca tcc gag gaa gat      1392
Lys Leu Ile Trp Tyr Gln Asp Gly Tyr Glu Gln Pro Ser Glu Glu Asp
450                 455                 460 ctc aaa cgt ata atg agt tca ccc gat gaa aat gaa agt caa cac gat      1440
Leu Lys Arg Ile Met Ser Ser Pro Asp Glu Asn Glu Ser Gln His Asp
465                 470                 475                 480 gca tca ttt cgt cat ata aca gaa atc act ata cta aca gta caa tta      1488
Ala Ser Phe Arg His Ile Thr Glu Ile Thr Ile Leu Thr Val Gln Leu
                485                 490                 495 att gtg gaa ttt gcc aag ggt ttg cca gcg ttt acc aaa ata cca caa      1536
Ile Val Glu Phe Ala Lys Gly Leu Pro Ala Phe Thr Lys Ile Pro Gln
            500                 505                 510 gag gat caa ata aca cta tta aag gcc tgc tca tca gaa gtt atg atg      1584
Glu Asp Gln Ile Thr Leu Leu Lys Ala Cys Ser Ser Glu Val Met Met
        515                 520                 525 ttg cga atg gca cga cgt tac gat cac aat tca gat tcg ata ttc ttt      1632
Leu Arg Met Ala Arg Arg Tyr Asp His Asn Ser Asp Ser Ile Phe Phe
530                 535                 540 gcc aat aat cga tcg tat acg cgt gac tct tat aaa atg gct ggc atg      1680
Ala Asn Asn Arg Ser Tyr Thr Arg Asp Ser Tyr Lys Met Ala Gly Met
545                 550                 555                 560 gct gat aat att gag gat ctg ctg cat ttc tgt cga caa atg tac tcg      1728
Ala Asp Asn Ile Glu Asp Leu Leu His Phe Cys Arg Gln Met Tyr Ser
                565                 570                 575 atg aaa gtg gac aat gtc gaa tat gct cta ctc act gcc att gtg atc      1776
Met Lys Val Asp Asn Val Glu Tyr Ala Leu Leu Thr Ala Ile Val Ile
            580                 585                 590 ttt tcc gat cgg ccg ggt ctc gaa gaa gcc gaa cta gtc gaa gcg ata      1824
Phe Ser Asp Arg Pro Gly Leu Glu Glu Ala Glu Leu Val Glu Ala Ile
        595                 600                 605 caa agt tac tac atc gat aca ctc cgc att tac ata ctt aat cgc cat      1872
Gln Ser Tyr Tyr Ile Asp Thr Leu Arg Ile Tyr Ile Leu Asn Arg His
610                 615                 620 tgc ggc gat ccc atg agt ctc gta ttc ttt gcc aag ctt ctg tca att      1920
Cys Gly Asp Pro Met Ser Leu Val Phe Phe Ala Lys Leu Leu Ser Ile
625                 630                 635                 640 cta acc gaa ctg cgt acg ttg ggc aat caa aat gcc gaa atg tgt ttc      1968
Leu Thr Glu Leu Arg Thr Leu Gly Asn Gln Asn Ala Glu Met Cys Phe
                645                 650                 655 tcg ttg aaa ttg aaa aat cgc aaa ctg cca aaa ttc ctc gaa gag atc      2016
Ser Leu Lys Leu Lys Asn Arg Lys Leu Pro Lys Phe Leu Glu Glu Ile
            660                 665                 670 tgg gat gta cat gcc att cca ccc tca gtg cag tca cac ata cag gct      2064
```

-continued

| | | | | | | | | | | | | |
|---|---|---|---|---|---|---|---|---|---|---|---|---|
| Trp | Asp | Val | His | Ala | Ile | Pro | Pro | Ser | Val | Gln | Ser | His | Ile | Gln | Ala |
| | | 675 | | | | 680 | | | | 685 | | |

```
acc cag gcg gaa aag gcc gcc cag gaa gct cag gca aca aca tcg gcc    2112
Thr Gln Ala Glu Lys Ala Ala Gln Glu Ala Gln Ala Thr Thr Ser Ala
        690                 695                 700 att tca gca gcc gcc acc tca tct tcc tcc ata aat acc tcg atg gca    2160
Ile Ser Ala Ala Ala Thr Ser Ser Ser Ser Ile Asn Thr Ser Met Ala
705                 710                 715                 720 aca tca tcc tca tca tcg tta tcg cca tcg gcg gcc tca aca ccc aat    2208
Thr Ser Ser Ser Ser Ser Leu Ser Pro Ser Ala Ala Ser Thr Pro Asn
                725                 730                 735 ggt ggt gcc gtc gat tat gtt ggc acc gat atg agt atg agt tta gta    2256
Gly Gly Ala Val Asp Tyr Val Gly Thr Asp Met Ser Met Ser Leu Val
            740                 745                 750 caa tcg gat aat gca tag                                            2274
Gln Ser Asp Asn Ala
        755

<210> SEQ ID NO 2
<211> LENGTH: 757
<212> TYPE: PRT
<213> ORGANISM: Lucilia cuprina

<400> SEQUENCE: 2
```

| Met | Met | Lys | Arg | Arg | Trp | Ser | Asn | Asn | Gly | Gly | Phe | Ala | Ala | Leu | Lys |
|---|---|---|---|---|---|---|---|---|---|---|---|---|---|---|---|
| 1 | | | | 5 | | | | | 10 | | | | | 15 | |

| Met | Leu | Glu | Glu | Ser | Ser | Ser | Glu | Val | Thr | Ser | Ser | Ser | Asn | Gly | Leu |
|---|---|---|---|---|---|---|---|---|---|---|---|---|---|---|---|
| | | | 20 | | | | | 25 | | | | | 30 | | |

| Val | Leu | Ser | Ser | Asp | Ile | Asn | Met | Ser | Pro | Ser | Ser | Leu | Asp | Ser | Pro |
|---|---|---|---|---|---|---|---|---|---|---|---|---|---|---|---|
| | | 35 | | | | | 40 | | | | | 45 | | | |

| Val | Tyr | Gly | Asp | Gln | Glu | Met | Trp | Leu | Cys | Asn | Asp | Ser | Ala | Ser | Tyr |
|---|---|---|---|---|---|---|---|---|---|---|---|---|---|---|---|
| | 50 | | | | | 55 | | | | | 60 | | | | |

| Asn | Asn | Ser | His | Gln | His | Ser | Val | Ile | Thr | Ser | Leu | Gln | Gly | Cys | Thr |
|---|---|---|---|---|---|---|---|---|---|---|---|---|---|---|---|
| 65 | | | | | 70 | | | | | 75 | | | | | 80 |

| Ser | Ser | Leu | Pro | Ala | Gln | Thr | Thr | Ile | Ile | Pro | Leu | Ser | Ala | Leu | Pro |
|---|---|---|---|---|---|---|---|---|---|---|---|---|---|---|---|
| | | | | 85 | | | | | 90 | | | | | 95 | |

| Asn | Ser | Asn | Asn | Ala | Ser | Leu | Asn | Asn | Gln | Asn | Gln | Asn | Tyr | Gln | Asn |
|---|---|---|---|---|---|---|---|---|---|---|---|---|---|---|---|
| | | | 100 | | | | | 105 | | | | | 110 | | |

| Gly | Asn | Ser | Met | Asn | Thr | Asn | Leu | Ser | Val | Asn | Thr | Asn | Asn | Ser | Val |
|---|---|---|---|---|---|---|---|---|---|---|---|---|---|---|---|
| | | 115 | | | | | 120 | | | | | 125 | | | |

| Gly | Gly | Gly | Gly | Gly | Gly | Gly | Val | Pro | Gly | Met | Thr | Ser | Leu | Asn |
|---|---|---|---|---|---|---|---|---|---|---|---|---|---|---|
| 130 | | | | | 135 | | | | | 140 | | | | |

| Gly | Leu | Gly | Gly | Gly | Gly | Ser | Gln | Val | Asn | Asn | His | Asn | His | Ser |
|---|---|---|---|---|---|---|---|---|---|---|---|---|---|---|
| 145 | | | | | 150 | | | | | 155 | | | | | 160 |

| His | Asn | His | Leu | His | His | Asn | Ser | Asn | Ser | Asn | His | Ser | Asn | Ser | Ser |
|---|---|---|---|---|---|---|---|---|---|---|---|---|---|---|---|
| | | | | 165 | | | | | 170 | | | | | 175 | |

| Ser | His | His | Thr | Asn | Gly | His | Met | Gly | Ile | Gly | Gly | Gly | Gly | Gly |
|---|---|---|---|---|---|---|---|---|---|---|---|---|---|---|
| | | | 180 | | | | | 185 | | | | | 190 | |

| Leu | Ser | Val | Asn | Ile | Asn | Gly | Pro | Asn | Ile | Val | Ser | Asn | Ala | Gln | Gln |
|---|---|---|---|---|---|---|---|---|---|---|---|---|---|---|---|
| | | | 195 | | | | | 200 | | | | | 205 | | |

| Leu | Asn | Ser | Leu | Gln | Ala | Ser | Gln | Asn | Gly | Gln | Val | Ile | His | Ala | Asn |
|---|---|---|---|---|---|---|---|---|---|---|---|---|---|---|---|
| | 210 | | | | | 215 | | | | | 220 | | | | |

| Ile | Gly | Ile | His | Ser | Ile | Ile | Ser | Asn | Gly | Leu | Asn | His | His | His |
|---|---|---|---|---|---|---|---|---|---|---|---|---|---|---|
| 225 | | | | | 230 | | | | | 235 | | | | | 240 |

| His | His | Met | Asn | Asn | Ser | Ser | Met | Met | His | His | Thr | Pro | Arg | Ser | Glu |
|---|---|---|---|---|---|---|---|---|---|---|---|---|---|---|---|
| | | | | 245 | | | | | 250 | | | | | 255 | |

```
Ser Ala Asn Ser Ile Ser Ser Gly Arg Asp Asp Leu Ser Pro Ser Ser
            260                 265                 270

Ser Leu Asn Gly Phe Ser Thr Ser Asp Ala Ser Asp Val Lys Lys Ile
            275                 280                 285

Lys Lys Gly Pro Ala Pro Arg Leu Gln Glu Glu Leu Cys Leu Val Cys
        290                 295                 300

Gly Asp Arg Ala Ser Gly Tyr His Tyr Asn Ala Leu Thr Cys Glu Gly
305                 310                 315                 320

Cys Lys Gly Phe Phe Arg Arg Ser Val Thr Lys Asn Ala Val Tyr Cys
                325                 330                 335

Cys Lys Phe Gly His Ala Cys Glu Met Asp Met Tyr Met Arg Arg Lys
            340                 345                 350

Cys Gln Glu Cys Arg Leu Lys Lys Cys Leu Ala Val Gly Met Arg Pro
            355                 360                 365

Glu Cys Val Val Pro Glu Asn Gln Cys Ala Met Lys Arg Arg Glu Lys
370                 375                 380

Lys Ala Gln Lys Glu Lys Asp Lys Ile Gln Thr Ser Val Cys Ala Thr
385                 390                 395                 400

Glu Ile Lys Lys Glu Ile Leu Asp Leu Met Thr Cys Glu Pro Pro Ser
                405                 410                 415

His Pro Thr Cys Pro Leu Leu Pro Glu Asp Ile Leu Ala Lys Cys Gln
            420                 425                 430

Ala Arg Asn Ile Pro Pro Leu Ser Tyr Asn Gln Leu Ala Val Ile Tyr
        435                 440                 445

Lys Leu Ile Trp Tyr Gln Asp Gly Tyr Glu Gln Pro Ser Glu Glu Asp
    450                 455                 460

Leu Lys Arg Ile Met Ser Ser Pro Asp Glu Asn Glu Ser Gln His Asp
465                 470                 475                 480

Ala Ser Phe Arg His Ile Thr Glu Ile Thr Ile Leu Thr Val Gln Leu
                485                 490                 495

Ile Val Glu Phe Ala Lys Gly Leu Pro Ala Phe Thr Lys Ile Pro Gln
            500                 505                 510

Glu Asp Gln Ile Thr Leu Leu Lys Ala Cys Ser Ser Glu Val Met Met
        515                 520                 525

Leu Arg Met Ala Arg Arg Tyr Asp His Asn Ser Asp Ser Ile Phe Phe
530                 535                 540

Ala Asn Asn Arg Ser Tyr Thr Arg Asp Ser Tyr Lys Met Ala Gly Met
545                 550                 555                 560

Ala Asp Asn Ile Glu Asp Leu Leu His Phe Cys Arg Gln Met Tyr Ser
                565                 570                 575

Met Lys Val Asp Asn Val Glu Tyr Ala Leu Leu Thr Ala Ile Val Ile
            580                 585                 590

Phe Ser Asp Arg Pro Gly Leu Glu Glu Ala Glu Leu Val Glu Ala Ile
        595                 600                 605

Gln Ser Tyr Tyr Ile Asp Thr Leu Arg Ile Tyr Ile Leu Asn Arg His
    610                 615                 620

Cys Gly Asp Pro Met Ser Leu Val Phe Phe Ala Lys Leu Leu Ser Ile
625                 630                 635                 640

Leu Thr Glu Leu Arg Thr Leu Gly Asn Gln Asn Ala Glu Met Cys Phe
                645                 650                 655

Ser Leu Lys Leu Lys Asn Arg Lys Leu Pro Lys Phe Leu Glu Glu Ile
            660                 665                 670

Trp Asp Val His Ala Ile Pro Pro Ser Val Gln Ser His Ile Gln Ala
```

-continued

```
                675                 680                 685
Thr Gln Ala Glu Lys Ala Ala Gln Glu Ala Gln Ala Thr Thr Ser Ala
        690                 695                 700

Ile Ser Ala Ala Ala Thr Ser Ser Ser Ile Asn Thr Ser Met Ala
705                 710                 715                 720

Thr Ser Ser Ser Ser Leu Ser Pro Ser Ala Ala Ser Thr Pro Asn
                725                 730                 735

Gly Gly Ala Val Asp Tyr Val Gly Thr Asp Met Ser Met Ser Leu Val
                740                 745                 750

Gln Ser Asp Asn Ala
        755

<210> SEQ ID NO 3
<211> LENGTH: 1401
<212> TYPE: DNA
<213> ORGANISM: Lucilia cuprina
<220> FEATURE:
<221> NAME/KEY: CDS
<222> LOCATION: (1)..(1401)

<400> SEQUENCE: 3 atg gat aac ggc gag caa gat gct ggg ttc cga ttg gca ccg atg tct      48
Met Asp Asn Gly Glu Gln Asp Ala Gly Phe Arg Leu Ala Pro Met Ser
1               5                   10                  15 ccg cag gag ata aag cca gac att tca cta ctc aat gaa aat aat acg      96
Pro Gln Glu Ile Lys Pro Asp Ile Ser Leu Leu Asn Glu Asn Asn Thr
            20                  25                  30 agt agt tat tcg ccc aaa cct gga agt cct aat cca ttt gcc atc gga     144
Ser Ser Tyr Ser Pro Lys Pro Gly Ser Pro Asn Pro Phe Ala Ile Gly
        35                  40                  45 ttg cag gca ata aat gca gtc gct gcc gcg aat gcc aat aac caa aat     192
Leu Gln Ala Ile Asn Ala Val Ala Ala Ala Asn Ala Asn Asn Gln Asn
    50                  55                  60 caa atg ttg caa act acg cca cca caa cag cag cag tat cca cca aat     240
Gln Met Leu Gln Thr Thr Pro Pro Gln Gln Gln Gln Tyr Pro Pro Asn
65                  70                  75                  80 cac ccc ctt agt ggt tcg aaa cac ttg tgt tcc att tgt gga gac cgc     288
His Pro Leu Ser Gly Ser Lys His Leu Cys Ser Ile Cys Gly Asp Arg
                85                  90                  95 gcc agt gga aaa cat tat ggg gtc tac agt tgt gag ggt tgt aaa ggg     336
Ala Ser Gly Lys His Tyr Gly Val Tyr Ser Cys Glu Gly Cys Lys Gly
            100                 105                 110 ttc ttc aaa cgt acc gta cgc aag gac ttg aca tat gct tgt cgt gag     384
Phe Phe Lys Arg Thr Val Arg Lys Asp Leu Thr Tyr Ala Cys Arg Glu
        115                 120                 125 gac aga aat tgc att ata gat aaa cga caa aga aat cgt tgc cag tat     432
Asp Arg Asn Cys Ile Ile Asp Lys Arg Gln Arg Asn Arg Cys Gln Tyr
    130                 135                 140 tgt cgt tat caa aag tgt tta gct tgt ggc atg aaa cgc gaa gcg gtc     480
Cys Arg Tyr Gln Lys Cys Leu Ala Cys Gly Met Lys Arg Glu Ala Val
145                 150                 155                 160 caa gag gaa cga caa cgt ggt act cgt gct gct aac gct aga gct gct     528
Gln Glu Glu Arg Gln Arg Gly Thr Arg Ala Ala Asn Ala Arg Ala Ala
                165                 170                 175 ggt gct ggc ggt ggt gga gga ggt ggt ggt ggg gta agc aat gtg gtt     576
Gly Ala Gly Gly Gly Gly Gly Gly Gly Gly Val Ser Asn Val Val
            180                 185                 190 ggt gct ggc gga gaa gac ttt aaa ccc agc agt tca tta cgt gat ctc     624
Gly Ala Gly Gly Glu Asp Phe Lys Pro Ser Ser Ser Leu Arg Asp Leu
        195                 200                 205
```

-continued

```
act ata gaa cgc atc att gaa gcc gag caa aag gct gaa tct ttg agc      672
Thr Ile Glu Arg Ile Ile Glu Ala Glu Gln Lys Ala Glu Ser Leu Ser
    210                 215                 220 ggt gat aac gtg ttg ccc ttt ttg cgc gtt ggc aac aat tcc atg gta      720
Gly Asp Asn Val Leu Pro Phe Leu Arg Val Gly Asn Asn Ser Met Val
225                 230                 235                 240 caa cac gac tac aaa ggc gcg gta tct cat ctc tgc cag atg gtt aac      768
Gln His Asp Tyr Lys Gly Ala Val Ser His Leu Cys Gln Met Val Asn
                245                 250                 255 aaa caa ctc tac caa atg gtt gaa tat gca cgt cga aca cca cat ttt      816
Lys Gln Leu Tyr Gln Met Val Glu Tyr Ala Arg Arg Thr Pro His Phe
        260                 265                 270 aca cat ttg cag cgt gag gat cag ata cta ttg tta aag gct ggc tgg      864
Thr His Leu Gln Arg Glu Asp Gln Ile Leu Leu Leu Lys Ala Gly Trp
    275                 280                 285 aat gaa ctg cta att gca aat gtt gcc tgg tgc agt att gag tct ctg      912
Asn Glu Leu Leu Ile Ala Asn Val Ala Trp Cys Ser Ile Glu Ser Leu
290                 295                 300 gat gcc gaa tat gcc tct cct ggt acg gta cat gac ggt tct ttt ggt      960
Asp Ala Glu Tyr Ala Ser Pro Gly Thr Val His Asp Gly Ser Phe Gly
305                 310                 315                 320 cgg cgt tca cca gtg cgt cag ccc caa caa ctc ttc ctt aat cag aat     1008
Arg Arg Ser Pro Val Arg Gln Pro Gln Gln Leu Phe Leu Asn Gln Asn
                325                 330                 335 ttc tcg tat cat cgc aat agt gct att aag gcc aat gtt gtt tca att     1056
Phe Ser Tyr His Arg Asn Ser Ala Ile Lys Ala Asn Val Val Ser Ile
                340                 345                 350 ttc gat cgt atc ctc tcg gag ttg agc atc aaa atg aaa cgt ctt aac     1104
Phe Asp Arg Ile Leu Ser Glu Leu Ser Ile Lys Met Lys Arg Leu Asn
            355                 360                 365 atc gat cgc tcg gag ttg tcg tgt ctg aag gca atc ata ctc ttc aat     1152
Ile Asp Arg Ser Glu Leu Ser Cys Leu Lys Ala Ile Ile Leu Phe Asn
370                 375                 380 cca gac ata cgc ggt ctg aaa tgt cga gcc gac gtc gag gta tgt cgt     1200
Pro Asp Ile Arg Gly Leu Lys Cys Arg Ala Asp Val Glu Val Cys Arg
385                 390                 395                 400 gaa aaa atc tat gcc tgt ctg gac gaa cac tgc cgc aca gaa cat cca     1248
Glu Lys Ile Tyr Ala Cys Leu Asp Glu His Cys Arg Thr Glu His Pro
                405                 410                 415 ggt gat gat ggc cgc ttt gct cag cta cta cta agg ttg ccc gca ttg     1296
Gly Asp Asp Gly Arg Phe Ala Gln Leu Leu Leu Arg Leu Pro Ala Leu
                420                 425                 430 cgt tcc atc agt ctc aaa tgt ctc gat cat ttg ttt ttc ttc cgt tta     1344
Arg Ser Ile Ser Leu Lys Cys Leu Asp His Leu Phe Phe Phe Arg Leu
            435                 440                 445 ata ggc gaa aga gca ttg gag gaa tta att gct gag caa ttg gaa gct     1392
Ile Gly Glu Arg Ala Leu Glu Glu Leu Ile Ala Glu Gln Leu Glu Ala
450                 455                 460 cct atc tgc                                                         1401
Pro Ile Cys
465
```

<210> SEQ ID NO 4
<211> LENGTH: 467
<212> TYPE: PRT
<213> ORGANISM: Lucilia cuprina

<400> SEQUENCE: 4

```
Met Asp Asn Gly Glu Gln Asp Ala Gly Phe Arg Leu Ala Pro Met Ser
1               5                   10                  15
```

-continued

```
Pro Gln Glu Ile Lys Pro Asp Ile Ser Leu Leu Asn Glu Asn Asn Thr
             20                  25                  30

Ser Ser Tyr Ser Pro Lys Pro Gly Ser Pro Asn Pro Phe Ala Ile Gly
         35                  40                  45

Leu Gln Ala Ile Asn Ala Val Ala Ala Asn Ala Asn Asn Gln Asn
     50                  55                  60

Gln Met Leu Gln Thr Thr Pro Pro Gln Gln Gln Tyr Pro Pro Asn
 65              70                  75                  80

His Pro Leu Ser Gly Ser Lys His Leu Cys Ser Ile Cys Gly Asp Arg
                 85                  90                  95

Ala Ser Gly Lys His Tyr Gly Val Tyr Ser Cys Glu Gly Cys Lys Gly
            100                 105                 110

Phe Phe Lys Arg Thr Val Arg Lys Asp Leu Thr Tyr Ala Cys Arg Glu
            115                 120                 125

Asp Arg Asn Cys Ile Ile Asp Lys Arg Gln Arg Asn Arg Cys Gln Tyr
        130                 135                 140

Cys Arg Tyr Gln Lys Cys Leu Ala Cys Gly Met Lys Arg Glu Ala Val
145                 150                 155                 160

Gln Glu Glu Arg Gln Arg Gly Thr Arg Ala Ala Asn Ala Arg Ala Ala
                165                 170                 175

Gly Ala Gly Gly Gly Gly Gly Gly Gly Val Ser Asn Val Val
            180                 185                 190

Gly Ala Gly Gly Glu Asp Phe Lys Pro Ser Ser Ser Leu Arg Asp Leu
        195                 200                 205

Thr Ile Glu Arg Ile Ile Glu Ala Glu Gln Lys Ala Glu Ser Leu Ser
    210                 215                 220

Gly Asp Asn Val Leu Pro Phe Leu Arg Val Gly Asn Asn Ser Met Val
225                 230                 235                 240

Gln His Asp Tyr Lys Gly Ala Val Ser His Leu Cys Gln Met Val Asn
                245                 250                 255

Lys Gln Leu Tyr Gln Met Val Glu Tyr Ala Arg Arg Thr Pro His Phe
            260                 265                 270

Thr His Leu Gln Arg Glu Asp Gln Ile Leu Leu Leu Lys Ala Gly Trp
        275                 280                 285

Asn Glu Leu Leu Ile Ala Asn Val Ala Trp Cys Ser Ile Glu Ser Leu
290                 295                 300

Asp Ala Glu Tyr Ala Ser Pro Gly Thr Val His Asp Gly Ser Phe Gly
305                 310                 315                 320

Arg Arg Ser Pro Val Arg Gln Pro Gln Gln Leu Phe Leu Asn Gln Asn
                325                 330                 335

Phe Ser Tyr His Arg Asn Ser Ala Ile Lys Ala Asn Val Val Ser Ile
            340                 345                 350

Phe Asp Arg Ile Leu Ser Glu Leu Ser Ile Lys Met Lys Arg Leu Asn
        355                 360                 365

Ile Asp Arg Ser Glu Leu Ser Cys Leu Lys Ala Ile Ile Leu Phe Asn
    370                 375                 380

Pro Asp Ile Arg Gly Leu Lys Cys Arg Ala Asp Val Glu Val Cys Arg
385                 390                 395                 400

Glu Lys Ile Tyr Ala Cys Leu Asp Glu His Cys Arg Thr Glu His Pro
                405                 410                 415

Gly Asp Asp Gly Arg Phe Ala Gln Leu Leu Leu Arg Leu Pro Ala Leu
            420                 425                 430
```

```
Arg Ser Ile Ser Leu Lys Cys Leu Asp His Leu Phe Phe Arg Leu
        435                 440                 445

Ile Gly Glu Arg Ala Leu Glu Glu Leu Ile Ala Glu Gln Leu Glu Ala
450                 455                 460

Pro Ile Cys
465

<210> SEQ ID NO 5
<211> LENGTH: 585
<212> TYPE: DNA
<213> ORGANISM: Myzus persicae
<220> FEATURE:
<221> NAME/KEY: CDS
<222> LOCATION: (1)..(585)

<400> SEQUENCE: 5 gaa ttc ggc acg agc gcc att gtt aat gga ttt atc cgc acc att agt    48
Glu Phe Gly Thr Ser Ala Ile Val Asn Gly Phe Ile Arg Thr Ile Ser
  1               5                  10                  15 ttg atc ctt att ttt ctt ctt ctt ttt ctt tgg agg ttg ttg gcc ttc    96
Leu Ile Leu Ile Phe Leu Leu Leu Phe Leu Trp Arg Leu Leu Ala Phe
                 20                  25                  30 cgg ttc ttg ttt ata tct gaa caa cca cct ccc gaa gag ctg tgc ctg   144
Arg Phe Leu Phe Ile Ser Glu Gln Pro Pro Pro Glu Glu Leu Cys Leu
             35                  40                  45 gtg tgt ggc gac cgg tcg tcc ggt tac cat tac aac gct ctc aca tgc   192
Val Cys Gly Asp Arg Ser Ser Gly Tyr His Tyr Asn Ala Leu Thr Cys
 50                  55                  60 gaa gga tgc aag ggg ttc ttc cgg agg agc atc acc aag aac gcc gtg   240
Glu Gly Cys Lys Gly Phe Phe Arg Arg Ser Ile Thr Lys Asn Ala Val
 65                  70                  75                  80 tac cag tgc aag tac ggc aac aat tgc gaa atc gac atg tac atg agg   288
Tyr Gln Cys Lys Tyr Gly Asn Asn Cys Glu Ile Asp Met Tyr Met Arg
                 85                  90                  95 cgg aag tgc cag gag tgc cgg ctg aaa aaa tgc ctg acc gtc ggc atg   336
Arg Lys Cys Gln Glu Cys Arg Leu Lys Lys Cys Leu Thr Val Gly Met
            100                 105                 110 agg cct gaa tgt gtt gta cct gaa gtt caa tgc gca gta aaa aga aag   384
Arg Pro Glu Cys Val Val Pro Glu Val Gln Cys Ala Val Lys Arg Lys
        115                 120                 125 gag aaa aaa gct caa cga gaa aaa gat aaa cca aat tct act aca gac   432
Glu Lys Lys Ala Gln Arg Glu Lys Asp Lys Pro Asn Ser Thr Thr Asp
    130                 135                 140 att tct cct gaa ata ata aaa ata gaa cct aca gag atg aag att gaa   480
Ile Ser Pro Glu Ile Ile Lys Ile Glu Pro Thr Glu Met Lys Ile Glu
145                 150                 155                 160 tgt ggt gaa cca atg ata atg ggc aca cct atg ccg act gta cct tac   528
Cys Gly Glu Pro Met Ile Met Gly Thr Pro Met Pro Thr Val Pro Tyr
                165                 170                 175 gtg aaa cct ttg agt tct ctc gtg ccg aat tcg gca cga gtc acg ggt   576
Val Lys Pro Leu Ser Ser Leu Val Pro Asn Ser Ala Arg Val Thr Gly
            180                 185                 190 tac aaa ttt                                                       585
Tyr Lys Phe
        195

<210> SEQ ID NO 6
<211> LENGTH: 195
<212> TYPE: PRT
<213> ORGANISM: Myzus persicae

<400> SEQUENCE: 6
```

```
Glu Phe Gly Thr Ser Ala Ile Val Asn Gly Phe Ile Arg Thr Ile Ser
 1               5                  10                  15

Leu Ile Leu Ile Phe Leu Leu Phe Leu Trp Arg Leu Leu Ala Phe
                20                  25                  30

Arg Phe Leu Phe Ile Ser Glu Gln Pro Pro Glu Glu Leu Cys Leu
             35                  40                  45

Val Cys Gly Asp Arg Ser Gly Tyr His Tyr Asn Ala Leu Thr Cys
     50                  55                  60

Glu Gly Cys Lys Gly Phe Phe Arg Arg Ser Ile Thr Lys Asn Ala Val
 65                  70                  75                  80

Tyr Gln Cys Lys Tyr Gly Asn Asn Cys Glu Ile Asp Met Tyr Met Arg
                 85                  90                  95

Arg Lys Cys Gln Glu Cys Arg Leu Lys Lys Cys Leu Thr Val Gly Met
                100                 105                 110

Arg Pro Glu Cys Val Val Pro Glu Val Gln Cys Ala Val Lys Arg Lys
                115                 120                 125

Glu Lys Lys Ala Gln Arg Glu Lys Asp Lys Pro Asn Ser Thr Thr Asp
130                 135                 140

Ile Ser Pro Glu Ile Ile Lys Ile Glu Pro Thr Glu Met Lys Ile Glu
145                 150                 155                 160

Cys Gly Glu Pro Met Ile Met Gly Thr Pro Met Pro Thr Val Pro Tyr
                165                 170                 175

Val Lys Pro Leu Ser Ser Leu Val Pro Asn Ser Ala Arg Val Thr Gly
                180                 185                 190

Tyr Lys Phe
       195

<210> SEQ ID NO 7
<211> LENGTH: 208
<212> TYPE: DNA
<213> ORGANISM: Myzus persicae

<400> SEQUENCE: 7
catgcctgca ggtcgactct agaggatccc ctcgtccggt taccattaca acgcactcac    60
ctgtgaaggc tgtaagggtt tctttcgacg gagtgttacc aaaaatgcgg tgtattgttg   120
taaatttggt catgcctgcg aaatggacat gtatatgcga cgtaaatgtc aggaatgtag   180
gctgaaaaaa tgtttggctg tgggcatg                                      208

<210> SEQ ID NO 8
<211> LENGTH: 436
<212> TYPE: DNA
<213> ORGANISM: Myzus persicae

<400> SEQUENCE: 8
catgcggccg gaatgtgtgg tgcccgaaaa ccagtgtgca atgaaacgac gcgaaaagaa    60
agcacaaaaa gagaaggata aaatacagac cagtgtgtgt gcaacggaaa ttaaaaagga   120
aatactcgat ttaatgacat gtgaaccgcc atcacatcca acgtgtccgc tgttacctga   180
agacattttg gctaaatgtc aagctcgtaa tatacctcct ttatcgtaca atcaattggc   240
agttatatat aaattaatat ggtatcaaga tggctacgaa cagccatccg aggaagatct   300
caaacgtata atgagttcac ccgatgaaaa tgaaagtcaa cacgatgcat catttcgtca   360
tataacagaa atcactatac taacagtaca attaattgtt gaatgtgcca aaggtctagg   420
gtaccgagct cgaatt                                                   436
```

<210> SEQ ID NO 9
<211> LENGTH: 1797
<212> TYPE: DNA
<213> ORGANISM: Myzus persicae
<220> FEATURE:
<221> NAME/KEY: CDS
<222> LOCATION: (1)..(1797)

<400> SEQUENCE: 9

| | | | | | | | | | | | | | | | | |
|---|---|---|---|---|---|---|---|---|---|---|---|---|---|---|---|---|
| atg | atg | gac | cag | aaa | tgt | gac | gtc | ggc | ggt | ggt | ggt | gtc | gct | gct | gcc | 48 |
| Met | Met | Asp | Gln | Lys | Cys | Asp | Val | Gly | Gly | Gly | Gly | Val | Ala | Ala | Ala | |
| 1 | | | | 5 | | | | | 10 | | | | | 15 | | |
| gcc | gcc | ggt | atc | ggt | ggc | ggc | ggt | gtc | ggc | ggc | ctc | atg | tcg | tac | aac | 96 |
| Ala | Ala | Gly | Ile | Gly | Gly | Gly | Gly | Val | Gly | Gly | Leu | Met | Ser | Tyr | Asn | |
| | | | 20 | | | | | 25 | | | | | 30 | | | |
| cgt | ggc | cgt | ggc | ggc | acc | gag | gtc | atc | atc | aaa | ccc | cgt | agt | cct | gcc | 144 |
| Arg | Gly | Arg | Gly | Gly | Thr | Glu | Val | Ile | Ile | Lys | Pro | Arg | Ser | Pro | Ala | |
| | 35 | | | | | 40 | | | | | 45 | | | | | |
| gtg | gtg | cag | gtg | gcc | acc | ggt | ggc | agt | tac | cac | ggc | ctg | ccg | gcg | gcc | 192 |
| Val | Val | Gln | Val | Ala | Thr | Gly | Gly | Ser | Tyr | His | Gly | Leu | Pro | Ala | Ala | |
| 50 | | | | | 55 | | | | | 60 | | | | | | |
| tcc | gac | gcc | gtc | atc | gtg | cgc | agc | ccg | cca | ggc | ggc | cac | ttg | ccc | ggg | 240 |
| Ser | Asp | Ala | Val | Ile | Val | Arg | Ser | Pro | Pro | Gly | Gly | His | Leu | Pro | Gly | |
| 65 | | | | | 70 | | | | | 75 | | | | | 80 | |
| ccg | cag | cag | caa | gtg | ccg | ccg | tcc | cgc | aac | ggc | tgt | tcc | acc | ctg | ttt | 288 |
| Pro | Gln | Gln | Gln | Val | Pro | Pro | Ser | Arg | Asn | Gly | Cys | Ser | Thr | Leu | Phe | |
| | | | | 85 | | | | | 90 | | | | | 95 | | |
| agc | gac | atc | gct | ggc | gtc | aag | cga | ctc | agg | ccc | gac | gat | tgg | ttg | gcc | 336 |
| Ser | Asp | Ile | Ala | Gly | Val | Lys | Arg | Leu | Arg | Pro | Asp | Asp | Trp | Leu | Ala | |
| | | | 100 | | | | | 105 | | | | | 110 | | | |
| gtc | aac | tcg | ccg | ccc | gcc | tct | tcg | ccc | ggc | acg | tcg | cac | ata | tcc | tac | 384 |
| Val | Asn | Ser | Pro | Pro | Ala | Ser | Ser | Pro | Gly | Thr | Ser | His | Ile | Ser | Tyr | |
| | | 115 | | | | | 120 | | | | | 125 | | | | |
| aca | gtc | ata | tcg | aac | ggc | ggc | ggc | ggt | ggc | ggc | ggt | ggc | ggc | ggt | ggt | 432 |
| Thr | Val | Ile | Ser | Asn | Gly | Gly | Gly | Gly | Gly | Gly | Gly | Gly | Gly | Gly | Gly | |
| | 130 | | | | | 135 | | | | | 140 | | | | | |
| tac | aac | acg | tct | cca | atg | tcg | acc | aac | agc | tac | gac | ccg | tac | agt | ccg | 480 |
| Tyr | Asn | Thr | Ser | Pro | Met | Ser | Thr | Asn | Ser | Tyr | Asp | Pro | Tyr | Ser | Pro | |
| 145 | | | | | 150 | | | | | 155 | | | | | 160 | |
| atg | agt | gga | aaa | atc | gtc | aaa | gaa | gag | ttg | tct | ccg | cca | aac | agc | ctg | 528 |
| Met | Ser | Gly | Lys | Ile | Val | Lys | Glu | Glu | Leu | Ser | Pro | Pro | Asn | Ser | Leu | |
| | | | | 165 | | | | | 170 | | | | | 175 | | |
| tcg | gga | gtc | agc | agc | cat | tcg | gat | ggg | ttg | aag | aag | aag | aaa | ctc | aac | 576 |
| Ser | Gly | Val | Ser | Ser | His | Ser | Asp | Gly | Leu | Lys | Lys | Lys | Lys | Leu | Asn | |
| | | | 180 | | | | | 185 | | | | | 190 | | | |
| cac | acg | ccc | tcg | acc | ggt | gtc | gtc | aac | acc | tcg | gca | tcg | ggc | ccc | ggg | 624 |
| His | Thr | Pro | Ser | Thr | Gly | Val | Val | Asn | Thr | Ser | Ala | Ser | Gly | Pro | Gly | |
| | | 195 | | | | | 200 | | | | | 205 | | | | |
| ggt | ggc | gtt | ggt | ggc | aat | gtg | ctg | aac | aac | cga | cct | ccc | gaa | gag | ctg | 672 |
| Gly | Gly | Val | Gly | Gly | Asn | Val | Leu | Asn | Asn | Arg | Pro | Pro | Glu | Glu | Leu | |
| | 210 | | | | | 215 | | | | | 220 | | | | | |
| tgc | ctg | gtg | tgt | ggc | gac | cgg | tcg | tcc | ggt | tac | cat | tac | aac | gct | ctc | 720 |
| Cys | Leu | Val | Cys | Gly | Asp | Arg | Ser | Ser | Gly | Tyr | His | Tyr | Asn | Ala | Leu | |
| 225 | | | | | 230 | | | | | 235 | | | | | 240 | |
| aca | tgt | gaa | gga | tgc | aag | ggg | ttc | ttc | cgg | agg | agc | atc | acc | aag | aac | 768 |
| Thr | Cys | Glu | Gly | Cys | Lys | Gly | Phe | Phe | Arg | Arg | Ser | Ile | Thr | Lys | Asn | |
| | | | | 245 | | | | | 250 | | | | | 255 | | |
| gcc | gtg | tac | cag | tgc | aag | tac | ggc | aac | aat | tgc | gaa | atc | gac | atg | tac | 816 |
| Ala | Val | Tyr | Gln | Cys | Lys | Tyr | Gly | Asn | Asn | Cys | Glu | Ile | Asp | Met | Tyr | |
| | | | 260 | | | | | 265 | | | | | 270 | | | |

-continued

| | |
|---|---|
| atg agg cgg aag tgc cag gag tgc cgg ctg aaa aaa tgc ctg acc gtc<br>Met Arg Arg Lys Cys Gln Glu Cys Arg Leu Lys Lys Cys Leu Thr Val<br>275              280             285 | 864 |
| ggc atg agg cct gaa tgt gtt gta cct gaa gtt caa tgc gca gta aaa<br>Gly Met Arg Pro Glu Cys Val Val Pro Glu Val Gln Cys Ala Val Lys<br>290              295             300 | 912 |
| aga aag gag aaa aaa gct caa cga gaa aaa gat aaa cca aat tct act<br>Arg Lys Glu Lys Lys Ala Gln Arg Glu Lys Asp Lys Pro Asn Ser Thr<br>305            310            315            320 | 960 |
| aca gac att tct cct gaa ata ata aaa ata gaa cct aca gag atg aag<br>Thr Asp Ile Ser Pro Glu Ile Ile Lys Ile Glu Pro Thr Glu Met Lys<br>325            330            335 | 1008 |
| att gaa tgt ggt gaa cca atg ata atg ggc aca cct atg ccg act gta<br>Ile Glu Cys Gly Glu Pro Met Ile Met Gly Thr Pro Met Pro Thr Val<br>340            345            350 | 1056 |
| cct tac gtg aaa cct ttg agt tct gaa caa aaa gaa ctg atc cac cga<br>Pro Tyr Val Lys Pro Leu Ser Ser Glu Gln Lys Glu Leu Ile His Arg<br>355            360            365 | 1104 |
| ctt gtc tat ttc cag gat caa tat gaa gct cct agt gaa aaa gac atg<br>Leu Val Tyr Phe Gln Asp Gln Tyr Glu Ala Pro Ser Glu Lys Asp Met<br>370            375            380 | 1152 |
| aaa cgt tta aca ata aat aat caa aat atg gat gaa tat gat gaa gaa<br>Lys Arg Leu Thr Ile Asn Asn Gln Asn Met Asp Glu Tyr Asp Glu Glu<br>385            390            395            400 | 1200 |
| aaa caa agt gac acc aca tat cga atc atc act gag atg aca ata ctc<br>Lys Gln Ser Asp Thr Thr Tyr Arg Ile Ile Thr Glu Met Thr Ile Leu<br>405            410            415 | 1248 |
| aca gtt caa ctg att gtt gag ttt gcc aaa cga tta cca ggt ttc gat<br>Thr Val Gln Leu Ile Val Glu Phe Ala Lys Arg Leu Pro Gly Phe Asp<br>420            425            430 | 1296 |
| aaa ctt gta aga gaa gat caa atc act tta ctc aag gct tgc tca agt<br>Lys Leu Val Arg Glu Asp Gln Ile Thr Leu Leu Lys Ala Cys Ser Ser<br>435            440            445 | 1344 |
| gaa gct atg atg ttc agg gta gca agg aag tat gac atc acc act gac<br>Glu Ala Met Met Phe Arg Val Ala Arg Lys Tyr Asp Ile Thr Thr Asp<br>450            455            460 | 1392 |
| tca ata gtg ttt gct aac aac cag cca ttt tca gct gat tca tat aac<br>Ser Ile Val Phe Ala Asn Asn Gln Pro Phe Ser Ala Asp Ser Tyr Asn<br>465            470            475            480 | 1440 |
| aaa gct gga ttg gga gat gcc att gaa aac caa ctg tca ttc agt cgg<br>Lys Ala Gly Leu Gly Asp Ala Ile Glu Asn Gln Leu Ser Phe Ser Arg<br>485            490            495 | 1488 |
| ttt atg tac aat atg aag gtg gat aac gca gaa tat gcc tta ttg acc<br>Phe Met Tyr Asn Met Lys Val Asp Asn Ala Glu Tyr Ala Leu Leu Thr<br>500            505            510 | 1536 |
| gcc atc gtc ata ttt tcg agt agg cca aat tta cta gat ggt tgg aaa<br>Ala Ile Val Ile Phe Ser Ser Arg Pro Asn Leu Leu Asp Gly Trp Lys<br>515            520            525 | 1584 |
| gtg gag aaa atc caa gaa atc tac cta gag tcc tta aaa gct tat gta<br>Val Glu Lys Ile Gln Glu Ile Tyr Leu Glu Ser Leu Lys Ala Tyr Val<br>530            535            540 | 1632 |
| gat aat cga gac cgt gac aca gca act gta cga tat gcg cga ctt ctc<br>Asp Asn Arg Asp Arg Asp Thr Ala Thr Val Arg Tyr Ala Arg Leu Leu<br>545            550            555            560 | 1680 |
| tca gta ctt aca gaa ttg cgc aca tta ggc aat gaa aac tct gag cta<br>Ser Val Leu Thr Glu Leu Arg Thr Leu Gly Asn Glu Asn Ser Glu Leu<br>565            570            575 | 1728 |
| tgt atg aca ctg aaa ctg aaa aac aga gta gta ccc cca ttc ttg gcc<br>Cys Met Thr Leu Lys Leu Lys Asn Arg Val Val Pro Pro Phe Leu Ala | 1776 |

```
                580             585             590
gaa ata tgg gat gtc atg cca                              1797
Glu Ile Trp Asp Val Met Pro
    595
```

<210> SEQ ID NO 10
<211> LENGTH: 599
<212> TYPE: PRT
<213> ORGANISM: Myzus persicae

<400> SEQUENCE: 10

```
Met Met Asp Gln Lys Cys Asp Val Gly Gly Gly Val Ala Ala Ala
 1               5                  10                  15

Ala Ala Gly Ile Gly Gly Gly Val Gly Gly Leu Met Ser Tyr Asn
                20                  25                  30

Arg Gly Arg Gly Gly Thr Glu Val Ile Ile Lys Pro Arg Ser Pro Ala
         35                  40                  45

Val Val Gln Val Ala Thr Gly Gly Ser Tyr His Gly Leu Pro Ala Ala
     50                  55                  60

Ser Asp Ala Val Ile Val Arg Ser Pro Pro Gly Gly His Leu Pro Gly
 65                  70                  75                  80

Pro Gln Gln Gln Val Pro Pro Ser Arg Asn Gly Cys Ser Thr Leu Phe
                85                  90                  95

Ser Asp Ile Ala Gly Val Lys Arg Leu Arg Pro Asp Asp Trp Leu Ala
            100                 105                 110

Val Asn Ser Pro Pro Ala Ser Ser Pro Gly Thr Ser His Ile Ser Tyr
        115                 120                 125

Thr Val Ile Ser Asn Gly Gly Gly Gly Gly Gly Gly Gly Gly
    130                 135                 140

Tyr Asn Thr Ser Pro Met Ser Thr Asn Ser Tyr Asp Pro Tyr Ser Pro
145                 150                 155                 160

Met Ser Gly Lys Ile Val Lys Glu Glu Leu Ser Pro Pro Asn Ser Leu
                165                 170                 175

Ser Gly Val Ser Ser His Ser Asp Gly Leu Lys Lys Lys Leu Asn
            180                 185                 190

His Thr Pro Ser Thr Gly Val Val Asn Thr Ser Ala Ser Gly Pro Gly
        195                 200                 205

Gly Gly Val Gly Gly Asn Val Leu Asn Asn Arg Pro Pro Glu Glu Leu
    210                 215                 220

Cys Leu Val Cys Gly Asp Arg Ser Ser Gly Tyr His Tyr Asn Ala Leu
225                 230                 235                 240

Thr Cys Glu Gly Cys Lys Gly Phe Phe Arg Arg Ser Ile Thr Lys Asn
                245                 250                 255

Ala Val Tyr Gln Cys Lys Tyr Gly Asn Asn Cys Glu Ile Asp Met Tyr
            260                 265                 270

Met Arg Arg Lys Cys Gln Glu Cys Arg Leu Lys Lys Cys Leu Thr Val
        275                 280                 285

Gly Met Arg Pro Glu Cys Val Val Pro Glu Val Gln Cys Ala Val Lys
    290                 295                 300

Arg Lys Glu Lys Lys Ala Gln Arg Glu Lys Asp Lys Pro Asn Ser Thr
305                 310                 315                 320

Thr Asp Ile Ser Pro Glu Ile Ile Lys Ile Glu Pro Thr Glu Met Lys
                325                 330                 335

Ile Glu Cys Gly Glu Pro Met Ile Met Gly Thr Pro Met Pro Thr Val
            340                 345                 350
```

```
Pro Tyr Val Lys Pro Leu Ser Ser Glu Gln Lys Glu Leu Ile His Arg
        355                 360                 365

Leu Val Tyr Phe Gln Asp Gln Tyr Glu Ala Pro Ser Glu Lys Asp Met
        370                 375                 380

Lys Arg Leu Thr Ile Asn Asn Gln Asn Met Asp Glu Tyr Asp Glu Glu
385                 390                 395                 400

Lys Gln Ser Asp Thr Thr Tyr Arg Ile Ile Thr Glu Met Thr Ile Leu
                405                 410                 415

Thr Val Gln Leu Ile Val Glu Phe Ala Lys Arg Leu Pro Gly Phe Asp
                420                 425                 430

Lys Leu Val Arg Glu Asp Gln Ile Thr Leu Leu Lys Ala Cys Ser Ser
        435                 440                 445

Glu Ala Met Met Phe Arg Val Ala Arg Lys Tyr Asp Ile Thr Thr Asp
        450                 455                 460

Ser Ile Val Phe Ala Asn Asn Gln Pro Phe Ser Ala Asp Ser Tyr Asn
465                 470                 475                 480

Lys Ala Gly Leu Gly Asp Ala Ile Glu Asn Gln Leu Ser Phe Ser Arg
                485                 490                 495

Phe Met Tyr Asn Met Lys Val Asp Asn Ala Glu Tyr Ala Leu Leu Thr
                500                 505                 510

Ala Ile Val Ile Phe Ser Ser Arg Pro Asn Leu Leu Asp Gly Trp Lys
        515                 520                 525

Val Glu Lys Ile Gln Glu Ile Tyr Leu Glu Ser Leu Lys Ala Tyr Val
        530                 535                 540

Asp Asn Arg Asp Arg Asp Thr Ala Thr Val Arg Tyr Ala Arg Leu Leu
545                 550                 555                 560

Ser Val Leu Thr Glu Leu Arg Thr Leu Gly Asn Glu Asn Ser Glu Leu
                565                 570                 575

Cys Met Thr Leu Lys Leu Lys Asn Arg Val Val Pro Pro Phe Leu Ala
                580                 585                 590

Glu Ile Trp Asp Val Met Pro
        595

<210> SEQ ID NO 11
<211> LENGTH: 1131
<212> TYPE: DNA
<213> ORGANISM: Myzus persicae
<220> FEATURE:
<221> NAME/KEY: CDS
<222> LOCATION: (1)..(1131)

<400> SEQUENCE: 11 atg tat tcc aac tcg tac acc atg tat tca agt gac aga tta tac agc     48
Met Tyr Ser Asn Ser Tyr Thr Met Tyr Ser Ser Asp Arg Leu Tyr Ser
 1               5                  10                  15 gtc gat cgg aac agt atg atg aat aat tct tgc aac gta caa gac tct     96
Val Asp Arg Asn Ser Met Met Asn Asn Ser Cys Asn Val Gln Asp Ser
            20                  25                  30 ccg aat tac ccg ccc aac cat cca ctc agc ggt tcg aaa cat ctg tgc    144
Pro Asn Tyr Pro Pro Asn His Pro Leu Ser Gly Ser Lys His Leu Cys
        35                  40                  45 tcc ata tgc ggc gat cgc gcc agt gga aaa cat tac gga gtc tac agc    192
Ser Ile Cys Gly Asp Arg Ala Ser Gly Lys His Tyr Gly Val Tyr Ser
    50                  55                  60 tgc gag ggg tgc aaa ggg ttc ttc aaa cgc aca gtg agg aaa aat ttg    240
Cys Glu Gly Cys Lys Gly Phe Phe Lys Arg Thr Val Arg Lys Asn Leu
65                  70                  75                  80
```

```
tca tac gcg tgt cgc gaa gaa aac aaa tgc atc atc gac aag cgc caa       288
Ser Tyr Ala Cys Arg Glu Glu Asn Lys Cys Ile Ile Asp Lys Arg Gln
             85                  90                  95 cga aat cgg tgc caa tac tgc agg tat caa aaa tgt ttg acc atg ggc       336
Arg Asn Arg Cys Gln Tyr Cys Arg Tyr Gln Lys Cys Leu Thr Met Gly
        100                 105                 110 atg aaa aga gaa gct gtg cag gaa gaa aga caa cgt aca aaa gaa cga       384
Met Lys Arg Glu Ala Val Gln Glu Glu Arg Gln Arg Thr Lys Glu Arg
            115                 120                 125 gat cat aat aac atc gaa gtt gaa ccc acg agc agt tct aat act gat       432
Asp His Asn Asn Ile Glu Val Glu Pro Thr Ser Ser Ser Asn Thr Asp
        130                 135                 140 atg cca gtg gaa ctc ata tta agg gct gag aat aaa gct gat gct ata       480
Met Pro Val Glu Leu Ile Leu Arg Ala Glu Asn Lys Ala Asp Ala Ile
145                 150                 155                 160 aag act gaa caa cag tat ata gag caa cga cat cct caa cat act gtt       528
Lys Thr Glu Gln Gln Tyr Ile Glu Gln Arg His Pro Gln His Thr Val
                165                 170                 175 ggt gct att tgt caa gca act gac aag cag tta ata caa ctt gtt gaa       576
Gly Ala Ile Cys Gln Ala Thr Asp Lys Gln Leu Ile Gln Leu Val Glu
            180                 185                 190 tgg gcc aag cat ata ccg cat ttt aaa aat tta cct cta ggc gat caa       624
Trp Ala Lys His Ile Pro His Phe Lys Asn Leu Pro Leu Gly Asp Gln
        195                 200                 205 gtt tta tta ttg aga gct ggt tgg aat gag ttg atg att gca gca ttt       672
Val Leu Leu Leu Arg Ala Gly Trp Asn Glu Leu Met Ile Ala Ala Phe
    210                 215                 220 tcc cat aga tca atc agt gta aaa gat ggt ata gtc tta gct act gga       720
Ser His Arg Ser Ile Ser Val Lys Asp Gly Ile Val Leu Ala Thr Gly
225                 230                 235                 240 ctt act gtt gac aga gat tca gct cac caa gct ggt gtt gaa gct ata       768
Leu Thr Val Asp Arg Asp Ser Ala His Gln Ala Gly Val Glu Ala Ile
                245                 250                 255 ttt gat cgt gta ctc act gaa ctc gtt gct aaa atg aga gat atg ggt       816
Phe Asp Arg Val Leu Thr Glu Leu Val Ala Lys Met Arg Asp Met Gly
            260                 265                 270 atg gat aga aca gag ctt ggc tgt ttg cgt act att att ctt ttt aat       864
Met Asp Arg Thr Glu Leu Gly Cys Leu Arg Thr Ile Ile Leu Phe Asn
        275                 280                 285 cca ggt tca aaa ggt ttg cag tct gtg aat gaa gtg caa gta ctg cgt       912
Pro Gly Ser Lys Gly Leu Gln Ser Val Asn Glu Val Gln Val Leu Arg
    290                 295                 300 gat aag gtt tat gtt gcg tta gaa gaa tat tgt cgt aca aca cat cca       960
Asp Lys Val Tyr Val Ala Leu Glu Glu Tyr Cys Arg Thr Thr His Pro
305                 310                 315                 320 gaa gaa cct gga cga ttt gct aaa cta ctt ctt cgg ctt cct tca tta      1008
Glu Glu Pro Gly Arg Phe Ala Lys Leu Leu Leu Arg Leu Pro Ser Leu
                325                 330                 335 cgt tca att gga tta aaa tgt ctg gaa cat tta ttc ttt tat aaa ctt      1056
Arg Ser Ile Gly Leu Lys Cys Leu Glu His Leu Phe Phe Tyr Lys Leu
            340                 345                 350 att ggc gat tcc cca att gat aca ttt tta atg gaa gtt ctc gaa tca      1104
Ile Gly Asp Ser Pro Ile Asp Thr Phe Leu Met Glu Val Leu Glu Ser
        355                 360                 365 tct tca cat gac gtt caa gta gct aca                                  1131
Ser Ser His Asp Val Gln Val Ala Thr
    370                 375

<210> SEQ ID NO 12
```

```
<211> LENGTH: 377
<212> TYPE: PRT
<213> ORGANISM: Myzus persicae

<400> SEQUENCE: 12

Met Tyr Ser Asn Ser Tyr Thr Met Tyr Ser Ser Asp Arg Leu Tyr Ser
 1               5                  10                  15

Val Asp Arg Asn Ser Met Met Asn Asn Ser Cys Asn Val Gln Asp Ser
             20                  25                  30

Pro Asn Tyr Pro Pro Asn His Pro Leu Ser Gly Ser Lys His Leu Cys
         35                  40                  45

Ser Ile Cys Gly Asp Arg Ala Ser Gly Lys His Tyr Gly Val Tyr Ser
     50                  55                  60

Cys Glu Gly Cys Lys Gly Phe Phe Lys Arg Thr Val Arg Lys Asn Leu
 65                  70                  75                  80

Ser Tyr Ala Cys Arg Glu Glu Asn Lys Cys Ile Ile Asp Lys Arg Gln
                 85                  90                  95

Arg Asn Arg Cys Gln Tyr Cys Arg Tyr Gln Lys Cys Leu Thr Met Gly
            100                 105                 110

Met Lys Arg Glu Ala Val Gln Glu Glu Arg Gln Arg Thr Lys Glu Arg
        115                 120                 125

Asp His Asn Asn Ile Glu Val Glu Pro Thr Ser Ser Ser Asn Thr Asp
    130                 135                 140

Met Pro Val Glu Leu Ile Leu Arg Ala Glu Asn Lys Ala Asp Ala Ile
145                 150                 155                 160

Lys Thr Glu Gln Gln Tyr Ile Glu Gln Arg His Pro Gln His Thr Val
                165                 170                 175

Gly Ala Ile Cys Gln Ala Thr Asp Lys Gln Leu Ile Gln Leu Val Glu
            180                 185                 190

Trp Ala Lys His Ile Pro His Phe Lys Asn Leu Pro Leu Gly Asp Gln
        195                 200                 205

Val Leu Leu Leu Arg Ala Gly Trp Asn Glu Leu Met Ile Ala Ala Phe
    210                 215                 220

Ser His Arg Ser Ile Ser Val Lys Asp Gly Ile Val Leu Ala Thr Gly
225                 230                 235                 240

Leu Thr Val Asp Arg Asp Ser Ala His Gln Ala Gly Val Glu Ala Ile
                245                 250                 255

Phe Asp Arg Val Leu Thr Glu Leu Val Ala Lys Met Arg Asp Met Gly
            260                 265                 270

Met Asp Arg Thr Glu Leu Gly Cys Leu Arg Thr Ile Ile Leu Phe Asn
        275                 280                 285

Pro Gly Ser Lys Gly Leu Gln Ser Val Asn Glu Val Gln Val Leu Arg
    290                 295                 300

Asp Lys Val Tyr Val Ala Leu Glu Glu Tyr Cys Arg Thr Thr His Pro
305                 310                 315                 320

Glu Glu Pro Gly Arg Phe Ala Lys Leu Leu Leu Arg Leu Pro Ser Leu
                325                 330                 335

Arg Ser Ile Gly Leu Lys Cys Leu Glu His Leu Phe Phe Tyr Lys Leu
            340                 345                 350

Ile Gly Asp Ser Pro Ile Asp Thr Phe Leu Met Glu Val Leu Glu Ser
        355                 360                 365

Ser Ser His Asp Val Gln Val Ala Thr
    370                 375
```

```
<210> SEQ ID NO 13
<211> LENGTH: 150
<212> TYPE: DNA
<213> ORGANISM: Lucilia cuprina
<220> FEATURE:
<221> NAME/KEY: CDS
<222> LOCATION: (9)..(134)

<400> SEQUENCE: 13 aattctgc gaa gga tgc aag gga ttc ttc aaa cgt acc gta cgc aag gac        50
         Glu Gly Cys Lys Gly Phe Phe Lys Arg Thr Val Arg Lys Asp
          1               5                  10 ttg aca tat gct tgt cgt gag gac aga aat tgc att ata gat aaa cga         98
Leu Thr Tyr Ala Cys Arg Glu Asp Arg Asn Cys Ile Ile Asp Lys Arg
 15              20                  25                  30 caa aga aat cgt tgc cag tat tgt cgc tac caa aag tgatcgatac cgtcga      150
Gln Arg Asn Arg Cys Gln Tyr Cys Arg Tyr Gln Lys
                 35                  40

<210> SEQ ID NO 14
<211> LENGTH: 42
<212> TYPE: PRT
<213> ORGANISM: Lucilia cuprina

<400> SEQUENCE: 14

Glu Gly Cys Lys Gly Phe Phe Lys Arg Thr Val Arg Lys Asp Leu Thr
 1               5                  10                  15

Tyr Ala Cys Arg Glu Asp Arg Asn Cys Ile Ile Asp Lys Arg Gln Arg
                 20                  25                  30

Asn Arg Cys Gln Tyr Cys Arg Tyr Gln Lys
         35                  40

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:
      oligonucleotide useful as primer.
<221> NAME/KEY: misc_feature
<222> LOCATION: (1)..(32)
<223> OTHER INFORMATION: Nucleotides designated as "n" residues can be
      A, G, C or T residues.

<400> SEQUENCE: 15
cggaattccg cctcnggnta ycaytayaay gc                                      32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide useful as primer.

<400> SEQUENCE: 16
cgcggatccr cactcctgac actttcgyct ca                                      32

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide useful as primer.

<400> SEQUENCE: 17
```

```
gcctcggggt atcactataa cgc                                                23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide useful as primer.

<400> SEQUENCE: 18
gcactcctga cactttcgtc tca                                                23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide useful as primer.

<400> SEQUENCE: 19
tcgtccggtt accattacaa cgc                                                23

<210> SEQ ID NO 20
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Nucleotides designated as "n" residues can be
      A, G, C or T residues.

<400> SEQUENCE: 20
tagacctttg gcraaytcna caat                                               24
```

GENETIC SEQUENCES ENCODING STEROID AND JUVENILE HORMONE RECEPTOR POLYPEPTIDES AND INSECTICIDAL MODALITIES THEREFOR

This application is a continuation-in-part of Australian application PP1356/98 filed 15 Jan. 1998 and PCT application PCT/AU99/00033 filed 15 Jan. 1999, both incorporated herein by reference to the extent that there is no inconsistency with the present disclosure.

FIELD OF THE INVENTION

The present invention relates generally to novel genetic sequences encoding receptor polypeptides and insecticidal modalities therefor, which insecticidal modalities are based upon non-polypeptide insect hormones and their receptors. More specifically, the present invention provides isolated nucleic acid molecules encoding polypeptides comprising functional steroid hormone and juvenile hormone receptors, in particular isolated nucleic acid molecules which encode polypeptides comprising the *Lucilia cuprina* and *Myzus persicae* ecdysone receptors and juvenile hormone receptors. In a particularly preferred embodiment, the present invention relates to isolated nucleic acid molecules which encode the *L. cuprina* and *M. persicae* EcR polypeptide subunits and EcR partner protein (USP polypeptide) subunits which form functional heterodimeric ecdysone receptor, and to the *L. cuprina* and *M. persicae* USP polypeptide of the juvenile hormone receptor. The present invention further relates to the production of functional recombinant insect receptors and recombinant polypeptide subunits thereof and derivatives and analogues thereof. The present invention further relates to the uses of the recombinant receptor and isolated nucleic acid molecules of the present invention in the regulation of gene expression. The present invention further relates to screening systems and methods of identifying insecticidally-active agents which are capable of agonising or antagonising insect receptor function, such as molecules and/or ligands which associate with steroid receptors or juvenile hormone receptors so as to modify the affinity of said receptors for their cognate cis-acting response elements (e.g., insect steroid response elements, juvenile hormone response elements) in the genes which they regulate, or alternatively or in addition, which modify the affinity of said receptors for their cellular stimuli (e.g., insect steroids or juvenile hormones) or analogues thereof, or alternatively or in addition, which act as insecticides by virtue of their ability to agonise or antagonise the activity of insect hormones, such as by mimicry of a ligand which binds to said receptor or a ligand-binding region thereof. The invention further extends to such compounds and/or ligands.

This specification contains nucleotide and amino acid sequence information prepared using the program Patentin Version 2.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> and the sequence identifier (eg. SEQ ID NO:1, SEQ ID NO:2, etc).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

Bibliographic details of the publications referred to in this specification are collected at the end of the description.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only. Functionally-equivalent products, compositions and methods are clearly within the scope of the invention, as described herein.

BACKGROUND TO THE INVENTION

International Patent Application No WO91/13167 (applicant, The Board of Trustees of Leyland Stanford University, and hereinafter referred to as WO91/13167) describes the identification, characterization, expression and uses of insect steroid receptors and DNA sequences encoding same and, in particular, the identification, characterization, expression and uses of the steroid receptor of the common fruit fly, *Drosophila melanogaster*.

It has been found by the present inventors that the limited homology between the *D. melanogaster* steroid receptor-encoding gene sequences and the steroid receptor-encoding sequences derived from other insects, in particular those derived from diptera such as the Australian sheep blowfly *L. cuprina*, hemiptera such as aphids, scale insects and leaf hoppers, coleoptera, neuroptera, lepidoptera, and ants, as well as from helminths and protozoa, prevents the routine isolation of DNA sequences encoding steroid receptors and/or juvenile hormone receptors from these latter-mentioned organisms.

Moreover, the present inventors have discovered that the *D. melanogaster* steroid receptor described in WO91/13167 is temperature-sensitive, showing reduced activity at temperatures above 30° C., such as at temperatures about 37° C., particularly at low concentrations of the receptor. Accordingly, the *D. melanogaster* steroid receptor described in WO91/13167 is of limited utility at physiological temperatures applicable to animal or bacterial cells. Moreover, wherein it is desirable to produce a biologically-active steroid receptor using in vivo or in situ expression systems, which expression systems routinely utilise cells or tissues in the temperature range of about 28° C. to about 42° C., the *D. melanogaster* steroid receptor is also of limited utility.

In work leading up to the present invention, the present inventors developed a novel screening protocol, involving the utilisation of highly-degenerate oligonucleotide probes and primers derived from the amino acid sequences of the DNA-binding domains of the *D. melanogaster* and *Chironomus tentans* ecdysone receptor polypeptides, to identify nucleotide sequences encoding novel steroid receptor polypeptides and novel insect juvenile hormone receptor polypeptides. The present inventors have further identified specific regions within these novel polypeptides which are suitable for use in preparing a surprising range of novel steroid receptor polypeptide derivatives and insect juvenile hormone receptor polypeptide derivatives. The novel steroid receptor polypeptides and novel insect juvenile hormone receptor polypeptides of the present invention, and derivative polypeptides thereof, and assembled steroid receptors and insect juvenile hormone receptors derived from said polypeptides and derivatives, and nucleic acid molecules encoding same as exemplified herein, provide the means for developing a wide range of insecticidally-active agents, as well as methods for the regulated production of bioactive molecules. In particular, the present invention provides the means for developing specific ligands which bind to and either agonise or antagonise the steroid receptors and/or juvenile hormone receptors and/or polypeptide subunits thereof as described herein, thereby functioning as highly-specific insecticides, offering significant commercial and environmental benefits.

The present inventors have been surprisingly successful in characterizing the ecdysone receptor and juvenile hormone receptor derived from insects of the orders Diptera and Hemiptera, and polypeptide components thereof and functional derivatives of said polypeptides and receptors, particularly in light of the extreme difficulties in dealing with these organisms. The nature of these molecules was unknown prior to the present invention.

The various aspects of this invention overcome the problems associated with *Drosophila* ecdysone receptors which lack thermal stability. Moreover, those aspects of the invention pertaining to methods of screening for insecticidally active agents do not involve competition assays which are generally complex, and often inaccurate or difficult to calibrate.

SUMMARY OF THE INVENTION

One aspect of the present invention provides an isolated nucleic acid molecule comprising a nucleotide sequence which encodes or is complementary to a sequence which encodes a steroid receptor polypeptide or a juvenile hormone receptor polypeptide or a bioactive derivative or analogue thereof, wherein said polypeptide:
  (i) is selected from the list comprising EcR polypeptide of an steroid receptor, the partner protein (USP polypeptide) of an steroid receptor and the USP polypeptide of a juvenile hormone receptor; and
  (ii) comprises an amino acid sequence that is at least 40% identical to any one of the amino acid sequences set forth in SEQ ID NO:2, SEQ ID NO:4, SEQ ID NO:6, SEQ ID NO:10, SEQ ID NO:12 or SEQ ID NO:14.

In an alternative embodiment, the present invention provides an isolated nucleic acid molecule comprising a nucleotide sequence which encodes or is complementary to a sequence which encodes a steroid receptor polypeptide or a juvenile hormone receptor polypeptide or a bioactive derivative or analogue thereof, wherein said polypeptide:
  (i) is selected from the list comprising EcR polypeptide of an steroid receptor, the partner protein (USP polypeptide) of an steroid receptor and the USP polypeptide of a juvenile hormone receptor; and
  (ii) comprises an amino acid sequence that is at least 40% identical to any one of the amino acid sequences encoded by the plasmids deposited under any one of AGAL Accession Nos. NM99/04565, NM99/04566, NM99/04567, or NM99/04568.

In a further alternative embodiment, the isolated nucleic acid molecule of the present invention comprises a nucleotide sequence which encodes or is complementary to a sequence which encodes a steroid receptor polypeptide or a juvenile hormone receptor polypeptide or a bioactive derivative or analogue thereof, wherein said nucleotide sequence is selected from the list comprising:
  (i) a nucleotide sequence having at least 40% identity to any one of the nucleotide sequences set forth in SEQ ID NO:1, SEQ ID NO:3, SEQ ID NO:5, SEQ ID NO:9, SEQ ID NO:11 or SEQ ID NO:13 or a complementary nucleotide sequence thereto;
  (ii) a nucleotide sequence that is capable of hybridising under at least low stringency conditions to any one of the nucleotide sequences set forth in SEQ ID NO:1, SEQ ID NO:3, SEQ ID NO:5, SEQ ID NO:7, SEQ ID NO:8, SEQ ID NO:9, SEQ ID NO:11 or SEQ ID NO:13 or to a complementary nucleotide sequence thereto;
  (iii) a nucleotide sequence that is capable of hybridising under at least low stringency conditions to a nucleotide sequence contained in any one of the plasmids deposited under AGAL Accession Nos. NM99/04565, NM99/04566, NM99/04567, or NM99/04568;
  (iv) a nucleotide sequence that is at least 40% identical to a nucleotide sequence contained in any one of the plasmids deposited under AGAL Accession Nos. NM99/04565, NM99/04566, NM99/04567, or NM99/04568; and
  (v) a nucleotide sequence that is amplifiable by PCR using a nucleic acid primer sequence set forth in any one of SEQ ID NO:15, SEQ ID NO:16, SEQ ID NO:17, SEQ ID NO:18, SEQ ID NO:19 or SEQ ID NO:20.

In a further alternative embodiment, the present invention provides an isolated nucleic acid molecule which encodes a steroid receptor polypeptide and comprises the nucleotide sequence set forth in SEQ ID NO:1 or a complementary nucleotide sequence thereto.

In a further alternative embodiment, the present invention provides an isolated nucleic acid molecule which encodes a steroid receptor polypeptide or a juvenile hormone receptor polypeptide and comprises the nucleotide sequence set forth in SEQ ID NO:3 or SEQ ID NO:13 or a complementary nucleotide sequence thereto.

In a further alternative embodiment, the present invention provides an isolated nucleic acid molecule which encodes a steroid receptor polypeptide and comprises the nucleotide sequence set forth in SEQ ID NO:5 or SEQ ID NO:7 or SEQ ID NO:8 or SEQ ID NO:9 or a complementary nucleotide sequence thereto.

In a further alternative embodiment, the present invention provides an isolated nucleic acid molecule which encodes a steroid receptor polypeptide or a juvenile hormone receptor polypeptide and comprises the nucleotide sequence set forth in SEQ ID NO:11 or a complementary nucleotide sequence thereto.

A second aspect of the present invention provides a method of identifying an isolated nucleic acid molecule which encodes a steroid receptor polypeptide or a juvenile hormone receptor polypeptide comprising the steps of:
(i) hybridising genomic DNA, mRNA or cDNA with a hybridisation-effective amount of one or more probes selected from the list comprising:
  (a) probes comprising at least 10 contiguous nucleotides in length derived from any one of SEQ ID NO:1, SEQ ID NO:3, SEQ ID NO:5, SEQ ID NO:7, SEQ ID NO:8, SEQ ID NO:9, SEQ ID NO:11, SEQ ID NO:13, SEQ ID NO:15, SEQ ID NO:16, SEQ ID NO:17, SEQ ID NO:18, SEQ ID NO:19 or SEQ ID NO:20 or a complementary nucleotide sequence thereto;
  (b) probes comprising at least 10 contiguous nucleotides in length derived from a cDNA contained in any one of the plasmids deposited under AGAL Accession Nos. NM99/04565, NM99/04566, NM99/04567, or NM99/04568; and
  (c) hybridisation probes comprising the nucleotide sequences set forth in any one of SEQ ID NO:1, SEQ ID NO:3, SEQ ID NO:5, SEQ ID NO:7, SEQ ID NO:8, SEQ ID NO:9, SEQ ID NO:11, or SEQ ID NO:13 or a complementary nucleotide sequence thereto or a homologue, analogue or derivative thereof which is at least 40% identical to said sequence or complement; and
(ii) detecting the hybridisation.

In an alternative embodiment, the inventive method comprises the steps of:
(i) annealing to genomic DNA, mRNA or cDNA, one or more PCR primers comprising at least 10 contiguous nucleotides in length derived from the group consisting of:
  (a) a primer derived from any one of SEQ ID NO:1, SEQ ID NO:3, SEQ ID NO:5, SEQ ID NO:7, SEQ ID NO:8, SEQ ID NO:9, SEQ ID NO:11, SEQ ID NO:13, SEQ ID NO:15, SEQ ID NO:16, SEQ ID NO:17, SEQ ID NO:18, SEQ ID NO:19 or SEQ ID NO:20 or a complementary nucleotide sequence thereto; and
  (b) a primer derived from a cDNA contained in any one of the plasmids deposited under AGAL Accession Nos. NM99/04565, NM99/04566, NM99/04567, or NM99/04568; and
(ii) amplifying a nucleotide sequence which encodes a steroid receptor polypeptide or a juvenile hormone receptor polypeptide in a polymerase chain reaction.

In a further alternative embodiment, the inventive method comprises the steps of:
(i) amplifying a nucleotide sequence which encodes a steroid receptor polypeptide or a juvenile hormone receptor polypeptide in a polymerase chain reaction using one or more PCR primers comprising at least 10 contiguous nucleotides in length from the group consisting of:
  (a) a primer derived from any one of SEQ ID NO:1, SEQ ID NO:3, SEQ ID NO:5, SEQ ID NO:7, SEQ ID NO:8, SEQ ID NO:9, SEQ ID NO:11, SEQ ID NO:13, SEQ ID NO:15, SEQ ID NO:16, SEQ ID NO:17, SEQ ID NO:18, SEQ ID NO:19 or SEQ ID NO:20 or a complementary nucleotide sequence thereto; and
  (b) a primer derived from a cDNA contained in any one of the plasmids deposited under AGAL Accession Nos. NM99/04565, NM99/04566, NM99/04567, or NM99/04568;
(ii) hybridising the amplified nucleotide sequence to genomic DNA, mRNA or cDNA with a hybridisation-effective amount of one or more probes selected from the group consisting of:
  (a) a probe comprising at least 10 contiguous nucleotides in length derived from any one of SEQ ID NO:1, SEQ ID NO:3, SEQ ID NO:5, SEQ ID NO:7, SEQ ID NO:8, SEQ ID NO:9, SEQ ID NO:11, SEQ ID NO:13, SEQ ID NO:15, SEQ ID NO:16, SEQ ID NO:17, SEQ ID NO:18, SEQ ID NO:19 or SEQ ID NO:20 or a complementary nucleotide sequence thereto;
  (b) a probe comprising at least 10 contiguous nucleotides in length derived from a cDNA contained in any one of the plasmids deposited under AGAL Accession Nos. NM99/04565, NM99/04566, NM99/04567, or NM99/04568; and
  (c) hybridisation probes comprising the nucleotide sequences set forth in any one of SEQ ID NO:1, SEQ ID NO:3, SEQ ID NO:5, SEQ ID NO:7, SEQ ID NO:8, SEQ ID NO:9, SEQ ID NO:11, or SEQ ID NO:13 or a complementary nucleotide sequence thereto or a homologue, analogue or derivative thereof which is at least 40% identical to said sequence or complement; and
(iii) detecting the hybridisation.

A third aspect of the present invention provides a genetic construct comprising the subject isolated nucleic acid molecule which encodes a steroid receptor polypeptide or a juvenile hormone receptor polypeptide, operably linked to a promoter sequence. Preferably, the subject nucleic acid molecule is in an expressible format, such that it is possible to produce a recombinant polypeptide therefrom.

Accordingly, a fourth aspect of the invention provides a recombinant or isolated polypeptide comprising a steroid receptor polypeptide or juvenile hormone receptor polypeptide or a bioactive derivative or analogue thereof, wherein said polypeptide:
(i) is selected from the list comprising EcR polypeptide of a steroid receptor, the partner protein (USP polypeptide) of a steroid receptor and the USP polypeptide of a juvenile hormone receptor; and
(ii) comprises an amino acid sequence that is at least 40% identical to any one of the amino acid sequences set forth in SEQ ID NO:2, SEQ ID NO:4, SEQ ID NO:6, SEQ ID NO:10, SEQ ID NO:12 or SEQ ID NO:14;

wherein said polypeptide is substantially free of naturally-associated insect cell components.

In an alternative embodiment, the invention provides a recombinant or isolated polypeptide comprising a steroid receptor polypeptide or juvenile hormone receptor polypeptide or a bioactive derivative or analogue thereof, wherein said polypeptide:
(i) is selected from the list comprising EcR polypeptide of a steroid receptor, the partner protein (USP polypeptide) of a steroid receptor and the USP polypeptide of a juvenile hormone receptor; and
(ii) comprises an amino acid sequence that is at least 40% identical to a polypeptide encoded by the cDNA present in any one of the plasmids deposited under AGAL Accession Nos. NM99/04565, NM99/04566, NM99/04567, or NM99/04568;

wherein said polypeptide is substantially free of naturally-associated insect cell components.

A fifth aspect of the invention provides a cell comprising the subject isolated nucleic acid molecule which encodes a steroid receptor polypeptide or a juvenile hormone receptor polypeptide.

In a preferred embodiment, the cell of the present invention expresses the polypeptide encoded by the nucleic acid molecule.

In a preferred embodiment, the cell expresses a steroid receptor polypeptide or a fragment thereof which receptor is capable of binding to an insect steroid or analogue thereof or a candidate insecticidally active agent to form an activated complex, and comprises a nucleic acid sequence encoding a bioactive molecule or a reporter molecule operably linked to one or more insect steroid response elements which on binding of the said activated complex promotes transcription of the nucleic acid sequence, wherein said cell on exposure to insect steroid or an analogue thereof, regulates expression of said bioactive molecule or allows detection of said reporter molecule.

In a further aspect of this invention, there is provided an animal (such as a mammal), microorganism, plant or aquatic organism, containing one or more cells as mentioned above.

A further aspect of the present invention provides a method of identifying a modulator of insect steroid receptor-mediated gene expression or insect juvenile hormone receptor-mediated gene expression comprising:
 (i) assaying the expression of a reporter gene in the presence of a recombinant or isolated insect steroid receptor polypeptide or a juvenile hormone receptor polypeptide of the invention and a potential modulator; and
 (ii) assaying the expression of a reporter gene in the presence of a recombinant or isolated insect steroid receptor polypeptide or a juvenile hormone receptor polypeptide of the invention and without said potential modulator; and
 (ii) comparing expression of the reporter gene in the presence of the potential modulator to the expression of a reporter gene in the absence of the potential modulator, wherein said reporter gene is placed operably under the control of a steroid response element (SRE) to which said insect steroid receptor binds or a promoter sequence comprising said SRE.

A still further aspect of the invention provides a method of identifying a potential insecticidal compound comprising:
 (i) assaying the binding directly or indirectly of a recombinant or isolated insect steroid receptor polypeptide or a juvenile hormone receptor polypeptide of the invention to a steroid response element (SRE) to which said insect steroid receptor binds, in the presence of a candidate compound; and
 (ii) assaying the binding directly or indirectly of a recombinant or isolated insect steroid receptor polypeptide or a juvenile hormone receptor polypeptide of the invention to a steroid response element (SRE) to which said insect steroid receptor binds, in the absence of said candidate compound; and
 (ii) comparing the binding assayed at (i) and (ii), wherein a difference in the level of binding indicates that the candidate compound possesses potential insecticidal activity.

A still further aspect of the invention provides a method of identifying a candidate insecticidally-active agent comprising the steps of:
 a) expressing an EcR polypeptide of a steroid receptor or a fragment thereof which includes the ligand-binding region, optionally in association with an EcR partner protein (USP polypeptide) of a steroid receptor or ligand binding domain thereof, optionally in association with an insect steroid or analogue thereof so as to form a complex;
 b) purifying or precipitating the complex;
 c) determining the three-dimensional structure of the ligand binding domain of the complex; and
 d) identifying compounds which bind to or associate with the three-dimensional structure of the ligand binding domain, wherein said compounds represent candidate insecticidally-active agents.

A still further aspect of the invention provides a method of identifying a candidate insecticidally-active agent comprising the steps of:
 a) expressing a USP polypeptide of a juvenile hormone receptor or a fragment thereof which includes the ligand-binding region, optionally in association with an EcR polypeptide of a steroid receptor or ligand binding domain thereof, and optionally in association with an insect steroid or analogue thereof, so as to form a complex;
 b) purifying or precipitating the complex;
 c) determining the three-dimensional structure of the ligand binding domain of the complex; and
 d) identifying compounds which bind to or associate with the three-dimensional structure of the ligand binding domain, wherein said compounds represent candidate insecticidally-active agents.

In another aspect this invention relates to a method or assay for screening insecticidally active compounds which comprises reacting a candidate insecticidal compound with a steroid receptor polypeptide or fragment thereof encompassing the ligand binding domain, or complex thereof with a partner protein or a fragment thereof which encompasses the ligand binding domain, and detecting binding or absence of binding of said compound so as to determine insecticidal activity.

A still further aspect of the invention provides a synthetic compound which interacts with the three dimensional structure of a polypeptide or protein selected from the list comprising:
 (i) an EcR polypeptide of a steroid receptor or a fragment thereof;
 (ii) an EcR partner protein (USP polypeptide) of a steroid receptor or a fragment thereof;
 (iii) a USP polypeptide of a juvenile hormone receptor; and
 (iv) a functional receptor or protein complex formed by association of (i) and (ii), wherein said compound is capable of binding to said polypeptide or protein to agonise or antagonise the binding activity or bioactivity thereof.

Preferably, the synthetic compounds are derived from the three dimensional structure of insect steroid receptor(s) or juvenile hormone receptor(s) which compounds bind to said receptor(s) and have the effect of either inactivating the receptor(s) or potentiating the activity of the receptor(s). More preferably, the compounds mimic the three-dimensional structure of a ligand which binds to the receptor(s) and more preferably, mimic the three-dimensional structure of a ligand which binds to the ligand-binding region of said receptor(s).

In a still further aspect of this invention, there is provided a screening system for insecticidally active agents comprising a nucleotide sequence encoding a steroid receptor or a fragment thereof, and a nucleotide sequence encoding a partner protein or a fragment thereof which associates with the receptor so as to confer enhanced affinity for insect steroid response elements, enhanced affinity for insect steroids or analogues thereof, or insecticidally active agents and/or thermostability or enhanced thermostability of said receptor, which receptor and partner protein is capable of binding to a candidate insecticidally active agent to form an activated complex, and a nucleic acid sequence encoding a bioactive molecule or a reporter molecule operably linked to one or more insect steroid response elements which on binding of the said activated complex regulates transcription of the nucleic acid sequence, wherein on exposure to said agent expression of the bioactive molecule or reporter molecule correlates with insecticidal activity.

In another aspect of this invention, there is provided a method for the regulated production of a bioactive molecule or a reporter molecule in a cell, said method comprising the steps of introducing into said cell:

a) a nucleotide sequence encoding a steroid receptor or a fragment thereof which is capable of binding an insect steroid or analogue thereof, to form an activated complex; and b) a nucleotide sequence encoding said bioactive molecule or reporter molecule operably linked to one or more insect steroid response elements which on binding of the said activated complex regulates transcription of the nucleic acid sequence encoding said bioactive molecule or reporter molecule, wherein exposing the cell to an insect steroid or analogue thereof regulates expression of the bioactive molecule or reporter molecule.

SUMMARY OF SEQUENCE LISTING

| | |
|---|---|
| SEQ ID NO: 1: | The nucleotide sequence of the open reading frame of a cDNA molecule which encodes the EcR polypeptide subunit of the *L. cuprina* ecdysone receptor and amino acid sequence therefor. |
| SEQ ID NO: 2: | The amino acid sequence of the EcR polypeptide subunit of the *L. cuprina* ecdysone receptor. |
| SEQ ID NO: 3: | The nucleotide sequence of the open reading frame of a cDNA molecule which encodes the EcR partner protein (USP polypeptide) subunit of the *L. cuprina* ecdysone receptor and/or which encodes the USP polypeptide subunit of the *L. cuprina* juvenile hormone receptor, and amino acid sequence therefor. |
| SEQ ID NO: 4: | The amino acid sequence of the EcR partner protein (USP polypeptide) subunit of the *L. cuprina* ecdysone receptor and/or the amino acid sequence of the USP polypeptide subunit of the *L. cuprina* juvenile hormone receptor. |
| SEQ ID NO: 5: | The nucleotide sequence of a cDNA molecule which encodes part of the EcR polypeptide subunit of the *M. persicae* ecdysone receptor and amino acid sequence therefor. |
| SEQ ID NO: 6: | The amino acid sequence of a part of the EcR polypeptide subunit of the *M. persicae* ecdysone receptor. |

-continued

SUMMARY OF SEQUENCE LISTING

| | |
|---|---|
| SEQ ID NO: 7: | The nucleotide sequence of the EcR probe 1 which is specific for genetic sequences encoding the EcR polypeptide subunit of aphid ecdysone receptors, in particular the EcR polypeptide subunit of the *M. persicae* ecdysone receptor. |
| SEQ ID NO: 8: | The nucleotide sequence of the EcR probe 2 sequence which is specific for genetic sequences encoding the EcR polypeptide subunit of aphid ecdysone receptors, in particular the EcR polypeptide subunit of the *M. persicae* ecdysone receptor. |
| SEQ ID NO: 9: | The nucleotide sequence of the open reading frame of a cDNA molecule which encodes the EcR polypeptide subunit of the *M. persicae* ecdysone receptor and amino acid sequence therefor. |
| SEQ ID NO: 10: | The amino acid sequence of the EcR polypeptide subunit of the *M. persicae* ecdysone receptor. |
| SEQ ID NO: 11: | The nucleotide sequence of the open reading frame of a cDNA molecule which encodes the EcR partner protein (USP polypeptide) subunit of the *M. persicae* ecdysone receptor and/or which encodes the USP polypeptide subunit of the *M. persicae* juvenile hormone receptor, and amino acid sequence therefor. |
| SEQ ID NO: 12: | The amino acid sequence of the EcR partner protein (USP polypeptide) subunit of the *M. persicae* ecdysone receptor and/or the amino acid sequence of the USP polypeptide subunit of the *M. persicae* juvenile hormone receptor. |
| SEQ ID NO: 13: | The nucleotide sequence of a 150 base-pair probe which is specific for genetic sequences encoding the EcR partner protein (USP polypeptide) subunit of *L. cuprina* ecdysone receptor and/or the USP polypeptide subunit of the *L. cuprina* juvenile hormone receptor, and amino acid sequence therefor. |
| SEQ ID NO: 14: | The amino acid sequence encoded by the nucleotide sequence of SEQ ID NO:13, comprising amino acid residues 108-149 of the EcR partner protein (USP polypeptide) subunit of the *L. cuprina* ecdysone receptor and/or amino acid residues 108-149 of the amino acid sequence of the USP polypeptide subunit of the *L. cuprina* juvenile hormone receptor set forth herein as SEQ ID NO:4. |
| SEQ ID NO: 15: | The nucleotide sequence of the degenerate primer Rdna3. |
| SEQ ID NO: 16: | The nucleotide sequence of the degenerate primer Rdna4. |
| SEQ ID NO: 17: | The nucleotide sequence of the primer Mdna1. |
| SEQ ID NO: 18: | The nucleotide sequence of the primer Mdna2. |
| SEQ ID NO: 19: | The nucleotide sequence of the primer AP1. |
| SEQ ID NO: 20: | The nucleotide sequence of the degenerate primer AP2. |

BRIEF DESCRIPTION OF THE DRAWINGS

FIG. 1 is a graphical representation showing function of the EcR polypeptide subunit of the *L. cuprina* ecdysone receptor in vivo. CHO cells were cotransfected with:

(1) one of the following expression plasmids: pSGDmEcR, pSGLcEcR, or the parental expression plasmid pSG5 as a control, at 1 µg/ml;
(2) plasmid p(EcRE)$_7$-CAT (1 µg/ml); and
(3) an independent reporter plasmid, pPGKLacZ, at 1 µg/ml.

CAT expression was induced with Muristerone A at either 10 µM or 50 µM while control cells received only the carrier ethanol. ELISA kits were used to quantify the synthesis of CAT and β-galactosidase in extracts of cells forty eight hours after transfection. The level of CAT was normalized to the level of β-galactosidase in the same extract. Fold-induction represents the normalized values for CAT gene expression in cells transfected with pSGDmEcR, pSGLcEcR or pSG5 in the presence of hormone, relative to the normalized values for CAT gene expression in cells transfected with the same plasmid, but in the absence of hormone. The average values of three independent experiments are shown and the error bars indicate standard error of the mean.

Figure 2:
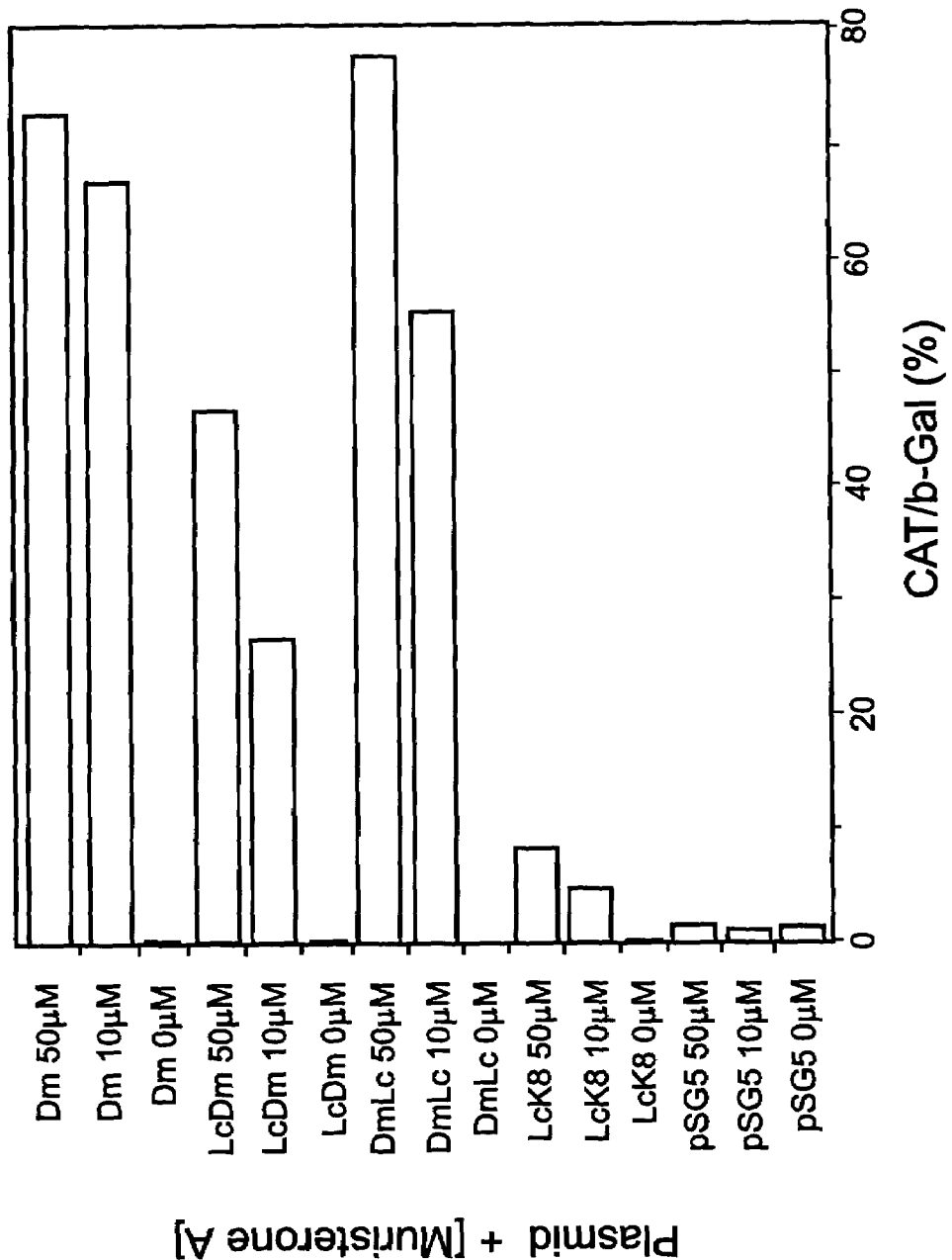

FIG. 2 is a copy of a graphical representation showing the activity of plasmid pSGLD and pSGDL, containing chimeric EcR polypeptide subunits of insect ecdysone receptors, produced as described in the Examples. Cotransfection assays were performed as described in the Examples using plasmids pSGLD and pSGDL and the CAT reporter plasmid p(EcRE)$_7$-CAT (1 ug/ml) and an independent reporter, pPGKLacZ at 1 µg/ml each. CAT/b-Gal (%) refers to CAT reporter activity expressed as a percentage relative to β-galactosidase activity produced by the internal control reporter, pPGKLacZ.

Figure 3:
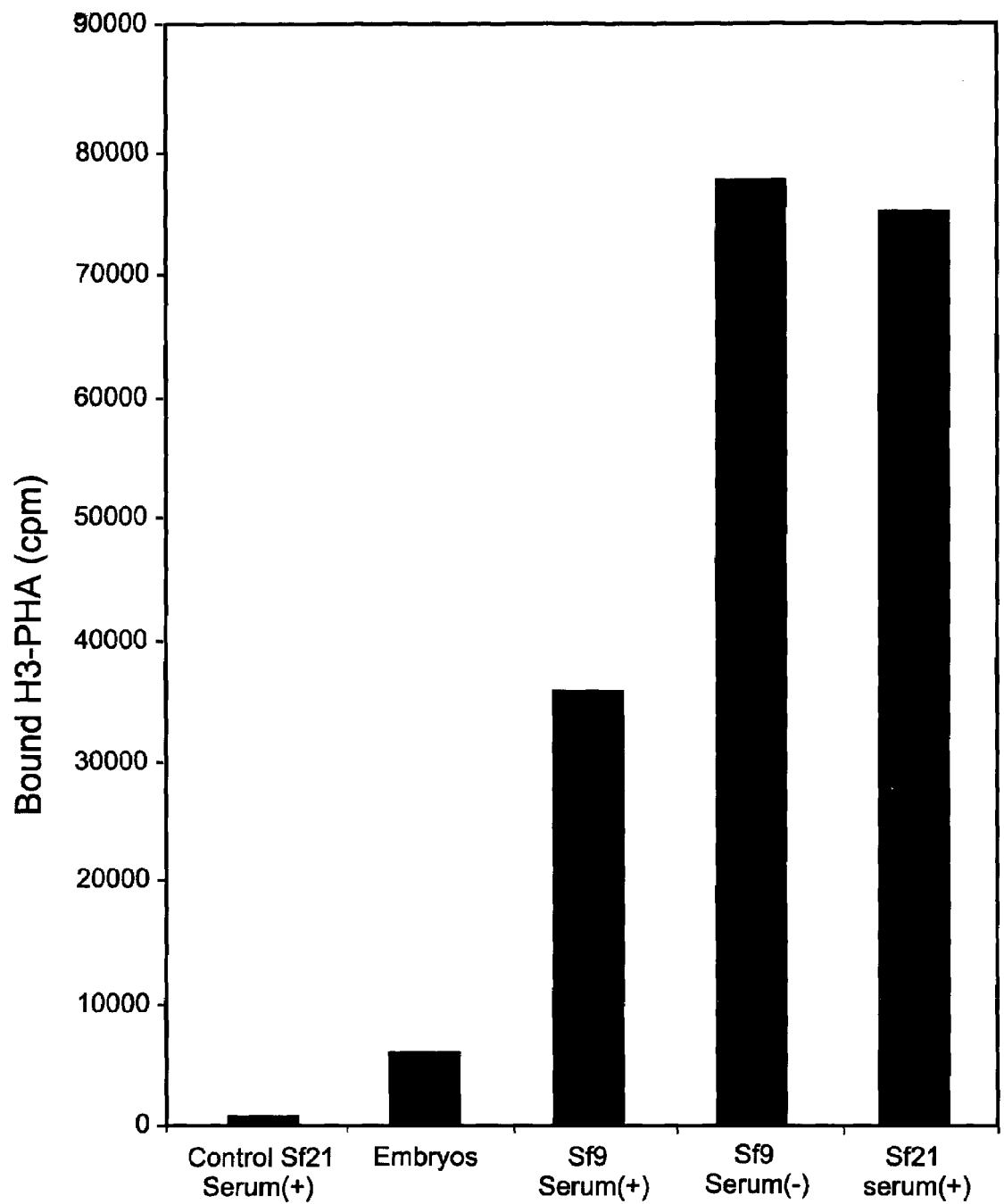

FIG. 3 is a copy of a graphical representation showing the binding activity in extracts of Sf9 and Sf21 cells containing a baculovirus expressing LcEcRDEF and LcUSPDEF, as described in the Examples. Control cells contained baculovirus expressing β-galactosidase and CAT only.

Figure 4:
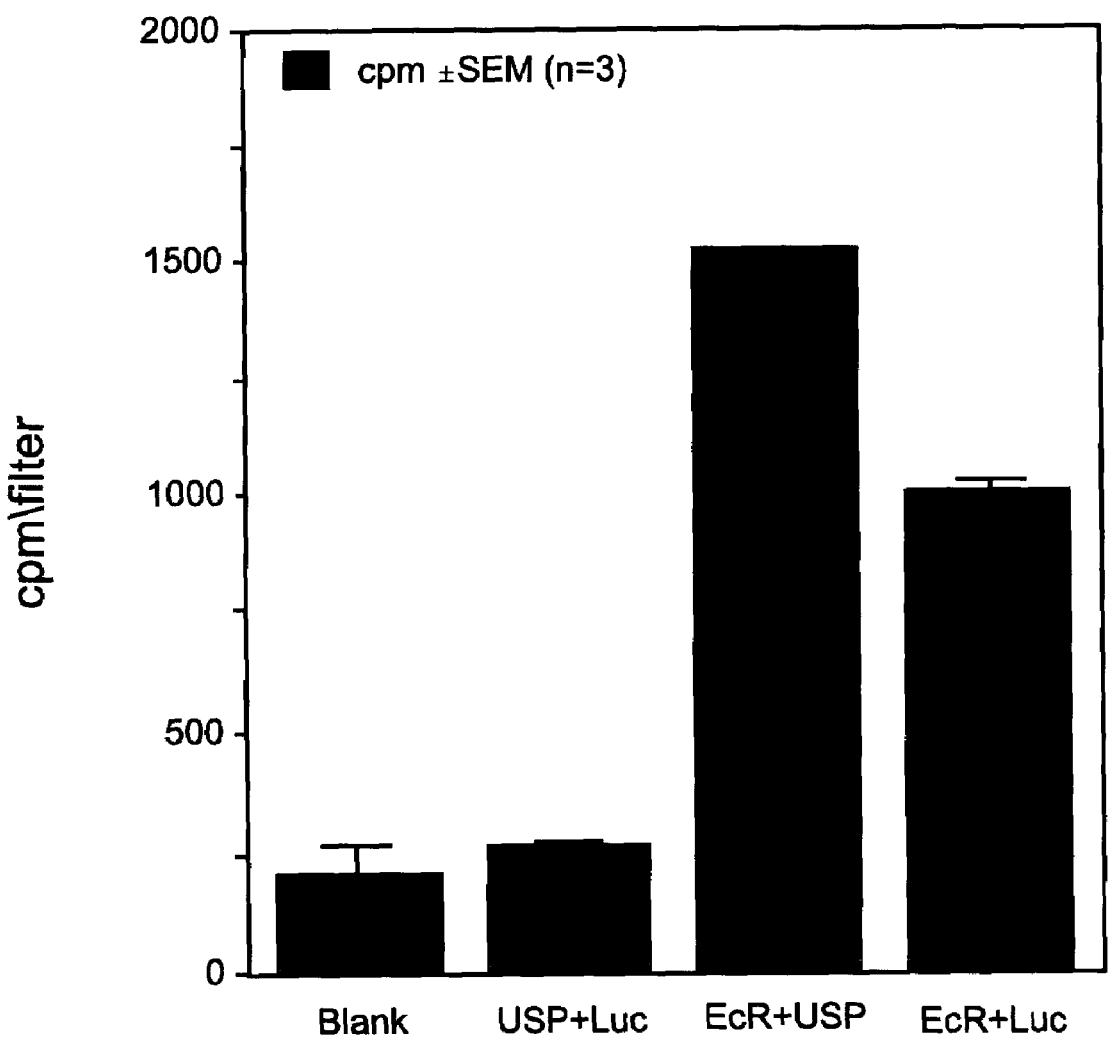

FIG. 4 is a graphical representation showing the ecdysteroid binding activities of an in vitro-translated *Myzus persicae* EcR (MpEcR) polypeptide, an in vitro-translated *Myzus persicae* USP (MpUSP) polypeptide, and an in vitro-translated complex of the *M. persicae* EcR and USP polypeptides.

DETAILED DESCRIPTION OF THE PREFERRED EMBODIMENTS

One aspect of the present invention provides an isolated nucleic acid molecule comprising a nucleotide sequence which encodes or is complementary to a sequence which encodes a steroid receptor polypeptide or a juvenile hormone receptor polypeptide or a bioactive derivative or analogue thereof, wherein said polypeptide:

(i) is selected from the list comprising EcR polypeptide of a steroid receptor, the partner protein (USP polypeptide) of a steroid receptor and the USP polypeptide of a juvenile hormone receptor; and (ii) comprises an amino acid sequence that is at least 40% identical to any one of the amino acid sequences set forth in SEQ ID NO:2, SEQ ID NO:4, SEQ ID NO:6, SEQ ID NO:10, SEQ ID NO:12 or SEQ ID NO:14.

Accordingly, the isolated nucleic acid molecule of the invention may comprise a fragment of a nucleotide sequence encoding a full-length receptor polypeptide.

It is to be understood that a "fragment" of a nucleotide sequence encoding an EcR polypeptide subunit of a steroid receptor or an EcR partner protein (USP polypeptide) of a steroid receptor or a USP polypeptide of a juvenile hormone receptor, refers to a nucleotide sequence encoding a part or fragment of such a receptor which is capable of binding or associating with an insect steroid or an analogue thereof, or a candidate insecticidally active compound. Fragments of a nucleotide sequence would generally comprise in excess of twenty contiguous nucleotides derived from the base sequence and may encode one or more domains of a functional insect steroid receptor or juvenile hormone receptor.

Preferably, the isolated nucleic acid molecule of the invention encodes an ecdysteroid receptor polypeptide. Those skilled in the art are aware that ecdysteroid receptors derived from insects are heterodimeric receptors comprising an EcR polypeptide subunit and an EcR partner protein (USP polypeptide) (see also Jones and Sharp, 1997). In this regard, the present inventors have discovered that the USP polypeptide of the insect juvenile hormone receptor is structurally-identical to the EcR partner protein of the ecdysteroid receptor of the present invention, however juvenile hormone receptors comprise monomers or multimers of the USP polypeptide acting without the EcR polypeptide subunit that is present in the ecdysteroid receptors. Accordingly, the present invention extends equally to nucleotide sequences encoding polypeptides of both the ecdysteroid receptors and polypeptides of the juvenile hormone receptors of insects.

More preferably, the isolated nucleic acid molecule of the invention encodes an ecdysteroid receptor that is modulated by one or more of the steroids ecdysone, ponasterone A, or muristerone, or an analogue of an ecdysteroid.

The isolated nucleic acid molecule of the invention may be derived from any organism that contains steroid receptors that are responsive to ecdysteroids or ecdysteroid-like compounds or juvenile hormones, or analogues of such receptor-ligands. Accordingly, the present invention is not to be limited in any of its embodiments to the particular source of the subject nucleic acid, or polypeptide encoded therefor.

Preferably, the isolated nucleic acid molecule of the invention is derived from insects, helminths (nematodes, cestodes, trematodes), protozoa, and ants, amongst others.

More preferably, the isolated nucleic acid molecule of the invention is derived from an insect selected from the list comprising diptera, hemiptera, coleoptera, neuroptera, lepitdoptera and ants, amongst others. Still more preferably, the isolated nucleic acid molecule of the present invention is derived from aphids, scale insects, leaf hoppers, white fly, and blowflies such as sheep blowflies.

The present invention does not extend to amino acid sequences comprising the complete EcR polypeptide subunit of the *D. melanogaster* ecdysone receptor as described in WO91/13167. However, this exclusion is made on the understanding that the present invention does encompass chimeric genes and fusion proteins which include the *D. melanogaster* nucleotide and amino acid sequences, respectively.

In a particularly preferred embodiment, the isolated nucleic acid molecule of the present invention is derived from the aphid *M. persicae* or alternatively, from the Australian sheep blowfly, *L. cuprina*.

The ecdysteroid receptor is preferably modulated by one or more of the steroids ecdysone, ponasterone A, or muristerone, or an analogue of an ecdysteroid.

As used herein, the term "analogue of an ecdysteroid" shall be taken to indicate any compound that binds to one or more polypeptide subunits of an ecdysteroid receptor or the heterodimeric holoreceptor comprising same or alternatively or in addition, which binds to the USP polypeptide of a juvenile hormone receptor or alternatively or in addition, which binds to a bioactive derivative or analogue of said polypeptides or holoreceptor. The term "analogue of an ecdysteroid" shall further be taken to indicate any compound that modulates the bioactivity of one or more polypeptide subunits of an ecdysteroid receptor or the heterodimeric holoreceptor comprising same or alternatively or in addition, that modulates the bioactivity of the USP polypeptide of a juvenile hormone receptor or alternatively or in addition, that modulates the bioactivity of a bioactive derivative or analogue of said polypeptides or holoreceptor.

The present invention is not to be limited in scope to the specific L. cuprina and M. persicae nucleotide and amino acid sequences set forth in the accompanying Sequence Listing and persons skilled in the art will readily be able to identify additional related sequences from other sources using art-recognised procedures, for example using nucleic acid hybridisation and/or polymerase chain reaction essentially as described by Ausubel et al. (1992) and/or McPherson et al. (1991) and/or Sambrook et al. (1989).

Accordingly, the present invention clearly encompasses isolated nucleic acid molecules which encode or are complementary to isolated nucleic acid molecules which encode the subject EcR polypeptide of a steroid receptor or fragments thereof, and/or the subject EcR partner proteins (USP polypeptide) of a steroid receptor and/or the subject USP polypeptide of a juvenile hormone receptor, in addition to derivatives, fragments and analogues thereof which comprise amino acid sequences having at least 40% identity to the amino acid sequences set forth in any one of SEQ ID NO:2, SEQ ID NO:4, SEQ ID NO:6, SEQ ID NO:10, SEQ ID NO:12 or SEQ ID NO:14.

The present invention clearly extends further to isolated nucleic acid molecules which encode or are complementary to isolated nucleic acid molecules which encode the subject EcR polypeptide of a steroid receptor or fragments thereof, and/or the subject EcR partner proteins (USP polypeptide) of a steroid receptor and/or the subject USP polypeptide of a juvenile hormone receptor, in addition to derivatives, fragments and analogues thereof which comprise amino acid sequences having at least 40% identity to any one or more of the amino acid sequences encoded by the L. cuprina or M. persicae cDNAs contained in AGAL Accession Nos. NM99/04565, NM99/04566, NM99/04567, or NM99/04568.

For the purposes of nomenclature, plasmid pLcEcR contains the cDNA encoding the EcR polypeptide subunit of the Lucilia cuprina ecdysone receptor. This plasmid was deposited on 1 Jul., 1999 with the Australian Government Analytical Laboratories at 1 Suakin Street, Pymble, New South Wales 2073, Australia under the provisions of the Budapest Treaty on the International Recognition of the Deposit of Microorganisms for the Purposes of Patent Procedure and accorded AGAL Accession No. NM99/04566.

For the purposes of nomenclature, plasmid pLcUSP contains the cDNA encoding the EcR partner protein (USP polypeptide) subunit of the Lucilia cuprina ecdysone receptor and/or the USP polypeptide subunit of the L. cuprina juvenile hormone receptor. This plasmid was deposited on 1 Jul., 1999 with the Australian Government Analytical Laboratories at 1 Suakin Street, Pymble, New South Wales 2073, Australia under the provisions of the Budapest Treaty on the International Recognition of the Deposit of Microorganisms for the Purposes of Patent Procedure and accorded AGAL Accession No. NM99/04565.

For the purposes of nomenclature, plasmid pMpEcR contains the cDNA encoding the EcR polypeptide subunit of the Myzus persicae ecdysone receptor. This plasmid was deposited on 1 Jul., 1999 with the Australian Government Analytical Laboratories at 1 Suakin Street, Pymble, New South Wales 2073, Australia under the provisions of the Budapest Treaty on the International Recognition of the Deposit of Microorganisms for the Purposes of Patent Procedure and accorded AGAL Accession No. NM99/04567.

For the purposes of nomenclature, plasmid pMpUSP contains the cDNA encoding the EcR partner protein (USP polypeptide) subunit of the Myzus persicae ecdysone receptor and/or the USP polypeptide subunit of the M. persicae juvenile hormone receptor. This plasmid was deposited on 1 Jul., 1999 with the Australian Government Analytical Laboratories at 1 Suakin Street, Pymble, New South Wales 2073, Australia under the provisions of the Budapest Treaty on the International Recognition of the Deposit of Microorganisms for the Purposes of Patent Procedure and accorded AGAL Accession No. NM99/04568.

The deposits referred to herein will be maintained under the Budapest Treaty on the International Recognition of the Deposit of Microorganisms for the Purposes of Patent Procedure. These deposits are provided merely for the purposes of exemplification and are not an admission that a deposit is required under 35USC §112. A license may be required to make, use or sell the deposited materials or a polypeptide encoded by a cDNA thereof and no such license is hereby granted. It is to be understood however, that the deposits will become publicly available upon the grant of a patent pertaining to the instant disclosure in so far as that patent relates to the deposits referred to herein.

Preferably, the percentage similarity to any one of SEQ ID NO:2, SEQ ID NO:4, SEQ ID NO:6, SEQ ID NO:10, SEQ ID NO:12 or SEQ ID NO:14, or to a polypeptide encoded by a cDNA contained in any one of AGAL Accession Nos. NM99/04565, NM99/04566, NM99/04567, or NM99/04568 is at least about 60%, more preferably at least about 80%, even more preferably at least about 90%.

In determining whether or not two amino acid sequences fall within these percentage limits, those skilled in the art will be aware that it is necessary to conduct a side-by-side comparison or multiple alignment of sequences. In such comparisons or alignments, differences will arise in the positioning of non-identical residues, depending upon the algorithm used to perform the alignment. In the present context, reference to a percentage identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America (Devereaux et al, 1984). The GAP programme utilizes the algorithm of Needleman and Wunsch (1970) to maximise the number of identical/similar residues and to minimise the number and/or length of sequence gaps in the alignment. Alternatively or in addition, wherein more than two amino acid sequences are being compared, the ClustalW programme of Thompson et al (1994) is used.

In an alternative embodiment, the isolated nucleic acid molecule of the invention encodes or is complementary to an isolated nucleic acid molecule which encodes a steroid receptor polypeptide or a fragment thereof, or a partner protein (USP) or a fragment thereof, which at least comprises an amino acid sequence which is substantially identical to any one of SEQ ID NO:2, SEQ ID NO:4, SEQ ID NO:6, SEQ ID NO:10, SEQ ID NO:12 or SEQ ID NO:14 or to the amino acid sequence of a polypeptide encoded by any one of the cDNAs contained in AGAL Accession Nos. NM99/04565, NM99/04566, NM99/04567, or NM99/04568.

As used herein, the term "substantially identical" or similar term shall be taken to include any sequence which is at least about 95% identical and preferably at least 99% or 100% identical to a stated nucleotide sequence or amino acid sequence, including any homologue, analogue or derivative of said stated nucleotide sequence or amino acid sequence.

Those skilled in the art will be aware that variants of the nucleotide sequences set forth in any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13, or variants of the cDNAs contained in any one of the deposited plasmids, which variants encode EcR polypeptides of insect steroid receptors or fragments thereof or EcR partner proteins (USP polypeptides) or fragments thereof, or USP polypeptides of insect juvenile hormone receptors, may be isolated by hybridization under low stringency conditions as exemplified herein.

Such variants include any genomic sequences, cDNA sequences mRNA or other isolated nucleic acid molecules derived from the nucleic acid molecules exemplified herein by the Sequence Listing. Additional variants are not excluded.

In a particularly preferred embodiment of the invention, the variant nucleotide sequences encode a fragment of the EcR polypeptide of the insect steroid receptor or a fragment of the EcR partner protein (USP polypeptide) of the insect steroid receptor or a fragment of the USP polypeptide of the insect juvenile hormone receptor.

Preferred fragments of the subject polypeptides include one or more regions or domains which are involved in the interaction or association between the monomeric polypeptide subunits of a multimeric receptor and/or which are involved in the interaction or association between (i) a cognate steroid or receptor ligand or cis-acting DNA sequence; and (ii) said monomeric polypeptide subunits or the receptor per se. In a particularly preferred embodiment, the fragments comprise the DNA-binding domain, linker domain (domain D) or a part thereof, or ligand-binding domain (eg. hormone-binding domain) of a steroid receptor polypeptide or juvenile hormone receptor polypeptide or receptor holoenzyme. As exemplified herein, wherein biological activity of the *L. cuprina* ecdysone receptor is required, it is preferably to include at least a ligand-binding region comprising the ligand-binding domain and at least a part of the linker domain of the EcR polypeptide subunit, optionally in association with a ligand-binding region comprising at least the ligand-binding domain and at least a part of the linker domain of the EcR partner protein (USP polypeptide) subunit of said receptor. Additional fragments are not excluded.

Homologues, analogues and derivatives of the nucleotide sequences exemplified herein may be isolated by hybridising same under at least low stringency conditions and preferably under at least medium stringency conditions, to the nucleic acid molecule set forth in any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13 or to a complementary strand thereof, or to the cDNAs contained in any one or more of the deposited plasmids. More preferably, the isolated nucleic acid molecule according to this aspect of the invention is capable of hybridising under at least high stringency conditions to the nucleic acid molecule set forth in any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13 or to a complementary strand thereof, or to the cDNAs contained in any one or more of the deposited plasmids.

For the purposes of defining the level of stringency, a low stringency is defined herein as being a hybridisation and/or a wash carried out in 6×SSC buffer, 0.1% (w/v) SDS at 28° C. or alternatively, as exemplified herein. Generally, the stringency is increased by reducing the concentration of SSC buffer, and/or increasing the concentration of SDS and/or increasing the temperature of the hybridisation and/or wash. A medium stringency comprises a hybridisation and/or a wash carried out in 0.2×SSC-2×SSC buffer, 0.1% (w/v) SDS at 42° C. to 65° C., while a high stringency comprises a hybridisation and/or a wash carried out in 0.1×SSC-0.2× SSC buffer, 0.1% (w/v) SDS at a temperature of at least 55° C. Conditions for hybridisations and washes are well understood by one normally skilled in the art. For the purposes of further clarification only, reference to the parameters affecting hybridisation between nucleic acid molecules is found in Ausubel et al. (1992), which is herein incorporated by reference.

In an even more preferred embodiment of the invention, a hybridising nucleic acid molecule further comprises a sequence of nucleotides which is at least 40% identical to at least 10 contiguous nucleotides, preferably at least 50 contiguous nucleotides and more preferably at least 100 contiguous nucleotides, derived from any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13 or a complementary strand thereof, or from a cDNA contained in any one or more of the deposited plasmids.

In determining whether or not two nucleotide sequences fall within these percentage limits, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, 1984).

In an alternative embodiment, nucleotide sequences encoding EcR polypeptide subunits of insect steroid receptors or fragments thereof and/or EcR partner proteins (USP polypeptides) of insect steroid receptor or fragments thereof, or USP polypeptides of insect juvenile hormone receptor polypeptides, are amplified in the polymerase chain reaction. According to this embodiment, one or two or more nucleic acid "primer molecules" derived from a nucleotide sequence exemplified herein as SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13 or a complementary strand thereof, or from a cDNA contained in any one or more of the deposited plasmids, are annealed or hybridized to a nucleic acid "template molecule" which at least comprises a nucleotide sequence encoding a related genetic sequence or a functional part thereof, and nucleic acid molecule copies of the template molecule are amplified enzymatically using a thermostable DNA polymerase enzyme, such as TaqI polymerase or Pfu polymerase, amongst others.

More particularly, one of the primer molecules comprises contiguous nucleotides derived from any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13, or alternatively, from a cDNA contained in any one or more of the deposited plasmids; and another of said primers comprises contiguous nucleotides complementary to SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13, or alternatively, from a cDNA contained in any one or more of the deposited plasmids, subject to the proviso that the first and second primers are not complementary to each other.

In a preferred embodiment, each nucleic acid primer molecule is at least 10 nucleotides in length, more preferably at least 20 nucleotides in length, even more preferably at least 30 nucleotides in length, still more preferably at least 40 nucleotides in length and even still more preferably at least 50 nucleotides in length.

Furthermore, the nucleic acid primer molecules consists of a combination of any of the nucleotides adenine, cytidine, guanine, thymidine, or inosine, or functional analogues or derivatives thereof which are at least capable of being incorporated into a polynucleotide molecule without having an inhibitory effect on the hybridisation of said primer to the template molecule in the environment in which it is used.

Furthermore, one or both of the nucleic acid primer molecules may be contained in an aqueous mixture of other nucleic acid primer molecules, for example a mixture of degenerate primer sequences which vary from each other by one or more nucleotide substitutions or deletions. Alternatively, one or both of the nucleic acid primer molecules may be in a substantially pure form.

In a particularly preferred embodiment exemplified herein, two primer nucleotide sequences are used to amplify related sequences, said primers comprising the nucleotide sequences as set forth in any one of SEQ ID NO:15 to SEQ ID NO:20 inclusive. Even more preferably, the primers are used in the combination of (i) SEQ ID NO:15 and SEQ ID NO:16; or (ii) SEQ ID NO:17 and SEQ ID NO:18; or (iii) SEQ ID NO:19 and SEQ ID NO:20.

The nucleic acid template molecule may be in a recombinant form, in a virus particle, insect cell, bacteriophage particle, yeast cell, animal cell, or a plant cell. Preferably, the nucleic acid template molecule is derived from an insect species.

Those skilled in the art will be aware that there are many known variations of the basic polymerase chain reaction procedure. Such variations are discussed, for example, in McPherson et al (1991). The present invention extends to the use of all such variations in the isolation of variant insect steroid receptor-encoding genes or fragments thereof, and/or variant partner protein-encoding genes or fragments thereof to those exemplified herein.

The isolated nucleic acid molecule of the present invention, including those sequences exemplified herein and any variants thereof, may be cloned into a plasmid or bacteriophage molecule, for example to facilitate the preparation of primer molecules or hybridisation probes or for the production of recombinant gene products. Methods for the production of such recombinant plasmids, cosmids, bacteriophage molecules or other recombinant molecules are well-known to those of ordinary skill in the art and can be accomplished without undue experimentation. Accordingly, the invention further extends to any recombinant plasmid, bacteriophage, cosmid or other recombinant molecule comprising the nucleotide sequence set forth in any one of SEQ ID NO:1 or SEQ ID NO:3 or SEQ ID NO:5 or SEQ ID NO:7 or SEQ ID NO:8 or SEQ ID NO:9 or SEQ ID NO:11 or SEQ ID NO:13 or SEQ ID NO:15 to SEQ ID NO:20, or a complementary sequence, homologue, analogue or derivative thereof, or a cDNA contained in any one or more of the deposited plasmids.

The nucleic acid molecule of the present invention is also useful for developing genetic constructs which comprise and preferably, express, the EcR polypeptide subunit of the insect steroid receptor and/or the EcR partner protein (USP polypeptide) of the steroid receptor and/or the USP polypeptide of the juvenile hormone receptor, thereby providing for the production of the recombinant polypeptides in isolated cells or transformed tissues.

Accordingly, a further aspect of the present invention provides a genetic construct comprising the subject isolated nucleic acid molecule encoding the insect steroid receptor polypeptide or a juvenile hormone receptor polypeptide, operably linked to a promoter sequence. Preferably, the subject nucleic acid molecule is in an expressible format, such that it is possible to produce a recombinant polypeptide therefrom.

Reference herein to a "promoter" is to be taken in its broadest context and includes the transcriptional regulatory sequences of a classical genomic gene, including the TATA box which is required for accurate transcription initiation in a eukaryotic cell, with or without a CCAAT box sequence or alternatively, the Pribnow box required for accurate expression in prokaryotic cells.

Promoters may be cell, tissue, organ or system specific, or may be non-specific. Using specific promoters, the expression of a bioactive agent or other polypeptide encoded by a structural gene to which the promoter is operably connected may be targeted to a desired cellular site. For example, in transgenic animals such as sheep, it can be envisaged that cells of the transgenic animal may contain a gene encoding a steroid receptor, preferably a steroid receptor linked to an epidermal specific promoter and a separate gene encoding, for example, epidermal growth factor (EGF) which is functionally linked to one or more insect hormone response elements and may or may not also be linked to epidermal specific promoter elements. On administration of the appropriate insect steroid hormone to the transgenic animal, the activated complex between the insect steroid receptor and insect steroid may bind to the one or more insect steroid hormone response element thereby inducing EGF production solely in epidermal cells which may give rise to defleecing. It is to be understood that this aspect of the invention is independent of the degree of thermostability of the insect steroid receptor. The same principal applies to expression of any bioactive molecule or reporter molecule in a specific cell type which is regulated by a transactivating complex between a steroid receptor complex and an appropriate insect steroid.

In the present context, the term "promoter" is also used to describe a synthetic or fusion molecule, or derivative which confers, activates or enhances expression in a cell in response to an external stimulus. Accordingly, the promoter may include further regulatory elements (i.e. upstream activating sequences, enhancers and silencers) which alter gene expression in response to developmental and/or external stimuli, or in a tissue-specific manner. Preferred promoters may contain copies of one or more specific regulatory elements, in particular steroid responsive elements (SREs) or hormone-responsive elements (HREs), to further enhance expression and/or to alter the spatial expression and/or temporal expression pattern.

Reference herein to the term "steroid response element" shall be taken to refers to one or more cis-acting nucleotide sequences present in a naturally-occurring or synthetic or recombinant gene the expression of which is regulated by an insect steroid, such as an ecdysteroid, for example ecdysone or ponasterone A, wherein said regulation of expression results from an direct or indirect interaction between a steroid receptor and said cis-acting nucleotide sequence response element. Exemplary insect steroid hormone response elements include the ecdysone response element hsp27 (EcRE) and any other nucleotide sequence which is capable of binding ecdysteroid receptors or polypeptide subunits thereof or fragments or analogies thereof (such as associated with E75, E74 or other *Drosophila* early genes), as described for example by Riddihough and Pelham (1987).

For example, an SRE or a plurality of such elements may be operably linked to a promoter such as the polyhedrin promoter, p10 promoter, MMTV promoter or SV40 promoter, to make transcription of a structural gene to which said promoter is operably connected responsive to the presence of a steroid bound to the insect receptor (which may act as a transcription factor). One or more insect SREs may be located within a promoter, and may replace sequences within a selected promoter which confer responsiveness to hormones or other agents which regulate promoter activity.

Where response elements are different they may lead to preferential binding of different insect steroids or analogues thereof such that a promoter may be differentially regulated.

Particularly preferred SREs according to this embodiment include, but are not limited to, the hsp27 ecdysone response element described by Riddihough and Pelham (1987) or the 13 base-pair palindromic core contained therein.

A promoter is usually, but not necessarily, positioned upstream or 5', of a structural gene, the expression of which it regulates. Furthermore, the regulatory elements comprising a promoter are usually positioned within 2 kb of the start site of transcription of the gene.

Placing a gene or isolated nucleic acid molecule operably under the control of a promoter sequence means positioning said gene or isolated nucleic acid molecule such that its expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Those skilled in the art will recognise that the choice of promoter will depend upon the nature of the cell being transformed and when expression is required. Furthermore, it is well-known in the art that the promoter sequence used in the expression vector will also vary depending upon the level of expression required and whether expression is intended to be constitutive or regulated.

For expression in eukaryotic cells, the genetic construct generally comprises, in addition to the nucleic acid molecule of the invention, a promoter and optionally other regulatory sequences designed to facilitate expression of said nucleic acid molecule. The promoter may be derived from a genomic clone which normally encodes the expressed protein or alternatively, it may be a heterologous promoter derived from another genetic source. Promoter sequences suitable for expression of genes in eukaryotic cells are well-known in the art.

Suitable promoters for use in eukaryotic expression vectors include those capable of regulating expression in mammalian cells, insect cells such as Sf9 or Sf21. (*Spodoptera frugiperda*) cells, yeast cells and plant cells. Preferred promoters for expression in eukaryotic cells include the p10 promoter, MMTV promoter, polyhedrin promoter, the SV40 early promoter and the cytomegalovirus (CMV-IE) promoter, promoters derived from immunoglobulin-producing cells (see, U.S. Pat. No. 4,663,281), polyoma virus promoters, and the LTR from various retroviruses (such as murine leukemia virus, murine or Rous sarcoma virus and HIV), amongst others (See, *Enhancers and Eukaryotic Gene Expression*, Cold Spring Harbor Press, New York, 1983, which is incorporated herein by reference). Examples of other expression control sequences are enhancers or promoters derived from viruses, such as SV40, Adenovirus, Bovine Papilloma Virus, and the like.

Wherein the expression vector is intended for the production of recombinant protein, the promoter is further selected such that it is capable of regulating expression in a cell which is capable of performing any post-translational modification to the polypeptide which may be required for the subject recombinant polypeptide to be functional, such as N-linked glycosylation. Cells suitable for such purposes may be readily determined by those skilled in the art. By way of exemplification, Chinese hamster ovary (CHO) cells may be employed to carry out the N-terminal glycosylation and signal sequence cleavage of a recombinant polypeptide produced therein. Alternatively, a baculovirus expression vector such as the pFastBac vector supplied by GibcoBRL may be used to express recombinant polypeptides in Sf9 (*Spodoptera frugiperda*) cells, following standard protocols.

Numerous expression vectors suitable for the present purpose have been described and are readily available. The expression vector may be based upon the pcDNA3 vector distributed by Medos Company Pty Ltd, Victoria, Australia, which comprises the CMV promoter and BGH terminator sequences for regulating expression of the recombinant polypeptide of the invention in a eukaryotic cell, when isolated nucleic acid sequences encoding same are inserted, in the sense orientation relative to the CMV promoter, into the multiple cloning site of said vector. Alternatively, the SG5 expression vector of Greene et al. (1988), supplied by Stratagene, or the pQE series of vectors supplied by Qiagen are particularly useful for such purposes, as exemplified herein.

Examples of eukaryotic cells contemplated herein to be suitable for expression include mammalian, yeast, insect, plant cells or cell lines such as COS, VERO, HeLa, mouse C127, Chinese hamster ovary (CHO), WI-38, baby hamster kidney (BHK), MDCK, sf21 (insect) or Sf9 (insect) cell lines. Such cell lines are readily available to those skilled in the art.

The prerequisite for expression in prokaryotic cells such as *Escherichia coli* is the use of a strong promoter with an effective ribosome binding site. Typical promoters suitable for expression in bacterial cells such as *E. coli* include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in *E. coli* are well-known in the art and are described for example in Ausubel et al (1992).

Numerous vectors having suitable promoter sequences for expression in bacteria have been described, such as for example, pKC30 ($\lambda_L$: Shimatake and Rosenberg, 1981), pKK173-3 (tac: Amann and Brosius, 1985), pET-3 (T7: Studier and Moffat, 1986) or the pQE series of expression vectors (Qiagen, CA), amongst others.

Suitable prokaryotic cells include *corynebacterium*, *salmonella*, *Escherichia coli*, *Bacillus* sp. and *Pseudomonas* sp, amongst others. Bacterial strains which are suitable for the present purpose are well-known in the relevant art (Ausubel et al, 1992).

The genetic constructs described herein may further comprise genetic sequences corresponding to a bacterial origin of replication and/or a selectable marker gene such as an antibiotic-resistance gene, suitable for the maintenance and replication of said genetic construct in a prokaryotic or eukaryotic cell, tissue or organism. Such sequences are well-known in the art.

Selectable marker genes include genes which when expressed are capable of conferring resistance on a cell to a compound which would, absent expression of said selectable marker gene, prevent or slow cell proliferation or result in cell death. Preferred selectable marker genes contemplated herein include, but are not limited to antibiotic-resistance genes such as those conferring resistance to ampicillin, Claforan, gentamycin, G-418, hygromycin, rifampicin, kanamycin, neomycin, spectinomycin, tetracycline or a derivative or related compound thereof or any other compound which may be toxic to a cell.

The origin of replication or a selectable marker gene will be spatially-separated from those genetic sequences which encode the recombinant receptor polypeptide or fusion polypeptide comprising same.

Preferably, the genetic constructs of the invention, including any expression vectors, are capable of introduction into, and expression in, an in vitro cell culture, or for introduction into, with or without integration into the genome of a cultured cell, cell line and/or transgenic animal. In a particularly preferred embodiment, the expression vector is selected from the group consisting of: pLcEcR (AGAL Accession No. NM99/04566); pLcUSP (AGAL Accession No. NM99/04565); pMpEcR (AGAL Accession No. NM99/04567); and pMpUSP (AGAL Accession No. NM99/04568.).

A further aspect of the invention provides a cell comprising the subject isolated nucleic acid molecule which encodes a steroid receptor polypeptide or a juvenile hormone receptor polypeptide.

As used herein, the word "cell" shall be taken to refer to a single cell, or a cell lysate, or a tissue, organ or whole organism comprising same, including a tissue, organ or whole organism comprising a clonal group of cells or a heterogenous mixture of cell types, which may be a prokaryotic or eukaryotic cell as described supra.

In a preferred embodiment, the cell of the present invention expresses the isolated or recombinant polypeptide encoded by the nucleic acid molecule.

In a preferred embodiment, the cell expresses a steroid receptor polypeptide or a fragment thereof which receptor is capable of binding to an insect steroid or analogue thereof or a candidate insecticidally active agent to form an activated complex, and comprises a nucleic acid sequence encoding a bioactive molecule or a reporter molecule operably linked to one or more insect steroid response elements which on binding of the said activated complex promotes transcription of the nucleic acid sequence, wherein said cell on exposure to insect steroid or an analogue thereof, regulates expression of said bioactive molecule or allows detection of said reporter molecule.

To produce the cells of the invention, host cells are transfected or co-transfected or transformed with nucleotide sequences containing the DNA segments of interest (for example, the insect steroid receptor gene, the recombinant steroid response elements, or both) by well-known methods, which vary depending on the type of cellular host. For example, calcium chloride transfection is commonly utilized for prokaryotic cells, whereas lipofection or calcium phosphate treatment are often used for other cellular hosts. See, generally, Sambrook et al, (1989); Ausubel et al, (1992); and Potrykus (1990). Other transformation techniques include electroporation, DEAE-dextran, microprojectile bombardment, lipofection, microinjection, and others.

As used herein, the term "transformed cell" is meant to also include the progeny of a transformed cell.

In a further aspect of this invention, there is provided an animal (such as a mammal or insect), microorganism, plant or aquatic organism, containing one or more cells as mentioned above. Reference to plants, microorganisms and aquatic organisms includes any such organisms.

In this embodiment of the invention, it is to be appreciated that administration of an insect steroid or an analogue thereof to an organism will induce expression of the desired bioactive molecule, such as a polypeptide, with attendant advantages. For example, an induced protein may have a therapeutic effect ameliorating a disease state or preventing susceptibility to disease or may modify in some way the phenotype of an organism to produce a desired effect. In humans, for example, cell transplants (such as liver cells) may under the action of insect steroids, produce desirable hormones such as insulin, growth hormone, growth factors and the like.

A further aspect of the invention provides a recombinant or isolated polypeptide comprising a steroid receptor polypeptide or juvenile hormone receptor polypeptide derived from an insect or a bioactive derivative or analogue thereof, wherein said polypeptide:

(i) is selected from the list comprising EcR polypeptide of a steroid receptor, the partner protein (USP polypeptide) of a steroid receptor and the USP polypeptide of a juvenile hormone receptor; and (ii) comprises an amino acid sequence that is at least 40% identical to any one of the amino acid sequences set forth in SEQ ID NO:2, SEQ ID NO:4, SEQ ID NO:6, SEQ ID NO:10, SEQ ID NO:12 or SEQ ID NO:14;

wherein said polypeptide is substantially free of naturally-associated insect cell components.

In an alternative embodiment, the recombinant or isolated polypeptide comprising a steroid receptor polypeptide or juvenile hormone receptor polypeptide derived from an insect or a bioactive derivative or analogue thereof, wherein said polypeptide:
  (i) is selected from the list comprising EcR polypeptide of a steroid receptor, the partner protein (USP polypeptide) of a steroid receptor and the USP polypeptide of a juvenile hormone receptor; and
  (ii) comprises an amino acid sequence that is at least 40% identical to an amino acid sequence encoded by the cDNA present in any one of the plasmids deposited under AGAL Accession No. NM99/04565, NM99/04566, NM99/04567, or NM99/04568;

wherein said polypeptide is substantially free of naturally-associated insect cell components.

Reference herein to "substantially free of naturally associated insect cell components" refers to at least 80% purity, preferably more than 90% purity, and more preferably more than 95% purity. Normally, purity is measured on a polyacrylamide gel with homogeneity determined by staining of protein bonds. Alternatively, high resolution may be necessary using HPLC or similar means. For most purposes, a simple chromatography column or polyacrylamide gel may be used to determine purity. A protein which is chemically synthesized or synthesized in a cell system different from an insect cell from which it naturally originates would be free of naturally-associated insect cell components.

The present invention clearly provides for the isolation of EcR polypeptide subunits and EcR partner protein (USP polypeptide) subunits of ecdysteroid receptors and USP polypeptides of juvenile hormone receptors, from various organisms of the class Insecta, as described supra, in addition to protozoa and helminth sources.

Insect steroid receptors are characterized by functional ligand-binding domains, and DNA-binding domains, both of which interact to effect a change in the regulatory state of a gene operably linked to the DNA-binding site of the holoreceptor or a polypeptide or polypeptide fragment thereof. Thus, insect steroid receptors seem to be ligand-responsive transcription factors. Additionally, insect steroid receptors generally contain a DNA-binding domain (Domain C), and a ligand-binding domain (Domain E), separated and flanked by additional domains as identified by Krust et al (1986). The C domain preferably comprises a zinc-finger DNA-binding domain which is usually hydrophilic, having high cysteine, lysine and arginine content. The E domain preferably comprises hydrophobic amino acid residues and is further characterized by regions E1, E2 and E3. The ligand-binding domain of the members of the insect steroid receptor superfamily is typically carboxyl-proximal, relative to a DNA-binding domain (Evans, 1988). The entire ligand-binding domain is typically between about 200 and 250 amino acids but is potentially shorter. This domain has the subregions of high homology, designated the E1, E2 and E3 regions—which may be collectively referred to as the "E region". Amino acid residues proximal to the C domain comprise a region initially defined as separate A and B domains. Region D separates the more conserved domains C and E. Region D typically has a hydrophilic region whose predicted secondary structure is rich in turns and coils. The F region is carboxy promixal to the E region (see, Krust et al, supra).

The receptor polypeptides of the present invention exhibit at least a ligand-binding domain, as characterized by sequence homology to regions E1, E2 and E3. The ligand-binding domains of the present invention are typically characterized by having significant homology in sequence and structure to these three regions. Fragments of insect steroid receptors and partner proteins capable of binding insect steroids, and candidate insecticidally active compounds comprise an E-region or a sufficient portion of the E-region to allow binding.

Preferably, the recombinant or isolated EcR polypeptide subunit of the insect steroid receptor or EcR partner protein (USP polypeptide) subunit of the steroid receptor or USP polypeptide of the juvenile hormone receptor as described herein is thermostable.

By "thermostable" is meant that a stated integer does not exhibit reduced activity at bacterial, plant or animal physiological temperatures above about 28° C. or above about 30° C. The thermostability of insect steroid hormone receptors also refers to the capacity of such receptors to bind to ligand-binding domains or regions and/or to transactivate genes linked to insect steroid hormone response elements at bacterial, plant or animal physiological temperatures above about 28° C. or above about 30° C.

The present invention clearly extends to variants of said polypeptides, as described supra. The polypeptide may be substantially free of naturally associated insect cell components, or may be in combination with a partner protein which associates with the insect steroid receptor so as to confer enhanced affinity for insect steroid response elements, enhanced affinity for insect steroids or analogues thereof. For example, the amino acid sequences exemplified herein may be varied by the deletion, substitution or insertion of one or more amino acids.

In one embodiment, amino acids of a polypeptide exemplified herein may be replaced by other amino acids having similar properties, for example hydrophobicity, hydrophilicity, hydrophobic moment, charge or antigenicity, and so on.

Substitutions encompass amino acid alterations in which an amino acid of the base polypeptide is replaced with a different naturally-occurring or a non-conventional amino acid residue. Such substitutions may be classified as "conservative", in which case an amino acid residue contained in the base polypeptide is replaced with another naturally-occurring amino acid of similar character, for example Gly↔Ala, Val↔Ile↔Leu, Asp↔Glu, Lys↔Arg, Asn↔Gln or Phe↔Trp↔Tyr.

Substitutions encompassed by the present invention may also be "non-conservative", in which an amino acid residue which is present in the base polypeptide is substituted with an amino acid having different properties, such as a naturally-occurring amino acid from a different group (eg. substituted a charged or hydrophobic amino acid with alanine), or alternatively, in which a naturally-occurring amino acid is substituted with a non-conventional amino acid.

Those skilled in the art will be aware that several means are available for producing variants of the exemplified EcR polypeptide subunit of the insect steroid receptor or EcR partner protein (USP polypeptide) subunit of the steroid receptor or USP polypeptide of the juvenile hormone receptor, when provided with the nucleotide sequence of the nucleic acid molecule which encodes said polypeptide, for example site-directed mutagenesis of DNA and polymerase chain reaction utilising mutagenised oligonucleotide primers, amongst others.

Such polypeptide variants which are capable of binding insect steroids clearly form part of the present invention. Assays to determine such binding may be carried out according to procedures well known in the art.

One such variant polypeptide encompassed by the present invention comprises an "in-frame" fusion polypeptide between different regions of different insect receptor polypeptides. As exemplified herein, the present inventors have discovered that, by producing synthetic genes in which various domains of a base insect steroid receptor-encoding nucleotide sequence derived from a first source are interchanged or substituted with similar sequences derived from a second source (referred to as "domain swapping"), it is possible to modify the bioactivity of the insect steroid receptor encoded therefor. For example, the biological activity of the EcR polypeptide of the *L. cuprina* or *M. persicae* ecdysone receptor exemplified herein may be modulated by replacing portions of its C-terminal or N-terminal sequences with the equivalent domains from the EcR polypeptide of the *D. melanogaster* ecdysone receptor or alternatively, by swapping regions of the EcR polypeptides of the *L. cuprina* and *M. persicae* ecdysone receptors per se.

As a further refinement, such changes in biological function can similarly be effected by making specific changes (e.g. addition, substitution or deletion) to only those amino-acids within each domain that are critical for determining the relevant catalytic function (eg. ligand-binding activity, DNA binding site affinity, etc), such as by site-directed mutagenesis.

According to this embodiment, there is provided a synthetic EcR polypeptide subunit of a steroid receptor, and/or a synthetic EcR partner protein (USP polypeptide) subunit of a steroid receptor, and/or a synthetic USP polypeptide of a juvenile hormone receptor, or an analogue or derive of said synthetic polypeptides, wherein said synthetic polypeptides comprise an amino acid sequence which has the following properties:

(i) it differs in amino acid sequence or exhibits different biological properties to a naturally-occurring EcR polypeptide subunit of a steroid receptor, and/or a naturally-occurring EcR partner protein (USP polypeptide) subunit of a steroid receptor, and/or a naturally-occurring USP polypeptide of a juvenile hormone receptor;

(ii) it comprises a first sequence of amino acids which are at least about 40% identical to a part of any one of SEQ ID NO:2, SEQ ID NO:4, SEQ ID NO:6, SEQ ID NO:10, SEQ ID NO:12 or SEQ ID NO:14, or at least about 40% identical to a part of an amino acid sequence encoded by any one of the deposited plasmids, linked covalently to a second sequence of amino acids derived from an EcR polypeptide subunit of a steroid receptor, EcR partner protein (USP polypeptide) subunit of a steroid receptor, or USP polypeptide of a juvenile hormone receptor, wherein said first and second sequences are derived from different genomic sources.

Preferably, the first sequence of amino acids is derived from the EcR polypeptide subunit of a steroid receptor, more preferably from the EcR polypeptide of the *L. cuprina* or *M. persicae* ecdysone receptor, and even more preferably from the EcR polypeptide of the *L. cuprina* ecdysone receptor.

In one embodiment, the synthetic EcR polypeptide subunit of a steroid receptor, and/or a synthetic EcR partner protein (USP polypeptide) subunit of a steroid receptor, and/or a synthetic USP polypeptide of a juvenile hormone receptor comprises a fusion polypeptide in which the ligand-binding regions of any one of SEQ ID NO:2, SEQ ID NO:4, SEQ ID NO:6, SEQ ID NO:10, SEQ ID NO:12 or SEQ ID NO:14 are replaced, in-frame, by the ligand-binding region of a different receptor polypeptide.

In a particularly preferred embodiment, 5'-end of the open reading frame of a first nucleotide sequence, encoding the N-terminal portion of the EcR polypeptide of a first ecdysteroid receptor to the end of the DNA-binding domain of said polypeptide, is fused in-frame, to the 3'-end of the open reading frame of a second nucleotide sequence, encoding the C-terminal portion of the EcR polypeptide of a second ecdysteroid receptor, from the D domain and hormone-binding domain to the carboxyl terminus.

Accordingly, the present invention extends to any variants of the insect receptor polypeptides referred to herein and genetic sequences encoding same, wherein said variants are derived from a receptor polypeptide as described herein and exhibit demonstrable ligand-binding activity, and either comprises an amino acid sequence which differs from a naturally-occurring receptor polypeptide, or exhibit biological activity.

As with other aspects of the invention, the variants described herein may be produced as recombinant polypeptides or in transgenic organisms, once the subject synthetic genes are introduced into a suitable host cell and expressed therein.

In an alternative embodiment, the recombinant receptor polypeptide of the invention is produced as an "in-frame" fusion polypeptide with a second polypeptide, for example a detectable reporter polypeptide such as β-galactosidase, β-glucuronidase, luciferase or other enzyme, or a FLAG peptide, hapten peptide such as a poly-lysine or poly-histidine or other polypeptide molecule.

By "in-frame" means that a nucleotide sequence which encodes a first polypeptide is placed (i.e. cloned or ligated) in the same open reading frame adjacent to a nucleotide sequence which encodes a second polypeptide with no intervening stop codons there between, such that when the ligated nucleic acid molecule is expressed, a single fusion polypeptide is produced which comprises a sequence of amino acids corresponding to the summation of the individual amino acid sequences of the first and second polypeptides.

In order to produce a fusion polypeptide, the nucleic acid molecule which encodes the polypeptide of the invention, or an analogue or derivative thereof, is cloned adjacent to a second nucleic acid molecule encoding the second polypeptide, optionally separated by a spacer nucleic acid molecule which encodes one or more amino acids (eg: poly-lysine or poly histidine, amongst others), such that the first coding region and the second coding region are in the same open reading frame, with no intervening stop codons between the two coding regions. When translated, the polypeptide thus produced comprises a fusion between the polypeptide products of the first and second coding regions. Wherein a spacer nucleic acid molecule is utilised in the genetic construct, it may be desirable for said spacer to at least encode an amino acid sequence which is cleavable to assist in separation of the fused polypeptide products of the first and second coding regions, for example a thrombin cleavage site.

A genetic construct which encodes a fusion polypeptide further comprises at least one start codon and one stop codon, capable of being recognised by the cell's translational machinery in which expression is intended.

Preferably, a genetic construct which encodes a fusion polypeptide may be further modified to include a genetic sequence which encodes a targeting signal placed in-frame with the coding region of the nucleotide sequence encoding the fusion polypeptide, to target the expressed recombinant polypeptide to the extracellular matrix or other cell compartment. More preferably, the genetic sequence encoding targeting signal is placed in-frame at the 5'-terminus or the 3'-terminus, but most preferably at the 5'-terminus, of the coding region of the nucleotide sequence which encodes the fusion polypeptide.

Methods for the production of a fusion polypeptide are well-known to those skilled in the art.

The recombinant EcR polypeptide subunit of the insect steroid receptor or EcR partner protein (USP polypeptide) subunit of the steroid receptor or USP polypeptide of the juvenile hormone receptor may be purified by standard techniques, such as column chromatography (using various matrices which interact with the protein products, such as ion exchange matrices, hydrophobic matrices and the like), affinity chromatography utilizing antibodies specific for the protein or other ligands such as dyes or insect steroids which bind to the protein.

Wherein the recombinant polypeptide is expressed as a fusion polypeptide, it is also possible to purify the fusion polypeptide based upon its properties (eg size, solubility, charge etc). Alternatively, the fusion polypeptide may be purified based upon the properties of the non-receptor moiety of said fusion polypeptide, for example substrate affinity. Once purified, the fusion polypeptide may be cleaved to release the intact polypeptide of the invention.

Alternatively, proteins may be synthesized by standard protein synthetic techniques as are well known in the art.

In a preferred embodiment, the recombinant or isolated polypeptides of the invention are provided as a precipitate or crystallized by standard techniques, preferably for X-ray crystal structure determination.

The three-dimensional structure of the polypeptide of the invention or a holoreceptor comprising same or a fragment of said polypeptide or holoreceptor is particularly useful for identifying candidate insecticidal agents which mimic ligands that bind to said three-dimensional structure and/or modulate the ability of insect steroids to bind thereto and activate the receptor (see, for example, Von Itzstein et al., 1993; and Bugg et al., 1993).

According to this embodiment, the EcR polypeptides of the invention or ligand binding domains thereof, or their complexes with EcR partner proteins or ligand binding domains thereof, which confer enhanced affinity for insect steroid response elements or partner proteins (USP polypeptides) or ligands, are particularly useful to model the three-dimensional structure of the receptor ligand-binding region. In this manner, insecticidal compounds may be produced which bind to, or otherwise interact with, the ligand-binding region of the receptor and/or preferably interfere with ligand binding. In the same way, compounds may be developed which have a potentiated interaction with the insect steroid receptor over and above that of the physiological insect steroid which binds to the receptor.

Accordingly, a still further aspect of the invention provides a method of identifying a candidate insecticidally-active agent comprising the steps of:

a) expressing a USP polypeptide of a juvenile hormone receptor or a fragment thereof which includes the ligand-binding region, optionally in association with an EcR polypeptide of a steroid receptor or ligand binding domain thereof, and optionally in association with an insect steroid or analogue thereof, so as to form a complex;

b) purifying or precipitating the complex;

c) determining the three-dimensional structure of the ligand binding domain of the complex; and d) identifying compounds which bind to or associate with the three-dimensional structure of the ligand binding domain, wherein said compounds represent candidate insecticidally-active agents.

Standard procedures are used to determine the three dimensional structure of the receptor polypeptides of the invention, for example using X-ray crystallography and/or nuclear magnetic resonance analysis (see, for example, Bugg et al., 1993; Von Itzstein et al., 1993).

Insecticidally-active agents contemplated herein include synthetic chemicals that mimic one or more ligands of the holoreceptor or its polypeptide subunit, or the ligand-binding region of said holoreceptor or subunit, thereby modulating binding of steroids to said holoreceptor or subunit. Preferred insecticidally-active agents include bisacylhydrazines, iridoid glycosides or other non-steroidal modulators of ecdysteroid receptors or insect juvenile hormone receptors. Additionally, because the EcR partner protein (USP polypeptide) subunits of insect steroid receptors, and the USP polypeptides of insect juvenile hormone receptors, bind insect juvenile hormones, a sesquiterpenoid group of ligands that regulate developmental transitions in insects (see Jones and Sharp, 1997), compounds which interfere with the binding of juvenile hormone are also candidate insecticides.

A further aspect of the present invention provides a method of identifying a modulator of insect steroid receptor-mediated gene expression or insect juvenile hormone receptor-mediated gene expression comprising:

(i) assaying the expression of a reporter gene in the presence of a recombinant or isolated insect steroid receptor polypeptide or a juvenile hormone receptor polypeptide of the invention and a potential modulator; and (ii) assaying the expression of a reporter gene in the presence of a recombinant or isolated insect steroid receptor polypeptide or a juvenile hormone receptor polypeptide of the invention and without said potential modulator; and (ii) comparing expression of the reporter gene in the presence of the potential modulator to the expression of a reporter gene in the absence of the potential modulator, wherein said reporter gene is placed operably under the control of a steroid response element (SRE) to which said insect steroid receptor binds or a promoter sequence comprising said SRE.

In the present context, a "modulator" is a compound or molecule that agonises or antagonises the binding properties and/or biological activity of a receptor polypeptide or holoreceptor. Preferred modulators according to this embodiment include those synthetic compounds that are suitable for use as insecticidally-active agents described supra.

The reporter gene may be any gene, the expression of which may be monitored or assayed readily. Preferably, the reporter gene is a structural gene that encodes a peptide, polypeptide or enzyme that is assayed readily by enzymic or immunological means, for example the β-galactosidase, β-glucuronidase, luciferase or chloramphenicol acetyltransferase (CAT) genes. Alternatively, the reporter gene may be a gene which encodes an immunologically-detectable protein, for example a FLAG peptide, poly-lysine peptide or poly-histidine peptide.

Standard methods are used to assay the expression of the reporter gene.

This embodiment of the invention may be applied directly to the identification of potential insecticidally-active compounds or alternatively, modified for such purposes by assaying for the binding (direct or indirect) of the recombinant or isolated insect steroid receptor polypeptide or a juvenile hormone receptor polypeptide of the invention to a steroid response element (SRE), rather than by assaying for reporter gene expression. According to this alternative embodiment, the binding assayed in the presence or absence of a potential insecticidally-active compound is compared, wherein a difference in the level of binding indicates that the candidate compound possesses potential insecticidal activity.

In addition, substances may be screened for insecticidal activity by assessing their ability to bind, in vivo or in vitro, to the intact ecdysone receptor or alternatively, the ligand-binding regions of the EcR polypeptide subunit of the ecdysone receptor (eg. SEQ ID NO:2 and/or SEQ ID NO:6 and/or SEQ ID NO:10) and/or the EcR partner protein (USP polypeptide) of the ecdysone receptor (eg. SEQ ID NO:4 and/or SEQ ID NO:12 and/or SEQ ID NO:14). Competition assays involving the native insect steroid may be employed to assess insecticidal activity.

The performance of this embodiment may, for example, involve binding the insect steroid receptor polypeptide to a support such as a plurality of polymeric pins, whereafter the polypeptide resident on the plurality of pins is brought into contact with candidate insecticidal molecules for screening. The molecules being screened may be isotopically labelled so as to permit ready detection of binding. Alternatively, reporter molecules may be utilized which bind to the insect steroid receptor candidate molecule complex. Alternatively, compounds for screening may be bound to a solid support, such as a plurality of pins which are then reacted with the thermostable insect steroid receptor or complex with a partner protein. Binding may, for example, be determined again by isotopic-labelling of the receptor, or by antibody detection or use of another reporting agent.

In an alternative embodiment, insecticidally-active agent are identified using rational drug design, by expressing a USP polypeptide of a juvenile hormone receptor or a fragment thereof which includes the ligand-binding region, optionally in association with an EcR polypeptide of a steroid receptor or ligand binding domain thereof, and optionally in association with an insect steroid or analogue thereof, so as to form a complex, determining the three-dimensional structure of the ligand binding domain of the complex, and identifying compounds which bind to or associate with the three-dimensional structure of the ligand binding domain, wherein said compounds represent candidate insecticidally-active agents.

The methods described herein for identifying modulators of gene expression and insecticidal compounds, may be performed using prokaryotic or eukaryotic cells, cell lysates or aqueous solutions.

A further aspect of this invention accordingly relates to synthetic compounds derived from the three dimensional structure of EcR polypeptides and/or EcR partner protein (USP polypeptide) subunits of insect steroid receptors, or fragments thereof, or insect steroid receptors or fragments thereof, or USP polypeptides of insect juvenile hormone receptors or fragments thereof, which compounds are capable of binding to said receptors which have the effects of either inactivating the receptors (and thus acting as antagonists) or potentiating the activity of the receptor.

By "derived from" it is meant that the compounds are based on the three dimensional structure of the aforementioned proteins, that is, synthesized to bind, associate or interfere with insect steroid binding or juvenile hormone binding.

The compounds may bind strongly or irreversibly to the ligand binding site or another region of the receptor or USP and act as agonists or antagonists of insect steroids, or juvenile hormone binding, or otherwise interfere with the binding of ligand, such that ecdysteroids or juvenile hormones. Such compounds would have potent insecticidal activity given the key role of insect steroids, or juvenile hormone, in insect physiology and biochemistry. Such compounds would also possess a unique specificity.

This invention is also described with reference to the following non-limiting examples.

Example 1

Construction of a Plasmid (pSV40-EcR) Expressing the EcR Polypeptide Subunit of the *D. Melanogaster* Ecdysone Receptor A 3110 base-pair Fsp1-HindIII fragment was excised from a cDNA encoding the EcR polypeptide subunit of the *D. melanogaster* ecdysone receptor (Koelle et al., 1991), the excised sequence comprising the complete 2634 base pair coding region and 214 base pairs of 5'-leader sequence and 258 base pairs of 3'-untranslated sequence. The fragment was ligated into the BamH1 site of the expression plasmid pSG5 (Greene et al, 1988) to produce the expression plasmid pSV40-EcR, wherein expression of the EcR polypeptide subunit of the *Drosophila melanogaster* ecdysone receptor is placed operably under the control of the SV40 promoter sequence.

Example 2

Construction of the Reporter Plasmid p(EcRE)$_7$-CAT

The reporter plasmid p(EcRE)$_7$-CAT was constructed by insertion of seven copies of the hsp27 ecdysone response element, containing a central 13 base pair palindromic ecdysone response element (EcRE), derived from the hsp27 gene (Riddihough and Pelham, 1987) into the HindIII site of the plasmid pMMTV-CAT (Hollenberg and Evans, 1988), 93 base pairs upstream of the transcription start site of the MMTV promoter, thereby operably connecting expression of the chloramphenicol acetyltransferase structural gene to regulation by an insect receptor which binds to the hsp27 ecdysone response element.

Example 3

Cell Culture and Transient Transfection

Chinese hamster ovary (CHO) cells were maintained in 50% (v/v) Dubbecco's modified Eagle's medium (DMEM) and 50% (v/v) Hamm F12 nutrient mixture (GIBCO) supplemented with 10% (v/v) foetal bovine serum. Transfection was carried out by the DNA-calcium phosphate co-precipitation method (Ausubel et al, 1992). One day before transfection with the plasmids described in Examples 1 and/or 2, or other expression plasmids, CHO cells were plated out at 5-8×10$^5$ cells per 6 cm diameter culture dish in the above DMEM/F12 medium. Three hours before the addition of the DNA-calcium phosphate co-precipitate, the cells were washed with phosphate buffered saline (PBS;

Sambrook et al., 1989) and cultured in fresh DMEM plus 10% (v/v) foetal bovine serum. The cells were incubated in the presence of the co-precipitate for eighteen hours before excess DNA was removed by washing with PBS. The cells were then cultured for another day in DMEM/F12 supplemented with 10% (v/v) foetal bovine serum with or without added ponasterone A (PNA), before harvesting. Cells were washed with PBS, harvested by mechanical scraping in 0.25 M Tris-HCl (pH 7.8), and disrupted by three freeze-thaw cycles.

All transfections included, in addition to expression and reporter plasmids, a β-galactosidase-expressing plasmid designated pPgK-LacZ (McBurney et al, 1991), which served as an internal control for the efficiency of transfection, and pUC18 DNA in an amount sufficient to produce 10 μg total DNA per culture dish.

The chloramphenicol acetyltransferase (CAT) and β-galactosidase activities encoded by the reporter genes present in the reporter plasmids were assayed as described in Sambrook et al, (1989). Cells that were co-transfected with p(EcRE)$_7$-CAT and pSV40-EcR clearly showed induction of CAT activity in the presence of PNA, showing 50 units of activity. Controls showed negligible activity.

We have observed that the ecdysone receptor can lead to stimulation of expression from an ecdysone responsive promoter in some cell types, for example in CHO cells, but not in CV-1 cells. Whilst not being bound by any theory or mode of action, this may reflect a cell-type specific distribution of at least one other transcription factor essential for ecdysone responsiveness. To determine cell types suitable for expressing reporter genes under the control of the steroid receptor of the present invention, the cell-type specificity of ecdysone-responsive gene expression is assayed in cell-free transcription lysates derived from several target cell lines. Additionally, by fractionating and/or isolating the nuclear proteins of cell lines that express the reporter genes and supplementing lysates derived from non-expressing cell lines with such nuclear protein fractions or isolated proteins, any essential auxiliary factors are defined and the genes encoding them cloned. Co-transfection of the receptor-encoding genes with genes encoding such auxiliary factors removes limitations imposed by cell-type restricted ecdysone responsiveness.

Example 4

Testing the Effect of Temperature on Transient Expression

To determine whether the *D. melanogaster* ecdysone receptor polypeptide is stable at physiological temperatures above about 30° C., CHO cells were transfected as described in Example 3, with the plasmid pSV40-EcR and the reporter plasmid p(EcRE)$_7$-CAT in the presence of PNA, at 30° C. and 37° C.

Briefly, CHO cells were plated out at 37° C. sixteen to twenty hours before transfection. After washing away the DNA, the cells were cultured for two hours in fresh medium with or without hormone and the dishes divided into duplicate sets. One set was cultured for another day at 37° C. before harvesting for CAT and β-galactosidase assays. The other set was cultured for three days at 30° C. before assaying enzyme activities. Results indicated a reduction in the fold-induction of gene expression regulated by the *D. melanogaster* ecdysone receptor polypeptide at 37° C., compared to the fold-induction at 30° C., as shown in Table 1.

Example 5

Attempted Screening of an *L. cuprina* Genomic DNA Library to Isolate Genes Encoding the EcR Polypeptide Subunit of the *L. cuprina* Ecdysone Receptor A 627 bp Eco-Kpn I fragment encompassing the DNA-binding domain of the EcR polypeptide subunit of the *D. melanogaster* ecdysone receptor was isolated, radioactively labelled and used to screen a *L. cuprina* genomic library constructed in bacteriophage lambda (prepared by CSIRO, division of Entomology, Canberra, Australia). In the first round of screening, twenty-four regions of the plates showed potential positive hybridization to the *D. melanogaster* probe. However, second-round screening of these 24 first round positive plaques failed to yield any plaque giving a reproducible positive signal when hybridized to the *D. melanogaster* probe.

TABLE 1

| pSV40-EcR | PNA | Fold-induction of expression | |
|---|---|---|---|
| (μg/dish) | (μM) | 37° C. | 30° C. |
| 2.5 | 20 | 14X | 35X |
|  |  | 59X | 54X |
| 0.5 | 20 | 8X | 26X |
|  |  | 47X | 33X |
| 0.1 | 20 | 1.6X | 25X |
|  |  | 9.0X | 39X |

Example 6

Cloning and Characterization of a cDNA Molecule Encoding the EcR Polypeptide of the *L. cuprina* Ecdysone Receptor Rationale for Amplification Primer Design The nucleotide sequences of the primers Rdna3 (SEQ ID NO: 15) and Rdna4 (SEQ ID NO:16) were derived from the amino acid sequence conserved between the DNA-binding domains of the EcR polypeptide subunits of the *D. melanogaster* and *C. tentans* ecdysone receptors. However, amino acid sequences homologous to two other members of the steroid receptor superfamily of *D. melanogaster*, *Drosophila* hormone receptor 3 (DHR3; Koelle, et al., 1991) and *Drosophila* early gene (E75; Segraves and Hogness, 1990) were excluded from the primer designs, to reduce the possibility of amplifying the *L. cuprina* homologues of genes encoding DHR3 and/or E75 by PCR.

Amplification Primers and PCR Conditions

A 105 base pair DNA fragment, encoding the DNA-binding domain of the EcR polypeptide subunit of the *L. cuprina* ecdysone receptor, was amplified from the *L. cuprina* genome by PCR, by using the following degenerate primers:

Rdna3 (32mer with EcoRI site):

5'-CGGAATTCCGCCTCTGGTTA(C/T)CA(C/T)TA(C/T)AA(C/T)GC 3' (i.e. SEQ ID NO:15); and

Rdna4 (32mer with BamHI site):

5'-CGCGGATCC(G/A)CACTCCTGACACTTTCG(C/T)CTCA 3' (i.e. SEQ ID NO:16).

Amplification reactions employed TaqI DNA polymerase (Promega) and the following amplification conditions:

| | |
|---|---|
| cycle 1: | 97° C./5 minutes, 50° C. hold; add polymerase 50° C./ 5 minutes; |
| cycles 2-3: | 72° C./3 minutes, 94° C./1 minute, 50° C./1 minute; |
| cycles 4-43: | 72° C./3 minutes, 94° C./1 minute, 55° C./1 minute; |
| cycle 44: | 72° C./10 minutes. |

To facilitate cloning of the amplified fragments for use as hybridisation probes, the 5' end of primer Rdna3 contained an EcoRI site and the 5' end of primer Rdna4 contained a BamHI site. The amplified *L. cuprina* gene fragments were cloned into pBluescript SK+, following digestion using the enzymes EcoRI and BamHI, purification of the digested DNA by agarose gel electrophoresis and electro elution of the product band.

Hybridisation Probe Preparation

For probe preparation, the insert was cut out of the pBluescript SK+ vector using EcoRI and BamHI, and $^{32}$P-labelled using the GIGAprime DNA Labelling Kit (Bresatec Limited, Adelaide, Australia) essentially according to the manufacturer's instructions, except that random primers were replaced with the specific primers Rdna3 and Rdna4 (see above). Unincorporated label was removed by size exclusion chromatography over Biogel-P60 (Biorad Ltd, Sydney, Australia). The probe was used at $10^6$ cpm/ml in hybridizations.

Construction and Screening of *L. cuprina* cDNA Libraries

Two independent *L. cuprina* cDNA libraries derived from late third instar *L. cuprina* larvae were prepared by random priming and oligo-dT priming respectively, and cloned into the EcoRI site of the Lambda/ZapII vector (Stratagene). The primary libraries generated were subsequently amplified according to the manufacturer's instructions, using standard protocols.

Both cDNA libraries generated are superior to existing *L. cuprina* libraries in terms of their phage titre (i.e. pfu/ml) and insert sizes (0.5-4 kbp in both cases). In particular, the primary oligo-dT primed library comprised $4.7 \times 10^6$ pfu, whilst the amplified oligo-dT primed library comprised $7.5 \times 10^{10}$ pfu/ml; the primary random-primed library comprised $1.3 \times 10^6$ pfu, whilst the amplified random-primed library comprised $3.4 \times 10^{10}$ pfu/ml.

The prepared cDNA libraries were screened by lifting 500,000 plaques from each library in duplicate on to Hybond N membranes (Amersham) and hybridizing same under low stringency conditions to the $^{32}$P-labelled amplification product produced using the primers Rdna3 and Rdna4 (see above). In particular, hybridisations were performed for twenty four hours at 37° C. in a hybridisation solution comprising 42% (w/v) formamide; 5×SSPE solution; 5×Denhardt's solution; and 0.1% (w/v) sodium dodecyl sulphate, as described essentially by Ausubel et al, (1992) and/or Sambrook et al. (1989). The membranes were then washed at 37° C. in 2×SSC solution containing 0.1% (w/v) sodium dodecyl sulphate. Following washing, positive plaques were detected by autoradiography, using XOMAT-AR film (Kodak) for two to three days, at −70° C.

Two positive-hybridising plaques were obtained from screening of the random-primed library (containing cDNA inserts comprising 561 base pairs and 1600 base pairs in length, respectively), and one positive-hybridising plaque was obtained from the screening of the oligo-dT primed library (containing a cDNA insert comprising approximately 3400 base pairs in length). pBluescript phagemids containing cDNA inserts were excised in vivo from these positive plaques using the Exassist Helper Phage system (Stratagene).

The nucleotide sequences of the isolated cDNA clones were obtained using the USB Sequenase Version 2.5 Kit. Sequence data obtained indicated that the 561 bp and 1600 bp cDNAs encode amino acid sequences comprising the important DNA-binding domain and the hormone-binding domain of the EcR polypeptide subunit of the *L. cuprina* ecdysone receptor, whilst the 3400 bp cDNA comprises an entire 2274 bp open reading frame encoding the EcR polypeptide subunit of the *L. cuprina* ecdysone receptor. Accordingly, the 3400 bp cDNA is a full-length cDNA clone. The nucleotide sequence of the open reading frame and 3'-untranslated region is set forth herein as SEQ ID NO: 1. The derived amino acid sequence of the EcR polypeptide subunit of the *L. cuprina* ecdysone receptor encoded by this open reading frame is set out in SEQ ID NO: 2.

Example 7

First Attempt at Cloning and Characterization of a cDNA Molecule Encoding the EcR Polypeptide of the *M. persicae* Ecdysone Receptor Direct screening of a *M. persicae* cDNA library was not effective in isolating a full-length cDNA encoding the EcR polypeptide of the *M. persicae* ecdysone receptor.

DNA encoding the DNA-binding domain of the EcR polypeptide of the *M. persicae* ecdysone receptor was isolated successfully, by amplification as described in Example 6 for the amplification of the homologous *L. cuprina* fragment. The amplified DNA was cloned into pBluescript SK+ and the nucleotide sequence of the cloned insert was obtained using the USB Sequenase version 2.0 Kit, as described in Example 6.

Based upon the nucleotide sequence of the amplified DNA fragment, two authentic primers were synthesized as follows:

```
Mdna1 (23mer):           (i.e. SEQ ID NO:17)
5'-GCCTCGGGGTATCACTATAACGC-3'; and Mdna2 (23mer):           (i.e. SEQ ID NO:18)
5'-GCACTCCTGACACTTTCGTCTCA-3'.
```

Hybridisation Probe Preparation

For *M. persicae* probe preparation, the amplified 105 bp DNA insert was excised from the pBluescript SK+ vector using EcoRI and BamHI, and $^{32}$P-labelled using the GIGAprime DNA Labelling Kit (BresaGen Limited, Adelaide, Australia) essentially according to the manufacturer's instructions, except that random primers were replaced with the specific primers Mdna1 and Mdna2 (see above). Unincorporated label was removed by size exclusion chromatography over Biogel-P60 (Biorad Ltd, Sydney, Australia). The probe was used at $10^6$ cpm/ml in hybridizations.

Construction and Screening of *M. persicae* cDNA Libraries:

Two independent *M. persicae* cDNA libraries derived from late third instar *M. persicae* larvae were prepared by random priming and oligo-dT priming respectively, and cloned into the EcoRI site of the Lambda/ZapII vector (Stratagene). The primary libraries generated were subsequently amplified according to the manufacturer's instructions, using standard protocols.

Both cDNA libraries generated are superior to existing *M. persicae* libraries in terms of their phage titre (i.e. pfu/ml) and insert sizes (0.5-4 kbp in both cases). In particular, the primary oligo-dT-primed library comprised $1\times10^7$ pfu, whilst the amplified oligo-dT primed library comprised $1\times10^{10}$ pfu/ml; the primary random-primed library comprised $1\times10^6$ pfu, whilst the amplified random-primed library comprised $2\times10^{11}$ pfu/ml.

Additionally, a further cDNA library was produced in the Lambda ZAP Express insertion vector (Stratagene). To produce this library, cDNA derived from late third instar *M. persicae* larvae was prepared by oligo-dT priming and cloned directionally into EcoRI-XhoI digested vector DNA. The primary library comprised $1\times10^6$ pfu, whilst the amplified oligo-dT primed library comprised $1\times10^9$ pfu/ml, with insert sizes in the range 0.5->4 kbp.

The random-primed *M. persicae* cDNA phage library was screened as described in Example 6, using the *M. persicae* hybridisation probe prepared as described above.

A single positive-hybridising plaque was isolated and sequenced according to standard procedures. The nucleotide sequence of this clone is set forth herein as SEQ ID NO:5. This cDNA clone comprises a 585 bp protein-encoding sequence which encodes the DNA-binding domain of a EcR polypeptide of a putative *M. persicae* ecdysone receptor. The amino acid sequence encoded by this partial cDNA clone is set forth herein as SEQ ID NO: 6.

Example 8

Second Attempt at Cloning and Characterization of a cDNA Molecule Encoding the EcR Polypeptide of the *M. persicae* Ecdysone Receptor Hybridisation Probe Preparation Further hybridisation probes specific for the EcR polypeptide of the *M. persicae* ecdysone receptor were generated using PCR from the Lambda ZAPII oligo dT-primed library using primers AP1 and AP2. The forward primer AP1 was designed to anneal to nucleotide sequences of the partial cDNA (SEQ ID NO: 5) encoding part of the first zinc finger motif present in the DNA-binding domain. The reverse primer, AP2, was adapted from degenerate primers designed to anneal to nucleotide sequences complementary to those encoding an EcR ligand binding domain (Kamimura et al., 1996). The nucleotide sequences of primers AP1 and AP2 are as follows:

```
Primer AP1:                           (SEQ ID NO:19)
5'-TCGTCCGGTTACCATTACAACGC-3'; and Primer AP2:                           (SEQ ID NO:20)
5'-TAGACCTTTGGC(A/G)AA(C/T)TC(A/G/C/T)ACAAT-3'
```

The PCR reaction mixture contained 4 µl of each primer (50 pm/µl), 5 µl of deoxynucleotide triphosphate mix (2 mM), 1 µl of aphid oligo dT primed Lambda ZAPII cDNA library, 1 µl of recombinant Pfu DNA Polymerase (5 units/µl, Stratagene®), 5 µl of 10×Pfu buffer (Stratagene®) and 30 µl of MilliQ water. The Pfu polymerase was used in this reaction because it possesses proof-reading activity, which reduces the possibility of misincorporation of nucleotides. The PCR conditions included 42 cycles, each cycle comprising annealing at 55° C., extension at 72° C. and melting at 94° C.

The major amplification product obtained in this reaction was gel-purified, kinased and ligated into the SmaI site of pUC18.

To screen *M. persicae* cDNA libraries, the cloned amplification product was digested to generate two non-overlapping probes, designated "EcR probe 1" (i.e. SEQ ID NO:7) and "EcR probe 2" (i.e. SEQ ID NO:8). In this regard, digestion of the cloned product with SphI produced a DNA fragment comprising a nucleotide sequence specific for a region encoding the DNA-binding domain (EcR probe 1; SEQ ID NO: 7), whilst digestion with SphI/EcoRI produced a DNA fragment comprising a nucleotide sequence having homology to a region encoding a putative linker domain, designated domain D, and the 5'-end of a putative hormone-binding domain, present in the EcR polypeptide of the insect ecdysone receptors (EcR probe 2, SEQ ID NO: 8).

EcR probe 1 and EcR probe 2 were labelled with [$\alpha$-$^{32}$P] dATP in a reaction catalysed by Klenow fragment. All reagents were components of a GIGAprime DNA labelling kit (BresaGen Limited, Adelaide, Australia), except that the random primers were replaced with specific oligonucleotides synthesized to be complementary to the ends of EcR probe 1 and EcR probe 2.

Screening of *M. persicae* cDNA Libraries 480,000 plaques from the oligo dT primed Lambda Zap Express cDNA library (Example 7) were screened as described above, using EcR probe 1. This approach yielded about 300 positive clones. Positive-hybridising clones were pooled and rescreened separately using EcR probe 1 and EcR probe 2, on duplicate lifts. Only four plaques were identified which hybridised to both probes. One of these was found by sequencing to contain a full-length cDNA encoding the EcR polypeptide of the *M. persicae* ecdysone receptor. The nucleotide sequence of the open reading frame of this cDNA is set forth herein as SEQ ID NO: 9. The derived amino acid sequence of the EcR polypeptide subunit of the *M. persicae* ecdysone receptor encoded by this open reading frame is set out in SEQ ID NO: 10.

Example 9

In Vivo Function of Recombinant EcR Polypeptides of the *L. cuprina* Ecdysone Receptor Construction of Plasmid pF3

Plasmid pF3 was constructed in four steps as follows:

First, plasmid p5S1, comprising the full-length cDNA encoding the EcR polypeptide of the *L. cuprina* ecdysone receptor, was digested with EarI and a 3' EarI cDNA fragment thus generated, encoding the C-terminal end of the EcR polypeptide of the *L. cuprina* ecdysone receptor, was end-filled and sub-cloned into the HindIII site of pUC19, to construct plasmid pEAR. In plasmid pEAR, the 3' end of the cDNA was oriented towards the KpnI site of the pUC19 vector.

Second, plasmid p5S1 was also digested separately with:

(1) ApoI and PstI, to isolate the 5' end of the cDNA as a 179 bp fragment (fragment A);

(2) PstI and SpeI, to isolate a 1650 bp cDNA fragment (fragment B); and (3) SpeI and BglII, to isolate a 203 bp fragment (fragment C).

Third, plasmid pEAR was digested with BglII and KpnI, to isolate the 3' end of the cloned cDNA fragment therein as a 313 bp fragment (fragment D).

Fourth, DNA fragments A, B, C and D were each isolated by agarose electrophoresis and ligated together into pBluescriptSK+, which had been digested with EcoRI and KpnI, to produce plasmid pF3.

Plasmid pF3 thus contains the complete open reading frame of the cDNA encoding the EcR polypeptide of the *L. cuprina* ecdysone receptor, as a 2368 bp fragment located between two BamHI sites.

Construction of Plasmid pSGLcEcR and Plasmid pLcK8

Plasmid pSGLcEcR was constructed by cloning the 2368 bp BamHI fragment from pF3, into the BamHI site of the mammalian expression vector pSG5 (Stratagene). Plasmid pLcK8 is a clone of pSGLcEcR.

Construction of Plasmid pSGDmEcR

Plasmid pSGDmEcR is identical to plasmid pSV40-EcR (Example 1) comprising the EcR polypeptide of the *D. melanogaster* ecdysone receptor placed operably under control of the SV40 promoter.

Transfection of CHO Cells

CHO cells were co-transfected with a mixture comprising the following DNAs, lysed and assayed for CAT and β-galactosidase enzyme activity, as described in the preceding Examples:

(1) one of the expression plasmids designated pSGDmEcR, or pSGLcEcR, or the parental expression plasmid pSG5 as a negative control, at a concentration of 1 µg/ml; and (2) the CAT reporter plasmid p(EcRE)$_5$CAT at a concentration of 1 µg/ml; and (3) an independent LacZ reporter plasmid, pPGKLacZ, at a concentration of 1 µg/ml, included as a control to monitor transfection efficiency.

CAT reporter gene expression was induced with 10 µM or 50 µM Muristerone A. In control samples, cells received only the carrier ethanol in place of Muristerone A.

ELISA was used to quantify the synthesis of CAT and β-galactosidase enzymes, in extracts of cells forty eight hours after transfection. Account was taken of the variation between experiments, by normalizing the level of CAT enzyme to the level of β-galactosidase enzyme present in the same extract. Fold induction represents the normalized values for CAT gene expression in cells transfected with pSGDmEcR, pSGLcEcR or pSG5 in the presence of hormone divided by the normalized values for CAT gene expression in cells transfected with the same plasmid but in the absence of hormone. The average values of three independent experiments are shown in FIG. 1 and the error bars indicate standard error of the mean.

Figure 1:
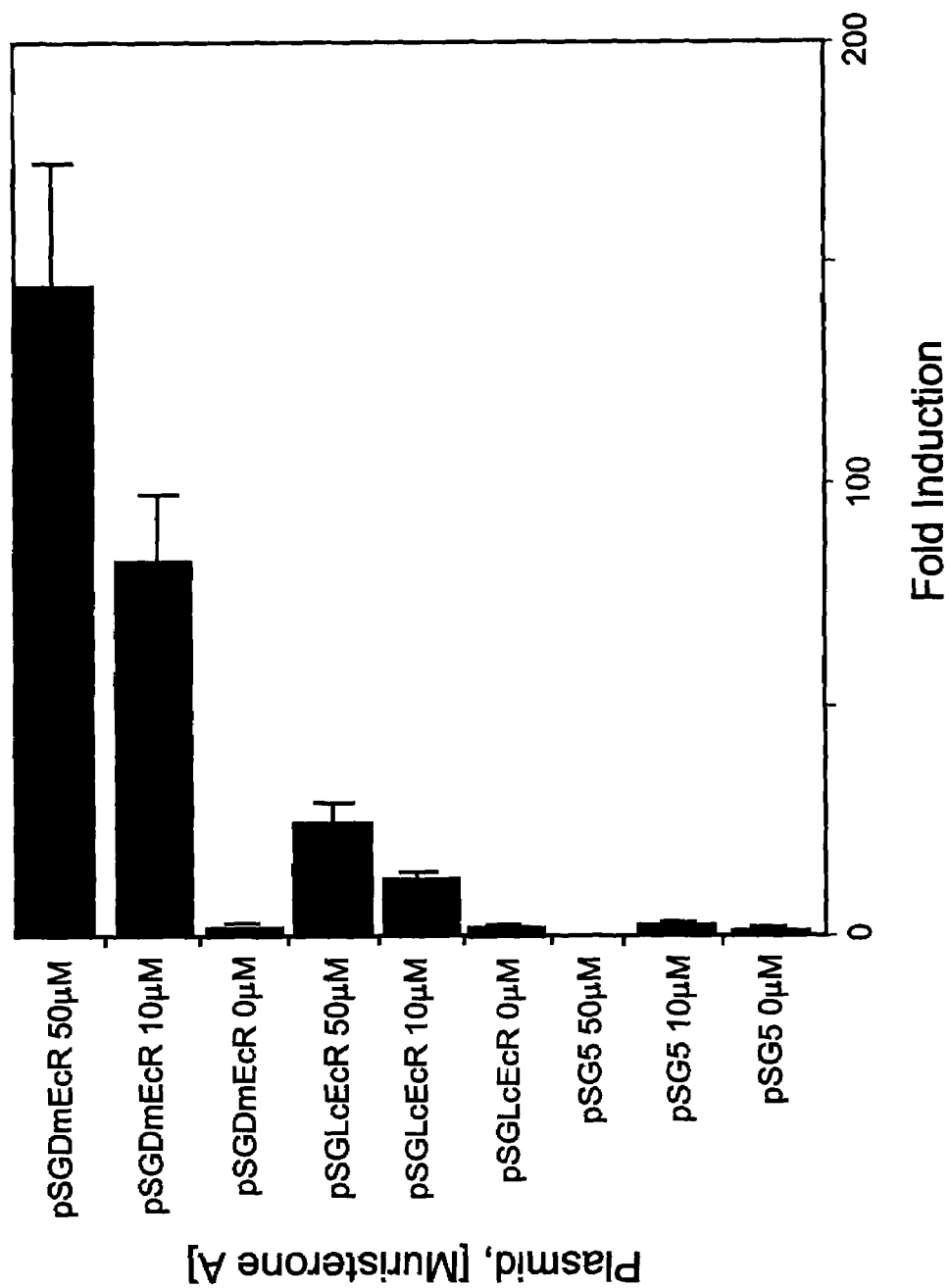

Data shown in FIG. 1 indicate that the EcR polypeptide of the *L. cuprina* ecdysone receptor from Example 3 is biologically active in vivo. CAT induction is observed at both 50 µM and 10 µm steroid (Muristerone A), with about 30 and 15 fold induction respectively. In view of the in vivo activity of the EcR polypeptide of the *L. cuprina* ecdysone receptor obtained according to this protocol, potential insecticidal substances acting by interaction with an insect steroid receptor, such as an ecdysone receptor, are screened by addition of the substances to the in vivo assay described herein. Substances are added in an amount from 0.05 µM to 100 µM. Candidate insecticidal compounds are identified by their ability to modulate the reporter gene expression which results from trans-activation by the EcR polypeptide of the *L. cuprina* ecdysone receptor.

Example 10

Chimeric EcR Polypeptides of Insect Ecdysone Receptors

Chimeric ecdysone receptors comprising regions derived from EcR polypeptides of ecdysone receptors of different species are produced and assayed for enhanced activity. In a particularly preferred embodiment, a chimeric ecdysone receptor is produced using the EcR polypeptides of the *D. melanogaster, M. persicae* and *L. cuprina* ecdysone receptors.

In one exemplification of this embodiment, plasmids pSGLD and pSGDL are produced comprising coding regions derived from the EcR polypeptides of the *D. melanogaster* and *L. cuprina* ecdysone receptors. In plasmid pSGLD, the 5'-end of the open reading frame of the *D. melanogaster* sequence, encoding the N-terminal portion of the EcR polypeptide of the *D. melanogaster* ecdysone receptor to the end of the DNA-binding domain of said polypeptide, is fused to the 3'-end of the open reading frame of the *L. cuprina* sequence, encoding the C-terminal portion of the EcR polypeptide of the *L. cuprina* ecdysone receptor, from the D domain and hormone-binding domain to the carboxyl terminus. In plasmid pSGDL, the 5'-end of the open reading frame of the *L. cuprina* sequence, encoding the N-terminal portion of the EcR polypeptide of the *L. cuprina* ecdysone receptor to the end of the DNA-binding domain of said polypeptide, is fused to the 3'-end of the open reading frame of the *D. melanogaster* sequence, encoding the C-terminal portion of the EcR polypeptide of the *D. melanogaster* ecdysone receptor, from the D domain and hormone-binding domain to the carboxyl terminus. These plasmids thus encode chimeric EcR polypeptides which form ecdysone receptor variants.

As shown in FIG. 2, chimeric EcR polypeptides of *L. cuprina* and *D. melanogaster* ecdysone receptors, comprising fusion polypeptides between the DNA-binding domains and hormone-binding domains of the base *L. cuprina* and *D. melanogaster* polypeptides, exhibit bioactivity when measured in the CAT assay described above. Significant bioactivity of the chimeric EcR polypeptides encoded by plasmids pSGLD and pSGDL, comparable to the bioactivity of the *D. melanogaster* base EcR polypeptide, is observed at both 10 µM and 50 µM concentrations of Muristerone A.

Example 11

Isolation and Characterisation of a Full-Length cDNA Encoding the EcR Partner Protein (USP Polypeptide) of the *L. cuprina* Ecdysone Receptor The EcR partner protein (USP polypeptide) subunit of the *L. cuprina* ecdysone receptor also functions alone as a USP polypeptide of the *L. cuprina* juvenile hormone receptor. A cDNA encoding both receptor polypeptide activities was isolated using PCR and hybridisation as follows.

Hybridisation Probe Preparation

A 150 base-pair probe, specific for genetic sequences encoding the EcR partner protein (USP polypeptide) subunit of insect ecdysone receptors and/or the USP polypeptide subunit of insect juvenile hormone receptors (SEQ ID NO:13), was isolated by PCR from *L. cuprina* genomic DNA using the degenerate primers described by Tzertzinis et al. (1994). The PCR reaction conditions were as described in Example 6, except that Pfu polymerase was used in place of TaqI polymerase.

The amplified DNA fragment was sub-cloned into EcoRI and ClaI double-digested pBluescript SK+ vector (Stratagene), after double-digestion of the fragment using the enzymes EcoRI and ClaI, purification of the amplified fragment by agarose gel electrophoresis, and electro elution of the product band. The nucleotide sequence of the probe was obtained using the USB Sequenase version 2.0 Kit (SEQ ID NO:13).

For probe preparation, the amplified *L. cuprina* DNA fragment was excised from the vector using EcoRI and SalI, gel purified and $^{32}$P-labelled using the GIGAprime DNA Labelling Kit (BresaGen Limited, Adelaide, Australia) essentially according to the manufacturer's instructions except that random primers were replaced with the two degenerate primers described by Tzertzinis et al. (1994) (see above). Unincorporated label was removed by size exclusion chromatography over Biogel-P60 (Biorad Ltd, Sydney, Australia). The probe was used at $10^6$ cpm/ml in hybridizations.

Screening of *L. cuprina* cDNA Libraries

The *L. cuprina* cDNA library described above (Example 6) was screened with the amplified probe as described in Example 6. The nucleotide sequence of the full-length open reading frame of this cDNA molecule and amino acid sequence therefor, are set forth herein as SEQ ID NO: 3 and SEQ ID NO: 4, respectively.

Example 12

Isolation and Characterisation of a Partial cDNA Encoding the EcR Partner Protein (USP Polypeptide) of the *M. persicae* Ecdysone Receptor The EcR partner protein (USP polypeptide) subunit of the *M. persicae* ecdysone receptor also functions alone as a USP polypeptide of the *M. persicae* juvenile hormone receptor. To isolate a partial cDNA encoding both receptor polypeptide activities, a 140 bp probe was amplified from M persicae genomic DNA, by PCR, using the two degenerate primers described by Tzertzinis et al. (1994) (see preceding Example). The PCR reaction conditions were as described in Example 6, except that Pfu polymerase was used in place of TaqI polymerase.

The amplified DNA fragment was sub-cloned into EcoRI and ClaI double-digested pBluescript SK+ vector (Stratagene), after double-digestion of the fragment using the enzymes EcoRI and ClaI, purification of the amplified fragment by agarose gel electrophoresis, and electro elution of the product band.

The nucleotide sequence of the insert in the pBluescript SK+ vector was obtained using automated fluorescent dye terminator sequencing (SUPAMAC, Sydney Australia).

Hybridisation Probe Preparation and Library Screening

For probe preparation the amplified *M. persicae* DNA insert was cut out of the pBluescript+ vector with EcoRI and SalI, gel purified and $^{32}$P-labelled using the GIGAprime DNA Labelling Kit (Bresatec Limited, Adelaide, Australia) essentially according to the manufacturer's instructions except that random primers were replaced with the degenerate primers described by Tzertzinis et al. (1994) (see preceding Example). Unincorporated label was removed by size exclusion chromatography over Biogel-P60 (Biorad Ltd, Sydney, Australia). The probe was used at $10^6$ cpm/ml in hybridizations to screen the *M. persicae* cDNA library as described in Examples 7 and 8.

The positive-hybridising clones were plaque-purified and sequenced using standard procedures as described herein. The nucleotide sequence of the open reading frame of the full-length cDNA encoding the partner protein (USP polypeptide) subunit of the *M. persicae* ecdysone receptor or the USP polypeptide of the *M. persicae* juvenile hormone receptor is set forth herein as SEQ ID NO: 11. The derived amino acid sequence of this open reading frame is set forth as SEQ ID NO:12.

Example 13

A Construct for the Baculovirus-Directed Co-Expression of Functional Ligand-Binding Regions of the EcR Polypeptide and Partner Protein (USP Polypeptide) of the *D. melanogaster* Ecdysone Receptor A vector was prepared to facilitate the baculovirus-directed co-expression of ligand-binding regions derived from the EcR polypeptide and partner protein (USP polypeptide) of the *D. melanogaster* ecdysone receptor, the protein products of which associate on co-expression to form a functional hormone-binding complex. The associated proteins are then used in high through-put assays or three-dimensional structural analysis. We have found that the ligand-binding domain, together with most of the linker domain of the EcR polypeptide subunit and of the EcR partner protein (USP polypeptide), are sufficient to associate to form a functional hormone-binding complex.

1. Isolation of the Ligand-Binding Region and Linker Region of the EcR Polypeptide of the *D. melanogaster* Ecdysone Receptor.

A Sac I-HindIII fragment encoding most of the linker (domain D) and all of the ligand-binding domain (domains E and F) of the EcR polypeptide of the *Drosophila melanogaster* ecdysone receptor was excised from a plasmid comprising DNA encoding the complete EcR polypeptide (Koelle et al. 1991). The excised fragment was cloned into SacI-HindIII-digested expression vector pQE31 (Qiagen), to produce the plasmid vector pQE31DmECR.

2. Construction of a Baculovirus Expressing the Linker Regions of EcR and USP Polypeptides A baculovirus was constructed for the co-expression in insect cells of:
  (i) a cDNA region comprising a nucleotide sequence which encodes at least the ligand-binding domain and much of the linker domain of the EcR polypeptide of the *D. melanogaster* ecdysone receptor isolated as described at paragraph (1) above; and
  (ii) a cDNA region comprising a nucleotide sequence which encodes at least the ligand-binding domain and much of the linker domain of the partner protein (USP polypeptide) of the *D. melanogaster* ecdysone receptor.

To produce this baculovirus, a EcoR I-HindIII fragment was excised from pQE31DmECR, said fragment encoding an oligo-His tag, and most of the linker domain, together with all of the ligand-binding domain of EcR polypeptide. This EcoR I-HindIII fragment was ligated into EcoR I-HindIII cleaved pFastBacDUAL, to produce the plasmid pDmEcR.DUAL. To insert gene sequences specific for the partner protein (USP polypeptide), the HindIII-NsiI fragment encoding most of the linker and all of the ligand-binding domain of the partner protein (USP polypeptide) was excised from a full-length cDNA clone in plasmid pZ7-1 (supplied by Vince Henrich) and ligated into NcoI- NsiI cleaved pDmEcR.DUAL. A nucleotide sequence encoding a "FLAG" peptide was subsequently incorporated upstream of, and in the same reading frame as, the nucleotide sequence encoding the linker and ligand-binding regions of the partner protein (USP polypeptide), by ligation into the unique SmaI site, thereby producing the plasmid pDmEcR.USP.DUAL. Plasmids containing the FLAG-encoding nucleotide sequence in the correct orientation were selected by nucleotide sequence determination.

The segment of pDmEcR.USP.DUAL which encodes the tagged linker and ligand-binding regions of the EcR polypeptide and partner protein (USP polypeptide) sequences, placed operably under the control of polyhedrin and p10 promoters, respectively, was recombined into a baculovirus genome, by employing the Tn7 transposition system (Luckow et al, (1993). The polypeptide products were then co-expressed in insect Sf21 and Sf9 cells, where they associated into a functional complex.

Expression of the tagged linker and ligand-binding regions of the EcR polypeptide and partner protein (USP polypeptide) sequences was examined by immunoblot analysis of extracts derived from insect Sf21 cells infected with the recombinant baculovirus, employing antibodies directed against the oligo-His and FLAG tags. This analysis detected bands on immunoblot analysis of approximately the predicted sizes for the expressed tagged linker and ligand-binding regions of the EcR polypeptide and partner protein (USP polypeptide).

The protein detected by anti-oligo-His-antibodies was enriched by affinity purification on nickel-NTA resin (Qiagen), and the FLAG-labelled protein was affinity-purified using FLAG M2 Affinity Gel (Kodak). It was further demonstrated that the oligo-His-tagged EcR polypeptide and the FLAG-tagged EcR partner protein (USP polypeptide) bound as a hetero-oligomeric complex to FLAG M2 Affinity Gel (Kodak).

Furthermore, binding assays, performed using a modification of the method of Yund et al (1978), demonstrated a highly-significant increase in the binding of the a labelled ecdysone analogue, [$^3$H]ponasterone A, in cells infected by the recombinant baculovirus, compared to the binding observed for the naturally-occurring ecdysone holoreceptor in *L. cuprina* embryos. In contrast, cells infected by a control virus displayed neither antibody-positive bands on western analysis, nor specific binding of [$^3$H]ponasterone A, above background levels. These data indicate correct folding and association of the variant polypeptides comprising the linker and ligand-binding regions of the *D. melanogaster* EcR polypeptide and *D. melanogaster* partner protein (USP polypeptide). The correctly-folded and associated complex formed by the truncated Ecr polypeptide and truncated EcR partner protein (USP polypeptide), is used for X-ray and NMR structural analysis and for high-throughput screens.

Example 14

Construct for the Baculovirus-Directed Co-Expression of Functional Ligand-Binding Regions of the EcR Polypeptide and Partner Protein (USP Polypeptide) of the *L. cuprina* Ecdysone Receptor A vector for the baculovirus-directed co-expression of ligand-binding domains derived from the EcR polypeptide and partner protein (USP polypeptide) of the *L. cuprina* ecdysone receptor was prepared essentially as described in the preceding Example.

1. Isolation of the Ligand-Binding Region and Linker Region of the EcR Polypeptide of the *L. cuprina* Ecdysone Receptor.

A SphI-KpnI fragment encoding most of the linker (domain D) and all of the ligand-binding domain (domains E and F) of the EcR polypeptide of the *L. cuprina* ecdysone receptor was excised from a cDNA clone encoding the complete EcR polypeptide and cloned into the SphI-KpnI cleaved expression vector pQE32 (Qiagen), to produce the plasmid pQE32LcEcR.

2. Isolation of the Ligand-Binding Region and Linker Region of the Partner Protein (USP Polypeptide) of the *L. cuprina* Ecdysone Receptor.

A DNA fragment encoding most of the linker domain and all of the ligand-binding domain of the partner protein (USP polypeptide) of the *L. cuprina* ecdysone receptor was subcloned to produce the plasmid pBLU1.

3. Construction of a Baculovirus Expressing the Linker Regions of *L. cuprina* EcR and USP Polypeptides A baculovirus was constructed for the co-expression in insect cells of:

(i) a cDNA region comprising a nucleotide sequence which encodes at least the ligand-binding domain and much of the linker domain of the EcR polypeptide of the *L. cuprina* ecdysone receptor isolated as described at paragraph (1) above; and (ii) a cDNA region comprising a nucleotide sequence which encodes at least the ligand-binding domain and much of the linker domain of the partner protein (USP polypeptide) of the *L. cuprina* ecdysone receptor isolated as described at paragraph (2) above.

To produce this baculovirus, a EcoR I-PstI fragment derived from plasmid pQE32LcEcR, encoding an oligo-His tag and most of the linker domain together with all of the ligand-binding domain of the *L. cuprina* EcR polypeptide was ligated into EcoRI-PstI cleaved pFastBac.DUAL, to produce the plasmid pLcEcR.DUAL. An AvaII-EcoRV fragment, encoding most of the linker and all of the ligand-binding domain of *L. cuprina* partner protein (USP polypeptide) was excised from plasmid pBLU1 and ligated, together with a "FLAG" encoding sequence into the PvuII site of pLcEcR.DUAL, to produce plasmid pLcEcR.USP.DUAL.

The segment of pLcEcR.USP.DUAL which encodes the tagged linker and ligand-binding regions of the EcR polypeptide and partner protein (USP polypeptide) sequences, placed operably under the control of polyhedrin and p10 promoters, respectively, was recombined into a baculovirus genome, by employing the Tn7 transposition system (Luckow et al, (1993). The polypeptide products were then co-expressed in insect Sf21 and Sf9 cells, where they associated into a functional complex.

Expression was examined by immunoblot analysis. Antibodies directed against oligo-His and FLAG tags detected bands on immunoblot analysis of approximately the predicted sizes for the expressed EcR and USP polypeptide regions respectively, in extracts from insect Sf21 cells infected with the recombinant baculovirus. The protein detected by anti-oligo-His was greatly enriched utilising a nickel-NTA resin (Qiagen) and the FLAG-labelled protein purified on FLAG M2 Affinity Gel (Kodak). It was also demonstrated by immunoblot analysis that oligo-His-tagged *L. cuprina* truncated EcR polypeptides and FLAG-tagged *L. cuprina* truncated EcR partner protein (USP polypeptide) bind as a hetero-oligomeric complex to FLAG M2 Affinity Gel (Kodak).

Furthermore, binding assays, carried out by a modification of the method of Yund et al (1978), demonstrated a highly-significant increase in the binding of the tritiated ecdysone analogue, ponasterone A, in cells infected by recombinant virus indicating correct folding and association of the two protein subunits (FIG. 3), greater than that of the ecdysone holoreceptor in L. cuprina embryos. Cells infected by a control virus displayed neither antibody-positive bands on western analysis nor specific binding of tritiated hormone above background.

Expression of the tagged linker and ligand-binding regions of the L. cuprina EcR polypeptide and partner protein (USP polypeptide) sequences was examined by immunoblot analysis of extracts derived from insect Sf21 cells infected with the recombinant baculovirus, employing antibodies directed against the oligo-His and FLAG tags. This analysis detected bands on immunoblot analysis of approximately the predicted sizes for the expressed tagged linker and ligand-binding regions of the L. cuprina EcR polypeptide and partner protein (USP polypeptide).

The protein detected by anti-oligo-His-antibodies was enriched by affinity purification on nickel-NTA resin (Qiagen), and the FLAG-labelled protein was affinity-purified using FLAG M2 Affinity Gel (Kodak).

Furthermore, binding assays, performed using a modification of the method of Yund et al (1978), demonstrated a significant increase in the binding of the labelled ecdysone analogue, [$^3$H]ponasterone A, in cells infected by the recombinant baculovirus, compared to the binding observed for the naturally-occurring ecdysone holoreceptor in L. cuprina embryos (FIG. 3). In contrast, cells infected by a control virus displayed neither antibody-positive bands on western analysis, nor specific binding of [$^3$H]ponasterone A, above background levels.

These data indicate correct folding and association of the variant polypeptides comprising the linker and ligand-binding regions of the L. cuprina EcR polypeptide and L. cuprina partner protein (USP polypeptide). The correctly-folded and associated complex formed by the truncated Ecr polypeptide and truncated EcR partner protein (USP polypeptide), is used for X-ray and NMR structural analysis and for high-throughput screens.

Example 15

A Construct for the Expression of the Ligand-Binding Region of the USP Polypeptide of the L. cuprina Juvenile Hormone Receptor The donor plasmid pLcEcR.USP.DUAL (Example 14) was digested with BssHII and PstI to remove the L. cuprina EcR polypeptide-encoding segment therein, thereby leaving the tagged linker and ligand-binding regions of the L. cuprina USP polypeptide-encoding nucleotide sequence. The digested plasmid was blunt-ended using T4 DNA polymerase and Klenow polymerase, isolated by gel purification, and finally re-ligated to produce the plasmid pLc.USP.SINGLE.

To produce recombinant baculovirus capable of expressing the tagged linker and ligand-binding regions of the USP polypeptide, the segment of pLc.USP.SINGLE encoding this polypeptide and the p10 promoter sequence to which said segment is operably connected, is recombined into a baculovirus genome employing the Tn7 transposition system (Luckow et al., 1993). The polypeptide product is then expressed to form a functional juvenile hormone-binding polypeptide and preferably, a modulator of a juvenile hormone receptor. The correctly-folded truncated USP polypeptide is used for X-ray and NMR structural analysis and for high-throughput screens.

Example 16

In-Vitro Screening for the Detection of Insecticidal Compounds

The EcR partner protein (USP polypeptide) of the insect ecdysone receptor and USP polypeptide of the insect juvenile hormone receptor of the present invention, optionally associated with the EcR polypeptides of insect ecdysone receptors of the present invention as described in the preceding Examples, are coupled to pins according to the procedure of Geysen et al. (1987), and reacted with candidate insecticidal compounds, generally at a concentration in the range from about 0.05 μM to about 100 μM of the candidate compound. The binding of compounds is detected using standard procedures, and compounds having insecticidal activity are identified. Preferably, such compounds exhibit insecticidal activity against a range of insects, including diptera, hemiptera, coleoptera, ants, and moths, amongst others. More preferably, the compounds will exhibit insecticidal activity against L. cuprina, M. persicae, D. melanogaster, scale insect, white fly, and leaf hopper, amongst others. In a particularly preferred embodiment, insecticidal compounds are specific to L. cuprina and/or M. persicae and close relatives thereof.

Example 17

Cloned Myzus persicae EcR/USP Complex Binds Ponasterone A In Vitro

In vitro-translated Myzus persicae EcR (MpEcR) polypeptide and an in vitro-translated M. persicae USP (MpUSP) polypeptide were produced labelled with [$^{35}$S] Methionine, using the Promega TNT-Coupled Reticulocyte Lysate System. Each batch of lysate contained 100-200 mg/ml of endogenous proteins (using BSA as a standard). The products were analysed by SDS-PAGE and radioautography. The results confirmed that the cloned cDNAs encode proteins of the sizes predicted from the length of putative open reading frames of the cDNAs present in plasmids pMpEcR and pMPUSP. The yields of EcR and USP were similar as assessed by SDS-PAGE.

In functional assays, DNA plasmids pMpEcR (AGAL Accession No. NM99/04567; 1 mg) or pMpUSP (AGAL Accession No. NM99/04568; 1 mg), which have been constructed using the vector pBK-CMV, and 1 ml of appropriate TNT RNA Polymerase were added to 48 ml of reaction mix which contained TNT Lysate, TNT Reaction Buffer, amino acid mixture, Rnasin Ribonuclease Inhibitor and nuclease-free water in volumes specified in the manufacture$_F$S protocol. In control reactions, a Luciferase T3 control DNA (Promega) was used in place of pMpEcR or pMpUSP. T7 RNA Polymerase was used for transcription of the M. persicae EcR RNA from plasmid pMpEcR, whilst T3 RNA Polymerase was used for transcription of M. persicae USP RNA from the plasmid pMpUSP and the Luciferase T3 control DNA. The reactions were carried out for 90 minutes at 30° C.

The control reaction produces 150-500 ng of luciferase per 50 ml reaction.

The ecdysteroid binding activities of an in vitro-translated *Myzus persicae* EcR (MpEcR) polypeptide and an in vitro-translated complex of the *M. persicae* EcR and USP polypeptides were produced from the RNAs using the TNT-Coupled Reticulocyte Lysate System (Promega). The mixtures were stored at −20° C. overnight.

After thawing the translation products, 15 ml aliquots of the reaction mixture containing *M. persicae* EcR and USP polypeptides were combined to promote formation of the EcR/USP complex. For assays of individual proteins, 15 ml of the reaction mixture containing *M. persicae* EcR polypeptide or 15 ml of the reaction mixture containing *M. persicae* USP polypeptide was combined with 15 ml of control luciferase protein reaction mixture. Samples were each diluted to 435 ml with EcR40 buffer [40 mM KCl, 25 mM HEPES pH 7.0, 1 mM EDTA, 1 mM DTT, BSA (0.5 mg/ml), 10% glycerol] to allow for triplicates in the ligand binding assay. A control reaction (Blank) was established which contained EcR40 buffer only. An aliquot (140 ml) of each diluted sample was incubated with tritiated ponasterone A (DuPont NEN, Batch Number 3281108) at a final concentration of 2.2 nM for 90 min at room temperature. After incubation, the ligand binding reactions were placed on ice. The samples were pipetted onto Whatman GF/C filters and incubated for 30 sec. The filters were then placed on a vacuum sinter, washed with 10 ml EcR40 buffer and transferred to scintillation vials. After adding 7 ml of InstaGel Plus to each vial, the contents were vortexed and left at room temperature until the filters became transparent. The receptor bound ligand was quantified using a TriCarb 2100TR scintillation counter.

The results depicted in FIG. 4 indicate that significantly higher amounts of ponasterone A bind to the complex than to either the USP or EcR polypeptides alone.

Each reference cited herein is incorporated by reference to the extent that it is not inconsistent with the present disclosure.

REFERENCES

1. Amann and Brosius (1985). *Gene* 40: 183.
2. Ausubel, et al (1992), *Current Protocols in Molecular Biology*, Greene/Wiley, New York
3. Bugg, et al (1993) *Scientific American*, December Issue: pp 60-66.
4. Devereux, J., et al. (1984). *Nucl. Acids Res.* 12:387-395.
5. Evans (1988) *Science,* 240: 889-895.
6. Geysen et al (1987) *J. Immunol. Methods,* 102, 259-274.
7. Greene et al. (1988) *Nucleic Acids Res.* 15:369.
8. Hollenberd and Evans (1988) *Cell* 55: 899-906.
9. Hollenberg et al (1991) *Cell,* 67, 59-77.
10. Jones, G and Sharp, P, (1997) *Proc. Nat. Acad. Sci. USA* 94:13499-13503.
11. Kamimura et al (1996) *Comp. Biochem. Physiol.* 113, 341-347.
12. Koelle et al (1991) *Cell,* 67:59-77
13. Krust et al (1986) *EMBO. J.* 5: 891-897.
14. Luckow et al, (1993) *J. Virol,* 67: 4566.
15. McBurney et al (1991), *Nucleic Acids Res.,* 19, 5755-5761.
16. McPherson, M. J., Quirke, P. and Taylor, G. R. (1991) *PCRA Practical Approach*. IRL Press, Oxford University Press, Oxford, United Kingdom.
17. Needleman and Wunsch (1970) *J. Mol. Biol.* 48:443-453.
18. Potrykus (1990) *Bio/Technology* 8: 535-542.
19. Riddihough, G., and Pelham, H. R. B., (1987), *EMBO J.,* 6, 3729-3734
20. Sambrook et al (1989), *Molecular Cloning: A Laboratory Manual*, Cold Springs Harbor Laboratory Press
21. Segraves and Hogness (1990) *Genes Devel.* 4: 204-219.
22. Shimatake and Rosenberg (1981) *Nature* 292: 128
23. Studier and Moffat (1986) *J. Mol. Biol.* 189: 113
24. Thompson, et al., (1994) *Nucl. Acids Res.* 22:4673-4680.
25. Tzertzinis et al (1994) *J. Mol. Biol.* 258, 479-486.
26. Von Itzstein et al (1993) *Nature Vol.* 363: 418-423.
27. Yund, et al. (1978) *Proc. Nat. Acad. Sci. USA,* 24: 6039-6043.

We claim:

1. An isolated nucleic acid molecule comprising a nucleotide sequence which encodes or is fully complementary to a sequence which encodes an ecdysteroid receptor (EcR) polypeptide that binds ecdysone, wherein the encoded EcR polypeptide has a sequence at least 95% identical to the amino acid sequence set forth in SEQ ID NO:10.

2. The isolated nucleic acid molecule of claim 1, wherein said sequence is at least 95% identical to the nucleotide sequence set forth in SEQ ID NO:9.

3. The isolated nucleic acid molecule of claim 1, wherein the isolated nucleic acid molecule further encodes an EcR partner protein (USP polypeptide) of a *Myzus persicae* EcR heterodimer, which USP polypeptide has a sequence at least 95% identical to the amino acid sequence set forth in SEQ ID NO:12.

4. An isolated nucleic acid molecule comprising a nucleotide sequence which encodes or is fully complementary to a sequence which encodes an ecdysteroid receptor (EcR) polypeptide that binds ecdysone, when said EcR polypeptide is in association with a USP polypeptide, said EcR polypeptide having a sequence at least 95% identical to the amino acid sequence set forth in SEQ ID NO:10.

5. The isolated nucleic acid molecule of claim 4, wherein the EcR polypeptide is derived from a member of the genus *Myzus*.

6. The isolated nucleic acid molecule of claim 5, wherein the member of the genus *Myzus* is *Myzus persicae*.

7. The isolated nucleic acid molecule of claim 4, wherein the isolated nucleic acid molecule further encodes an EcR partner protein (USP polypeptide) of the *M. persicae* EcR polypeptide, wherein the USP polypeptide has a sequence at least 95% identical to the amino acid sequence set forth in SEQ ID NO:12.

8. A genetic construct comprising the isolated nucleic acid molecule of claim 1, wherein said nucleotide sequence is operably linked to a promoter sequence.

9. The genetic construct of claim 8, wherein said promoter sequence is a MMTV, SV40, polyhedrin or p10 promoter sequence.

10. An isolated cell comprising the genetic construct of claim 8.

11. The isolated cell of claim 10, wherein the cell further comprises a nucleic acid molecule encoding an ecdysteroid receptor partner protein (USP polypeptide) which is expressed in said cell.

12. An isolated nucleic acid molecule comprising a nucleotide sequence which encodes a ecdysteroid receptor (EcR) polypeptide, wherein said EcR polypeptide binds ecdysone, and wherein said nucleotide sequence is at least 95% identical to the nucleotide sequence set forth in SEQ ID NO:9 or a sequence fully complementary to said sequence.

13. An isolated nucleic acid molecule comprising a nucleotide sequence which encodes or is fully complementary to a sequence which encodes an ecdysteroid receptor (EcR) polypeptide that binds ecdysone, wherein the encoded EcR polypeptide has a sequence at least 95% identical to the amino acid sequence set forth in SEQ ID NO:10, wherein the isolated nucleic acid molecule further encodes an EcR partner protein (USP polypeptide) of a *Myzus persicae* EcR heterodimer, which USP polypeptide is encoded by the nucleic acid sequence set forth in SEQ ID NO:11.

14. An isolated nucleic acid molecule comprising a nucleotide sequence which encodes or is fully complementary to a sequence which encodes an ecdysteroid receptor (EcR) polypeptide that binds ecdysone, wherein the encoded EcR polypeptide has a sequence at least 95% identical to the amino acid sequence set forth in SEQ ID NO:10, wherein the isolated nucleic acid molecule further encodes an EcR partner protein (USP polypeptide) of a *Myzus persicae* EcR heterodimer, wherein the USP polypeptide is identical to that encoded by cDNA present in plasmid pMpUSP (AGAL Accession No. NM99/04568).

15. An isolated nucleic acid molecule comprising a nucleotide sequence which encodes or is fully complementary to a sequence which encodes an ecdysteroid receptor (EcR) polypeptide that binds ecdysone, wherein the encoded EcR polypeptide has a sequence at least 95% identical to the amino acid sequence set forth in SEQ ID NO:10, wherein the isolated nucleic acid molecule further encodes an EcR partner protein (USP polypeptide) of a *Myzus persicae* EcR heterodimer, wherein said polypeptide consists of an amino acid encoded by a cDNA present in the plasmid deposited under AGAL Accession No. NM99/04567.

* * * * *